United States Patent
Tori

(10) Patent No.: US 11,667,952 B2
(45) Date of Patent: Jun. 6, 2023

(54) METHODS OF PRODUCING NUCLEIC ACIDS USING OLIGONUCLEOTIDES MODIFIED BY A STIMULUS

(71) Applicant: Takara Bio USA, Inc., Mountain View, CA (US)

(72) Inventor: Kazuo Tori, Mountain View, CA (US)

(73) Assignee: Takara Bio USA, Inc., San Jose, CA (US)

( * ) Notice: Subject to any disclaimer, the term of this patent is extended or adjusted under 35 U.S.C. 154(b) by 482 days.

(21) Appl. No.: 16/603,788

(22) PCT Filed: Aug. 23, 2018

(86) PCT No.: PCT/US2018/047816
§ 371 (c)(1),
(2) Date: Oct. 8, 2019

(87) PCT Pub. No.: WO2019/040788
PCT Pub. Date: Feb. 28, 2019

(65) Prior Publication Data
US 2020/0332341 A1 Oct. 22, 2020
US 2020/0332341 A1 Oct. 22, 2020

Related U.S. Application Data

(60) Provisional application No. 62/549,802, filed on Aug. 24, 2017.

(51) Int. Cl.
*C12Q 1/68* (2018.01)
*C12Q 1/6806* (2018.01)

(52) U.S. Cl.
CPC ..... *C12Q 1/6806* (2013.01); *C12Q 2521/301* (2013.01); *C12Q 2525/186* (2013.01); *C12Q 2533/101* (2013.01); *C12Q 2537/163* (2013.01)

(58) Field of Classification Search
CPC .................................................. C12Q 1/6806
See application file for complete search history.

(56) References Cited

U.S. PATENT DOCUMENTS

| | | |
|---|---|---|
| 5,430,136 A | 7/1995 | Urdea et al. |
| 5,965,408 A * | 10/1999 | Short ................ C12N 15/1027 435/6.16 |
| 6,251,639 B1 | 6/2001 | Kurn |
| 6,692,918 B2 | 2/2004 | Kurn |
| 6,858,413 B2 | 2/2005 | Kurn |
| 7,112,406 B2 | 9/2006 | Behlke et al. |
| 7,273,730 B2 | 9/2007 | Du Breuil Lastrucci |
| 7,771,934 B2 | 8/2010 | Kurn |
| 8,399,197 B2 | 3/2013 | Behlke et al. |
| 8,460,874 B2 | 6/2013 | Peleg |
| 8,911,948 B2 | 12/2014 | Walder et al. |
| 2004/0185484 A1 | 9/2004 | Costa et al. |
| 2005/0202490 A1 | 9/2005 | Makarov et al. |
| 2007/0031857 A1 | 2/2007 | Makarov et al. |
| 2008/0145844 A1 | 6/2008 | Barsova et al. |
| 2010/0167954 A1 | 7/2010 | Earnshaw et al. |
| 2010/0297709 A1 | 11/2010 | Rashtchian |
| 2011/0294674 A1 | 12/2011 | Cheung et al. |
| 2011/0319290 A1 | 12/2011 | Raymond et al. |
| 2012/0196279 A1 | 8/2012 | Underwood et al. |
| 2012/0316074 A1 | 12/2012 | Saxonov |
| 2014/0093916 A1 * | 4/2014 | Belyaev ............... C12Y 207/07 435/91.2 |
| 2014/0378322 A1 | 12/2014 | Hindson et al. |
| 2015/0111789 A1 | 4/2015 | Betts et al. |
| 2016/0046995 A1 | 2/2016 | Kochanczyk et al. |
| 2016/0257985 A1 | 9/2016 | Kamberov et al. |
| 2017/0037465 A1 * | 2/2017 | Tsavachidou ........ C12Q 1/6806 |

FOREIGN PATENT DOCUMENTS

| | | |
|---|---|---|
| WO | WO9637630 A1 | 11/1996 |
| WO | WO2001020035 A2 | 3/2001 |
| WO | WO2002004630 A2 | 1/2002 |
| WO | WO2007062445 A1 | 6/2007 |
| WO | WO2007147110 A2 | 12/2007 |
| WO | WO2009151921 A1 | 12/2009 |
| WO | WO2012082753 A2 | 6/2012 |
| WO | WO2012103154 A1 | 8/2012 |
| WO | WO2015161060 A1 | 10/2015 |
| WO | WO2016081551 A1 | 5/2016 |

OTHER PUBLICATIONS

Guo et al. (An Integrated System for DNA Sequencing by Synthesis Using Novel Nucleotide Analogues, Accounts of Chemical Research 43(4):551-563, Apr. 2010). (Year: 2010).*
Howell et al., Glycosylases and AP-cleaving enzymes as a general tool for probe-directed cleavage of ssDNA targets, Nucleic Acids Research, 2010, vol. 38, No. 7, p. 1-10.
Lebedev et al., Hot Start PCR with heat-activatable primers: a novel approach for improved PCR performance, Nucleic Acids Research, 2008, vol. 36, No. 20, p. 1-18.
Liu et al., Optochemical Control of Deoxyoligonucleotide Function via a Nucleobase-Caging Approach, Accounts of Chemical Research, 2014, vol. 47, No. 1, p. 45-55.
Walder et al., Use of PCR primers containing a 3'-terminal ribose residue to prevent cross-contamination of amplified sequences, Nucleic Acids Research, 1993, vol. 21, No. 18, p. 4339-4343.

* cited by examiner

Primary Examiner — Jezia Riley
(74) Attorney, Agent, or Firm — Bret E. Field; Bozicevic, Field & Francis LLP

(57) ABSTRACT

Provided are methods of producing product nucleic acids involving the use of oligonucleotides that are modified by the application of a stimulus. Aspects of such methods may include producing product nucleic acids using de-activatable oligonucleotides that are deactivated by a de-activating stimulus, as well as methods that may include producing product nucleic acids using activatable oligonucleotides that are activated by an activating stimulus and de-activatable oligonucleotides that are deactivated by a de-activating stimulus. Also provided are kits, compositions and devices that include de-activatable oligonucleotides or activatable and de-activatable oligonucleotides, e.g., for use in performing the methods as described herein.

19 Claims, 10 Drawing Sheets
Specification includes a Sequence Listing.

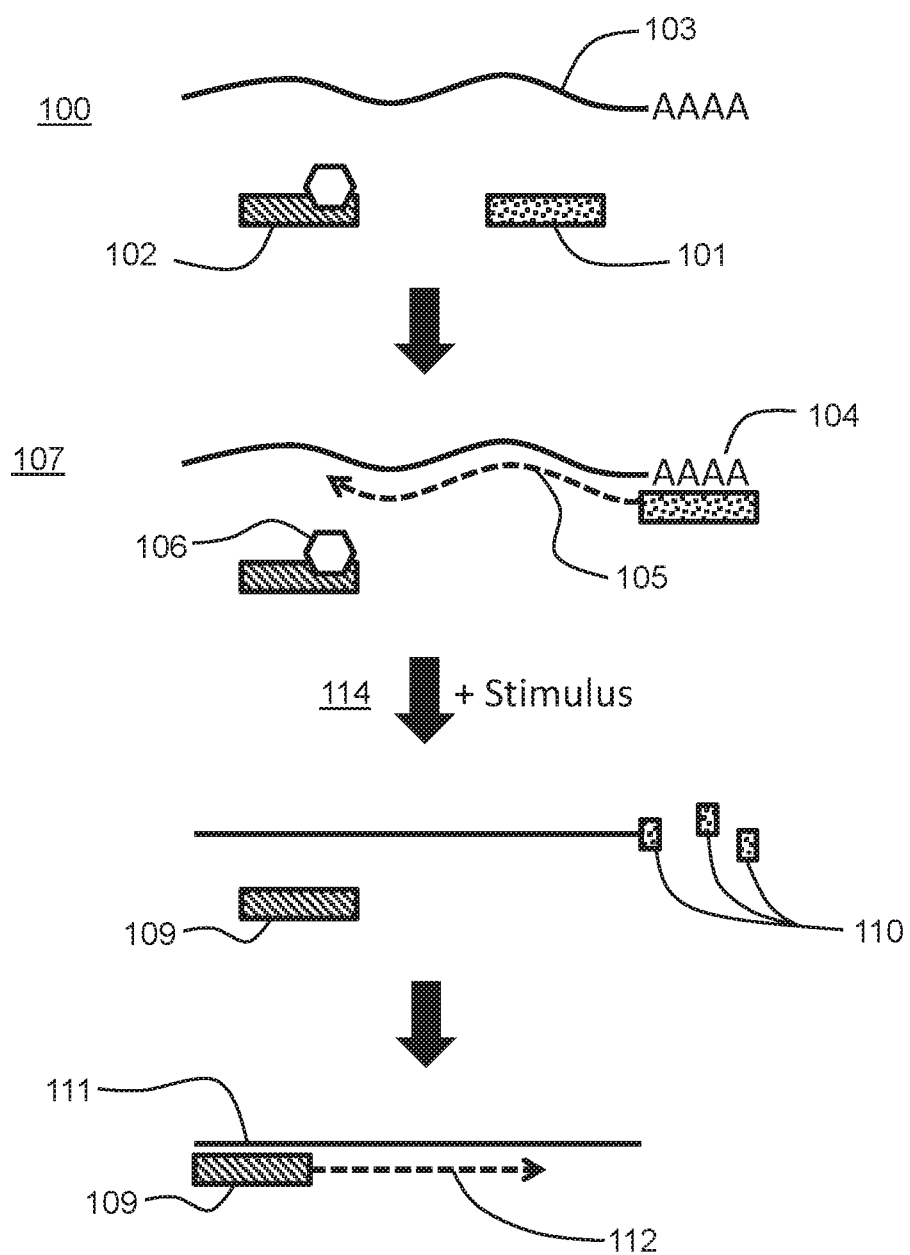

CDS5R: AAGCAGTGrGTATCAACrGCAGAGTArCTTTTTTTTTTTTTTTTrUTTTTTTTVN

FIG. 4

TSO3R: AAGCArGTGGTATrCAACGCrAGAGTACrGrGrG

FIG. 5

S502: AATGATACGGCGACCACCGAGATCTACACCTCTCTATTCGTCGGCAGCGTC
Activatable: AATGATACGGCGACCACCGAGATCTACACCTCTCTATTCGTCGGCAGCGTCrUCGGTGGTCrGCCGTATCAT*T/3Phos/
S502

➡

AATGATACGGCGACCACCGAGATCTACACCTCTCTATTCGTCGGCAGCG
                                              TCUCGGGTGGTCGCCGTATCATT/3Phos/

FIG. 6

N701: CAAGCAGAAGACGGCATACGAGATTCGCCTTAGTCTCGTGGGCTCGG
Activatable: CAAGCAGAAGACGGCATACGAGATTCGCCTTAGTCTCGTGGGCTCGrUATGCCGTrCTTCTGCTT*G/3Phos/
N701

➡

CAAGCAGAAGACGGCATACGAGATTCGCCTTAGTCTCGTGGG
                                         CTCGUATGCCGTCTTCTGCTTG/3Phos/

FIG. 7

FIG. 13
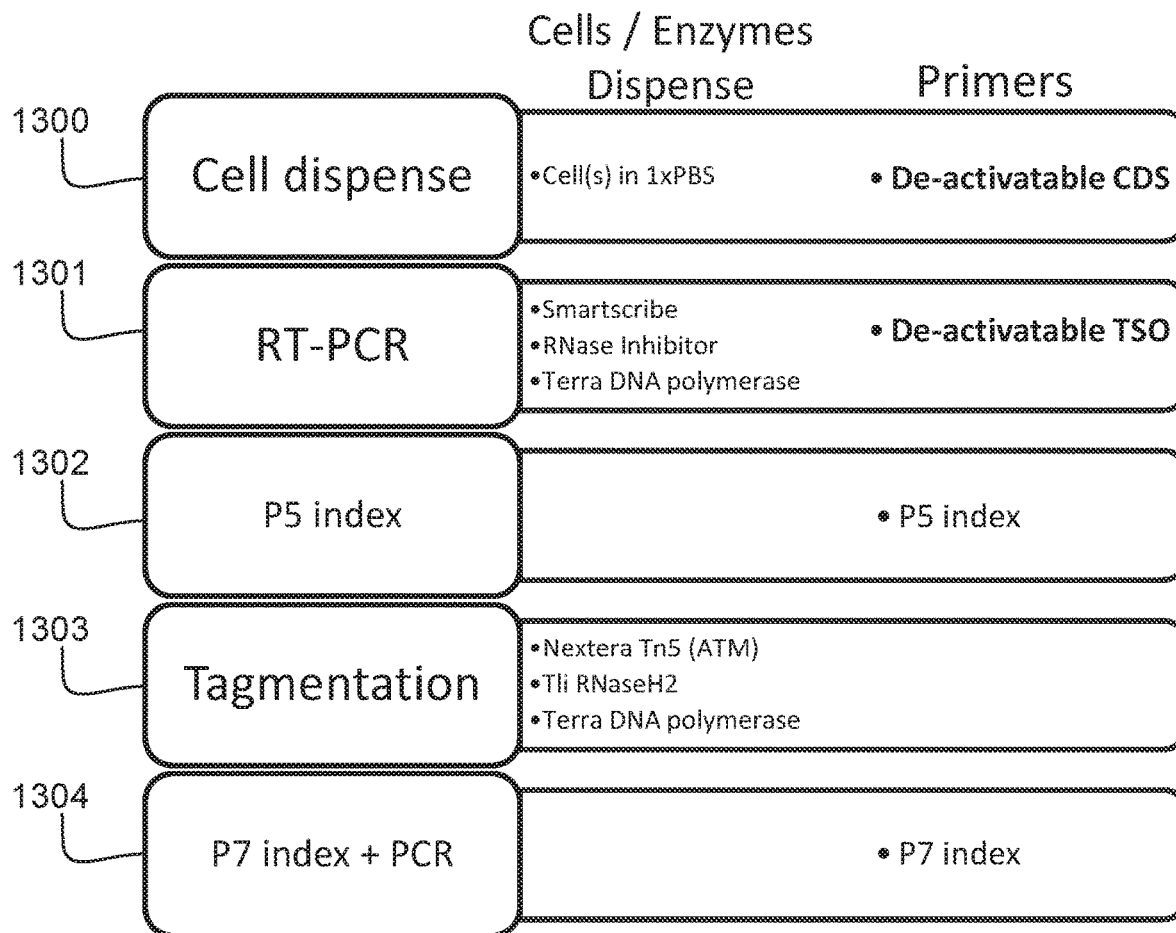
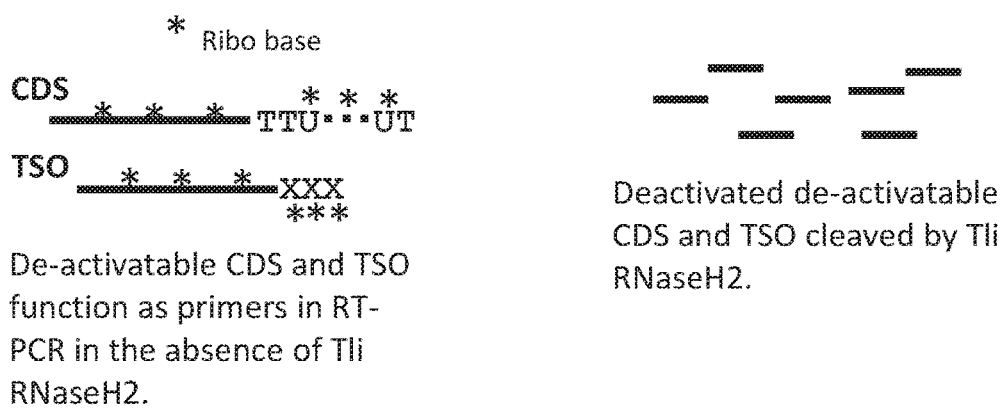

METHODS OF PRODUCING NUCLEIC ACIDS USING OLIGONUCLEOTIDES MODIFIED BY A STIMULUS

CROSS-REFERENCE TO RELATED APPLICATIONS

Pursuant to 35 U.S.C. § 119(e), this application claims priority to the filing date of the U.S. Provisional Patent Application Ser. No. 62/549,802, filed Aug. 24, 2017, the disclosure of which application is herein incorporated by reference.

INTRODUCTION

The development of next generation sequencing (NGS) technologies has allowed for the rapid extraction of valuable genomic and transcriptomic information from produced nucleic acid libraries. High throughput NGS technologies, such as Illumina (Solexa) sequencing, Roche 454 sequencing, Ion torrent (Proton/PGM sequencing) and SOLiD sequencing, allow the sequencing of nucleic acid molecules more quickly and cheaply than previously used Sanger sequencing, and as such these techniques have revolutionized biotechnology and biomedical research. In addition, as these technologies mature and become more user-friendly, their presence in clinical applications will continue to increase.

These powerful sequencing technologies place a particular emphasis on library preparation. Well-prepared and efficiently produced reverse transcribed complementary DNA (cDNA) libraries can be analyzed using NGS technologies for a diverse range of purposes.

Somatic mutations, spontaneous variants that accumulate in cells over a lifetime, are a major factor that drives disease onset and reoccurrence. As cells accumulate new mutations, they form polyclonal cell populations that co-exist with normal cells. Sequencing bulk cell populations can mask the underlying heterogeneity of these unique rare cell types, making it difficult to distinguish them from normal germline mutations. Where nucleic acid libraries are prepared from individual cells, NGS technologies allow for the analysis of genomic and/or transcriptomic changes at single cell resolution.

SUMMARY

Provided are methods of producing product nucleic acids involving the use of oligonucleotides that are modified by the application of a stimulus. Aspects of such methods may include producing product nucleic acids using de-activatable oligonucleotides that are deactivated by a de-activating stimulus, as well as methods that may include producing product nucleic acids using activatable oligonucleotides that are activated by an activating stimulus and de-activatable oligonucleotides that are deactivated by a de-activating stimulus. Also provided are kits, compositions and devices that include de-activatable oligonucleotides or activatable and de-activatable oligonucleotides, e.g., for use in performing the methods as described herein.

BRIEF DESCRIPTION OF THE FIGURES

FIG. 1A-1E provide schematic depictions of nucleic acid production using de-activatable and/or activatable and de-activatable oligonucleotides according to embodiments described herein.

FIG. 4 provides an example of a de-activatable reverse transcription polymerase chain reaction (RT-PCR) first strand synthesis primer.

FIG. 5 provides an example of a de-activatable template-switching oligonucleotide.

FIG. 6 provides an example of an index sequence-containing activatable primer.

FIG. 7 provides an example of an index sequence-containing activatable primer.

FIG. 13 provides a schematic depiction of a library preparation workflow employing a de-activatable CDS primer and a de-activatable template switching oligonucleotide.

DEFINITIONS

Figure 1A:
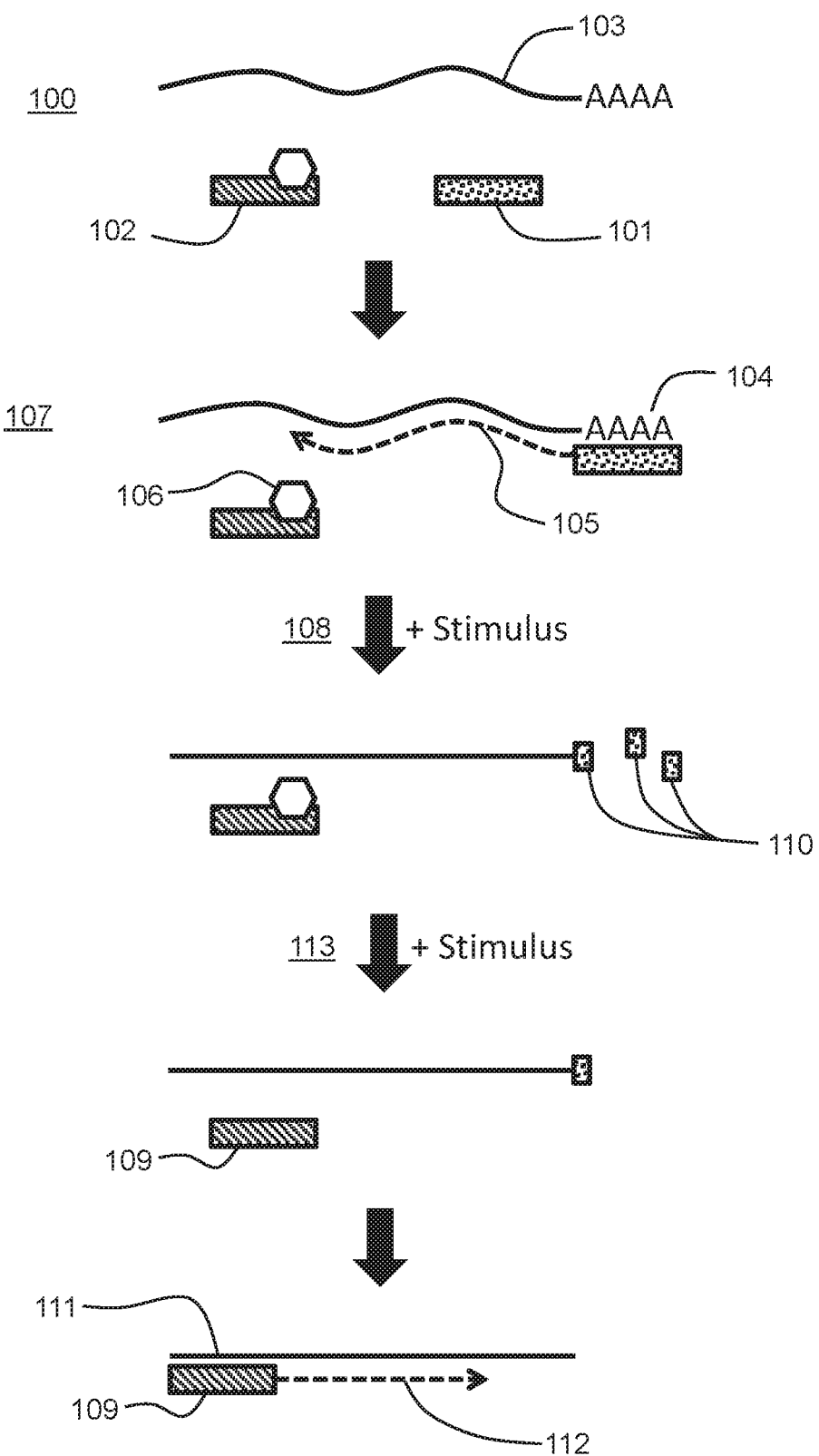

As used herein, the term "hybridization conditions" means conditions in which a primer, or other polynucleotide, specifically hybridizes to a region of a target nucleic acid with which the primer or other polynucleotide shares some complementarity. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The terms "complementary" and "complementarity" as used herein refer to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%).

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions× 100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

A "domain" refers to a stretch or length of a nucleic acid made up of a plurality of nucleotides, where the stretch or length provides a defined function to the nucleic acid. Examples of domains include Barcoded Unique Molecular Identifier (BUMI) domains, primer binding domains, hybridization domains, barcode domains (such as source barcode domains), unique molecular identifier (UMI) domains, Next Generation Sequencing (NGS) adaptor domains, NGS indexing domains, etc. In some instances, the terms "domain" and "region" may be used interchangeably, including e.g., where immune receptor chain domains/regions are described, such as e.g., immune receptor constant domains/regions. While the length of a given domain may vary, in some instances the length ranges from 2 to 100 nt, such as 5 to 50 nt, e.g., 5 to 30 nt.

Amplification primer binding domains are domains that are configured to bind via hybridization to an amplification primer. Pre-tagmentation amplification primer binding domains are domains which are configured to bind to pre-tagmentation amplification primers during an amplification that occurs before a tagmentation step, e.g., a cDNA amplification protocol which occurs prior to a tagmentation step. Post-tagmentation amplification primer binding domains are domains which are configured to bind to post-tagmentation amplification primers during an amplification that occurs after a tagmentation step, e.g., a tagmented sample amplification protocol which occurs after to a tagmentation step.

The terms "unique molecular identifiers" and "UMIs" refer to randomers of varying length, e.g., ranging in length in some instances from 6 to 12 nts, that can be used for counting of individual molecules of a given molecular species. In some instances, counting is facilitated by attaching UMIs from a diverse pool of UMIs to individual molecules of a target of interest such that each individual molecule receives a unique UMI. In such instances, by counting individual transcript molecules, PCR bias can be reduced during NGS library prep and a more quantitative understanding of the sample population can be achieved. UMIs may, in some instances, be used in conjunction with other barcode sequences such as a source barcode sequence (e.g., cell barcode sequences, sample barcode sequences, well barcode sequences and the like).

DETAILED DESCRIPTION

Provided are methods of producing product nucleic acids involving the use of oligonucleotides that are modified by the application of a stimulus. Aspects of such methods may include producing product nucleic acids using de-activatable oligonucleotides that are deactivated by a de-activating stimulus, as well as methods that may include producing product nucleic acids using activatable oligonucleotides that are activated by an activating stimulus and de-activatable oligonucleotides that are deactivated by a de-activating stimulus. Also provided are kits, compositions and devices that include de-activatable oligonucleotides or activatable and de-activatable oligonucleotides, e.g., for use in performing the methods as described herein.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

As summarized above, aspects of the provided methods include the use of oligonucleotides that are modifiable by the application of a stimulus. Modifiable oligonucleotides include de-activatable oligonucleotides and activatable oligonucleotides. Such methods may include the use of de-activatable oligonucleotides or activatable and de-activatable oligonucleotides to produce product nucleic acids.

In some instances, the modifiable oligonucleotides employed in a subject method may include only de-activatable oligonucleotides, including only one type of de-activatable oligonucleotide or multiple different types of de-activatable oligonucleotides. In some instances, the modifiable oligonucleotides employed in a subject method may include only activatable oligonucleotides, including only one type of activatable oligonucleotide or multiple different types of activatable oligonucleotides. In some instances, the modifiable oligonucleotides employed in a subject method may include both de-activatable oligonucleotides and activatable oligonucleotides.

In some instances, activatable and de-activatable oligonucleotides may be activated and de-activated, respectively, by the same stimulus. In some instances, multiple different activatable oligonucleotides may be activated by the same stimulus. In some instances, multiple different de-activatable oligonucleotides may be deactivated by the same stimulus. In some instances, activatable and de-activatable oligonucleotides may be activated and de-activated, respectively, by different stimuli. In some instances, multiple different activatable oligonucleotides may be activated by different stimuli. In some instances, multiple different de-activatable oligonucleotides may be deactivated by different stimuli. Where different stimuli are employed to activate and/or deactivate the oligonucleotides, the different stimuli may be applied simultaneously or sequentially in any convenient order.

Accordingly, in some instances, a single stimulus may modulate the activity of multiple different modulatable oligonucleotides, including e.g., multiple activatable oligonucleotides, multiple de-activatable oligonucleotides, or a combination of activatable and de-activatable oligonucleotides. For example, the subject methods may include where multiple different modulatable oligonucleotides are present in a reaction mixture and a single stimulus is added or applied to the reaction mixture to modulate the activities (e.g., activate and/or deactivate) of the multiple different modulatable oligonucleotides.

In some instances, a single stimulus may activate multiple different activatable oligonucleotides. In some instances, a single stimulus may deactivate multiple different de-activatable oligonucleotides. In some instances, a single stimulus may activate an activatable oligonucleotide and deactivate a de-activatable oligonucleotide. For example, the subject methods may include where an activatable oligonucleotide and a de-activatable oligonucleotide are both present in a reaction mixture and a single stimulus is added or applied to the reaction mixture to activate the activatable oligonucleotide and deactivate the de-activatable oligonucleotide.

In some instances, a first stimulus may deactivate a first de-activatable oligonucleotide and a second stimulus may deactivate a second de-activatable oligonucleotide. In some instances, a first stimulus may activate a first activatable oligonucleotide and a second stimulus may activate a second activatable oligonucleotide In some instances, a first stimulus may deactivate a de-activatable oligonucleotide and a second stimulus may activate an activatable oligonucleotide. For example, the subject methods may include where an activatable oligonucleotide and a de-activatable oligonucleotide are both present in a reaction mixture and a first stimulus is added or applied to the reaction mixture to deactivate the de-activatable oligonucleotide and then a second stimulus is added or applied to activate the de-activatable oligonucleotide. Thus, the oligonucleotides may be deactivated and/or activated sequentially. In some instances, the different stimuli (i.e., the first and second stimuli) may be added or applied simultaneously to the reaction mixture resulting in the simultaneous activation and/or deactivation of the oligonucleotides.

By "simultaneous", as used herein with regards to activation/deactivation of oligonucleotides, is generally meant where the activation and deactivation events occur at the exact same time as well as where the events are close enough in time to function within the reaction mixture as having occurred at the same time. Put another way, in some instances, simultaneous activation/deactivation of the oligonucleotides may include where the activation and deactivation events are separated in time to such a small degree that the reaction mixture functions as if un-activated activatable oligonucleotide and active de-activatable oligonucleotide are not simultaneously present in any significant amount for any significant amount of time. Similarly, in some instances, simultaneous activation of the oligonucleotides may include where two activation events are separated in time to such a small degree that the reaction mixture functions as if an un-activated first activatable oligonucleotide and an active second activatable oligonucleotide are not simultaneously present in any significant amount for any significant amount of time. Correspondingly, in some instances, simultaneous deactivation of the oligonucleotides may include where two de-activation events are separated in time to such a small degree that the reaction mixture functions as if an active first de-activatable oligonucleotide and a de-activated second de-activatable oligonucleotide are not simultaneously present in any significant amount for any significant amount of time. For example, although the rates of activation/deactivation, or the initiation thereof, may vary where different stimuli (e.g., where a light or heat stimulus and an enzymatic stimulus) are employed, simultaneous or near simultaneous application of such stimuli will generally be considered to describe simultaneous activation/deactivation by the stimuli.

The sequential application of stimuli will generally include where a first stimulus and second stimulus are applied in two separate steps. The application of the first stimulus and the application of the second stimulus may or may not be separated by one or more intervening steps. In contrast to simultaneous activation/deactivation of activatable and/or de-activatable oligonucleotides present in a reaction mixture, sequential deactivation/activation of activatable and/or de-activatable oligonucleotides may, e.g., result in a deactivated de-activatable oligonucleotide being present in a reaction mixture in a significant amount for a significant amount of time with an un-activated activatable oligonucleotide. Correspondingly, where sequential activation is employed, different first and second activatable oligonucleotides may be present in a reaction mixture in activated and un-activated forms, respectively, in a significant amount for a significant amount of time. Where sequential de-activation is employed, different first and second de-activatable oligonucleotides may be present in a reaction mixture in activated and de-activated forms, respectively, in a significant amount for a significant amount of time.

In their active forms the de-activatable oligonucleotide and the activatable oligonucleotide may contribute one or more activities to a reaction mixture, for example, to allow for the production of a desired nucleic acid, e.g., a final product nucleic acid, an intermediate nucleic acid used in one or more subsequent nucleic acid production steps, and/or the like.

The activatable and de-activatable activities of the oligonucleotides referred to may include the ability of the oligonucleotide to hybridize to a complementary region of nucleotide sequence, the ability of the oligonucleotide to facilitate primer extension/elongation by a polymerase, the ability of an oligonucleotide to serve as a template in a template-switching reaction, combinations thereof and the like. Accordingly, "activatable oligonucleotides" include those oligonucleotides that are essentially inactive or otherwise not permissive for use in an extension/elongation reaction or amplification reaction in their default state and may be activated or made otherwise permissive to an extension/elongation or amplification reaction by a stimulus.

In contrast, "de-activatable oligonucleotides" include those oligonucleotides that are essentially active or otherwise permissive to be used in an extension/elongation or amplification reaction in their default state and may be deactivated or made otherwise not permissive for use in an extension/elongation or amplification reaction by a stimulus.

In some embodiments, two oligonucleotides employed in a subject reaction mixture may not be simultaneously active for any substantial amount of time. Prevention of the simultaneous activity of two oligonucleotides may be achieved e.g., through the use of oligonucleotides activated and de-activated by the same stimulus, the simultaneous activation/deactivation of two oligonucleotides by different stimuli or the like. Preventing the simultaneous activity of two oligonucleotides, in some instances, allows for the activatable or de-activatable oligonucleotide to be present in a reaction mixture without negatively impacting the reaction at points where one of the two oligonucleotides may not be necessary or otherwise involved in the reaction. For example, an inactive activatable oligonucleotide, which could interfere with a reaction in its active form, may be present in the reaction mixture without interfering. Such activatable oligonucleotides will generally be useful in subsequent reaction steps, i.e., reaction steps that follow other reaction steps where the active form of the activatable oligonucleotide could negatively interfere. Similarly, an inactive (i.e., deactivated) de-activatable oligonucleotide, which could interfere with a later reaction in its active form, may be present in the later reaction without interfering. Such inactive de-activatable oligonucleotides will generally be useful in early or initial reaction steps that precede one or more subsequent reaction steps where the active form of the de-activatable oligonucleotide could interfere.

Interference in a particular reaction step by an oligonucleotide that is not required for the subject step (i.e., an unnecessary oligonucleotide) encompasses essentially any negative impact, potential or observed, that the presence of the unnecessary oligonucleotide may have. Such negative impacts include but are not limited to e.g., where one or more sequences within the unnecessary oligonucleotide may specifically interfere with the interaction between other nucleic acids (i.e., template nucleic acids, oligonucleotides, primers, probes, etc.) that are necessary during the subject reaction step. For example, a sequence within the unnecessary oligonucleotide may hybridize with one or more of the other essential nucleic acids preventing or decreasing the frequency of a necessary hybridization interaction between the reaction components during the subject reaction step. Alternatively, a sequence within the unnecessary oligonucleotide may hybridize with one or more nucleic acids preventing or decreasing the processivity of a polymerase. In some instances, an unnecessary oligonucleotide may interfere with an amplification step or other downstream reaction step to which the reaction mixture, or an aliquot thereof, is subjected to. In some instances, activity of an unnecessary oligonucleotide present during an amplification reaction may lead to background amplification or otherwise undesirable amplification products or even no amplification.

In some instances, the oligonucleotides of the reaction mixture (e.g., a de-activatable oligonucleotide and an activatable oligonucleotide) may interfere with each other, e.g., a first oligonucleotide may interfere with hybridization of a second oligonucleotide to a hybridization site, a first and second oligonucleotide may hybridize to each other, or the like. Such interactions may arise, e.g., because the two different oligonucleotides contain the same or similar sequence(s), because the two oligonucleotides contain complementary or near complementary sequence(s), etc. For example, in some instances, the activatable oligonucleotide may include a sequence identical to a sequence present in the de-activatable oligonucleotide. In some instances, the activatable oligonucleotide may include a sequence complementary to a sequence present in the de-activatable oligonucleotide. In some instances, a sequence shared between two different oligonucleotides may be a non-templated sequence, e.g., a primer binding site, an index or adapter sequence, a barcode sequence, etc.

In some instances, two oligonucleotides employed in a reaction mixture may not share complementary regions and/or identical or highly similar regions and, as such, the two oligonucleotides may not, even when both are active, substantially hybridize to one another and/or substantially hybridize to the same target sequence. In some instances, e.g., but not necessarily, where two oligonucleotides do not share substantial complementarity or similarity/identity, two oligonucleotides present in a reaction mixture may, when both are active, indirectly interfere with each other. By "indirectly interfere", in this context, is meant that the two oligonucleotides may share significantly similar functional characteristics, regardless of whether they share similarity/identity or complementarity, such that they are correspondingly influenced by the same reaction conditions. For example, in some instances, two oligonucleotides may indirectly interfere by nature of having the same or significantly similar thermodynamic characteristics (e.g., melting/annealing temperature, etc.). Accordingly, in some instances, an activatable oligonucleotide and a de-activatable oligonucleotide present a reaction mixture, in their respective active forms, may have Tm's that are the same or substantially similar (e.g., within ±10 or less of each other, including e.g., within ±5 or less, within ±3° or less, within ±2° or less, within ±1° or less, etc.). Two oligonucleotides, e.g., an active activatable oligonucleotide and an active de-activatable oligonucleotide, may not necessarily have Tm's that are the same or substantially similar. Thus, in some instances, the two oligonucleotides may be designed to have Tms that are not the same or not substantially similar.

The de-activatable oligonucleotide may be further designed, in some instances, such that when deactivated by cleaving into multiple fragments, the individual fragments have Tms insufficient to initiate amplification of other regions, e.g., under the further reaction conditions to which the fragments are subjected. In addition, de-activatable oligonucleotides may be further designed, in some instances, such that when deactivated by cleaving into multiple fragments, the fragments do not form dimers with one another.

Where present, the length of identical and/or complementary sequences of the subject oligonucleotides may vary and may range from the entire length of one or more of the oligonucleotides or less than the entire length including 90% or more, 80% or more, 70% or more, 60%, or more, 50% or more, less than 50%, 40% or less, 30% or less, 20% or less, 10% or less, etc., of the length of the oligonucleotide. In some instances, the length of an identical and/or complementary sequence contained within one or more of the oligonucleotides may range from less than 10 nt to 100 nt or more, including but not limited to e.g., 10 nt to 100 nt, 15 nt to 100 nt, 20 nt to 100 nt, 25 nt to 100 nt, 30 nt to 100 nt, 10 nt to 50 nt, 15 nt to 50 nt, 20 nt to 50 nt, 25 nt to 50 nt, 30 nt to 50 nt, 10 nt to 15 nt, 10 nt to 15 nt, 10 nt to 20 nt, 10 nt to 25 nt, 10 nt to 30 nt, etc.

In some instances, providing oligonucleotides in activatable and/or de-activatable forms to a reaction mixture may reduce the need for sample handling and/or reagent addition during processing. In some instances, using oligonucleotides in activatable and/or de-activatable forms allows for the oligonucleotides to be pre-loaded into a reaction mixture or vessel to which a reaction mixture is to be added, thus simplifying many aspects of nucleic acid production while decreasing the risks of cross-contamination and incorrect reagent mixing by a user. In addition, in embodiments where the same stimulus is utilized to activate and/or deactivate activatable and/or de-activatable oligonucleotides, reaction processing may be further simplified increasing the likelihood of reaction success. For example, using a single stimulus may prevent inadvertent skipping of an oligonucleotide deactivation or activation step, i.e., skipping of a step that may otherwise be possible if separate activation/deactivation stimuli were employed. In some instances, use of a single activating/deactivating stimulus may assure that the respective oligonucleotides are activated and deactivated at the same time, e.g., preventing overlapping activated states of the activatable and de-activatable oligonucleotides, deactivating two different de-activatable oligonucleotides at the same time, activating two difference activatable oligonucleotides at the same time, etc. In some instances, the use of separate or different stimuli may provide for greater control and/or flexibility of the timing and/or extent of activation/deactivation of activatable/de-activatable oligonucleotides present in a reaction mixture. Such advantages of the subject methods are merely exemplary and not intended to be required, exhaustive or limiting in any way.

Stimuli useful in the methods of the present disclosure for activating an activatable oligonucleotide and/or deactivating a de-activatable oligonucleotide will vary and may include e.g., enzymatic stimuli, chemical stimuli, electromagnetic stimuli, physical stimuli, and the like. As described in more detail below, activation/deactivation of oligonucleotides of the provided methods may involve selectively cleaving a linkage present in the oligonucleotides, including e.g., selectively cleaving a selectively cleavable linkage present in the activatable oligonucleotide and/or a selectively cleavable linkage present in the de-activatable oligonucleotide. Cleavable linkages may be natural backbone linkages (e.g., internucleotide DNA phosphate backbone linkages, internucleotide RNA phosphate backbone linkages), non-natural (i.e., synthetic) backbone linkages or a linkage formed by an incorporated non-natural nucleotide (e.g., a uracil-containing nucleotide present in a DNA strand, nucleotide analogs, and the like), such as e.g., a backbone linkage between the oligonucleotide and the incorporated non-natural nucleotide, a glycosidic bond within the non-natural nucleotide, and the like. Non-limiting examples of non-natural backbone linkages include but are not limited to backbone linkages between DNA and RNA nucleotides, synthetic phosphate backbone linkages (e.g., alternatives to the phosphodiester backbone such as, e.g., phosphorothioate, boranophosphate, phosphonate, etc.), synthetic backbone linkages between non-naturally occurring nucleotides, and the like. As such, useful stimuli will generally, but not necessarily, include the functional ability to facilitate such cleavage.

Useful enzymatic stimuli include enzymes capable of cleaving selectively cleavable linkages present in an activatable oligonucleotide and/or a de-activatable oligonucleotide, to correspondingly activate/deactivate the relevant oligonucleotides. Useful enzymes may selectively cleave a particular linkage present an oligonucleotide including e.g., where such a linkage may be present at or near (i.e., within one or two nucleotides from) the 3' end, at or near (i.e., within one or two nucleotides from) the 5' end, within the polynucleotide (i.e., an internucleotide linkage), combinations thereof and the like. For example, in some instances, enzymatic cleavage at or near the end (i.e., 3' or 5' end) of the oligonucleotide may remove or resolve a blocking moiety allowing an activatable oligonucleotide to be used in an elongation reaction or other nucleic acid production step. In some instances, enzymatic cleavage within a de-activatable oligonucleotide may fragment the oligonucleotide rendering it unable to substantially interfere with subsequent elongation reactions or other nucleic acid production steps.

Useful enzymatic stimuli for enzymatically cleaving nucleotide linkages present in the subject oligonucleotides include nucleases. For example, in some instances, a ribonuclease may be employed to cleave ribonucleotide linkages present in the activatable oligonucleotides and/or de-activatable oligonucleotides. In some embodiments, ribonuclease H may be employed, e.g., to selectively cleave at DNA:RNA hybridized ribonucleotides, e.g., present in primarily DNA oligonucleotides. Useful nucleases also include restriction endonucleases, including e.g., nicking endonucleases (i.e., "nickases"). For example, in some instances, a nickase may be employed to cleave nucleotide linkages present in an activatable oligonucleotide and/or a de-activatable oligonucleotide as directed by enzyme recognition sequences within the oligonucleotides. In some instances, nucleases may include Cas9 nuclease or any other nuclease derived from Cas9. Such nuclease mediated cleavage may deactivate a de-activatable oligonucleotide (e.g., through fragmentation of the de-activatable oligonucleotide) and/or activate the activatable oligonucleotide (e.g., through removing a blocking moiety or resolving a tertiary structure such as a stem-loop present in the activatable oligonucleotide). In some instances, useful enzymatic stimuli may be thermostable or thermolabile as desired. For example, useful thermostable enzymatic stimuli include but are not limited to e.g., thermostable nucleases such as e.g., a thermostable RNase (e.g., thermostable RNase H), a thermostable restriction enzyme, etc. Useful thermolabile enzymatic stimuli include but are not limited to e.g., thermolabile nucleases such as e.g., a thermolabile RNase (e.g., thermolabile RNase H), a thermolabile restriction enzyme, etc. Useful enzymatic stimuli will vary and are not limited to those specifically described.

Useful chemical stimuli will generally, but not necessarily, include chemicals capable of cleaving selectively cleavable linkages present in an activatable oligonucleotide and/or a de-activatable oligonucleotide, to correspondingly activate/deactivate the relevant oligonucleotides. Useful chemicals may selectively cleave a particular linkage present in an oligonucleotide including e.g., where such a linkage may be present at or near (i.e., within one or two nucleotides from) the 3' end, at or near (i.e., within one or two nucleotides from) the 5' end, and/or anywhere within the polynucleotide (i.e., an internucleoside linkage), or combinations thereof and the like. For example, in some instances, chemical cleavage at or near the end (i.e., 3' or 5' end) of the oligonucleotide may remove or resolve a blocking moiety allowing an activatable oligonucleotide to be used in an elongation reaction or other nucleic acid production step. In some instances, chemical cleavage within a de-activatable oligonucleotide may fragment the oligonucleotide rendering it unable to substantially interfere with subsequent elongation reactions or other nucleic acid production steps.

Useful chemical stimuli include those agents that specifically cleave modified nucleotides incorporated into nucleotide strands. For example, incorporated nucleotide analogs 5-hydroxy-dCTP, 5-hydroxy-dUTP, 7-Deaza-7-nitro-dATP, 7-deaza-7-nitro-dGTP may be specifically cleaved using the chemical stimulus pyrrolidine, including e.g., those described in Wolfe et al. (PNAS. 2002; 99(17):11073-8; the disclosure of which is incorporated herein by reference in its entirety). Useful chemical stimuli also include synthetic (i.e., artificial) sequence specific chemical nucleases, such as e.g., EDTA conjugated oligonucleotides, including e.g., those described in Dreyer & Dervan (PNAS. 1985; 82(4): 968-972; the disclosure of which is incorporated herein by reference in its entirety). Useful chemical stimuli may, in some instances, include chemicals for adjustment of reaction mixture pH, i.e., a pH adjusting agent. For example, an acid or acidic buffer may be employed as a chemical stimulus to decrease reaction mixture pH or a base or basic buffer may be employed as a chemical stimulus to increase reaction mixture pH. Such adjustments of pH may provide sufficient stimulus to modify the activity of a modifiable oligonucleotide, activating an activatable oligonucleotide and/or deactivating a de-activatable oligonucleotide. Useful chemical stimuli will vary and are not limited to those specifically described.

Useful electromagnetic stimuli will generally, but not necessarily, include forms of electromagnetic radiation capable of cleaving selectively cleavable linkages present in an activatable oligonucleotide and/or a de-activatable oligonucleotide, to correspondingly activate/deactivate the relevant oligonucleotides. Useful forms of electromagnetic radiation may selectively cleave a particular linkage of an oligonucleotide including e.g., where such a linkage may be present at or near (i.e., within one or two nucleotides from) the 3' end, at or near (i.e., within one or two nucleotides from) the 5' end, within the polynucleotide (i.e., an internucleoside linkage), combinations thereof and the like. For example, in some instances, electromagnetic induced cleavage at or near the end (i.e., 3' or 5' end) of the oligonucleotide may remove or resolve a blocking moiety allowing an activatable oligonucleotide to be used in an elongation reaction or other nucleic acid production step. In some instances, electromagnetic induced cleavage within a de-activatable oligonucleotide may fragment the oligonucleotide rendering it unable to substantially interfere with subsequent elongation reactions or other nucleic acid production steps. Non-limiting examples include visible light, ultraviolet light, infrared (i.e., heat), and the like. In some instances, the temperature of a reaction mixture may be modulated, e.g., such as by the application of heat, to provide sufficient stimulus to modify the activity of a modifiable oligonucleotide, activating an activatable oligonucleotide and/or deactivating a de-activatable oligonucleotide.

As summarized above, the subject stimulus is employed to activate an activatable oligonucleotide and/or deactivate a de-activatable oligonucleotide, respectively, including e.g., through the cleavage of one or more selectively cleavable linkages present in the oligonucleotides.

The term "oligonucleotide" is used herein in its broad sense to refer to single stranded polynucleotides of DNA nucleotides, RNA nucleotides, combinations thereof, and, in some instances, synthetic and/or modified nucleotides, including e.g., synthetic nucleotide analogs, including DNA and RNA analogs. Oligonucleotides of the present methods include those polynucleotides useful in template-mediated extension/elongation reactions, including oligonucleotide primers and those that may serve non-primer functions, such as e.g., template-switching functions.

The term "primer" is used broadly herein and refers to essentially any single-stranded polynucleotide that may be elongated/extended in a reaction to generate any (e.g., initial, intermediate or final) single or multi-stranded polynucleotide through one or more template-mediated extension/elongation reactions. In some instances, primers may have secondary and/or tertiary structure, or may be double-stranded over part of its length. As a non-limiting example, a primer may have secondary and/or tertiary structure in the form of one or more stem loop structure(s). Secondary and tertiary structure(s) may be configured according to any convenient means, including e.g., through the inclusion of one or more self-hybridizing regions within the primer. Primers may be configured with essentially any secondary or tertiary structure where desired, however the region of the primer that hybridizes with a target nucleic acid will, when resolved, generally lack substantial secondary and/or tertiary structure, e.g., be single-stranded, non-self-hybridizing, etc. As described herein, primers useful in the subject methods may be made essentially or primarily of DNA (i.e., may be "DNA-based"), essentially or primarily of RNA (i.e., may be "RNA based"), or some combination (i.e., hybrid) of DNA and RNA. The subject primers may include or exclude synthetic (i.e., non-naturally occurring) nucleotide or nucleoside analogs. Non-limiting examples of nucleotide or nucleoside analogs may include 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine), N8-(7-deaza-8-aza-adenine), peptide nucleic acid, locked nucleic acid, or derivates thereof.

Oligonucleotides and primers of the subject methods may vary in overall length and may range from 15 nt to 150 nt or more, including but not limited to e.g., 15 nt to 150 nt, 15 nt to 140 nt, 15 nt to 130 nt, 15 nt to 120 nt, 15 nt to 110 nt, 15 nt to 100 nt, 15 nt to 90 nt, 15 nt to 80 nt, 15 nt to 70 nt, 15 nt to 60 nt, 15 nt to 50 nt, 15 nt to 40 nt, 15 nt to 30 nt, 18 nt to 150 nt, 18 nt to 140 nt, 18 nt to 130 nt, 18 nt to 120 nt, 18 nt to 110 nt, 18 nt to 100 nt, 18 nt to 90 nt, 18 nt to 80 nt, 18 nt to 70 nt, 18 nt to 60 nt, 18 nt to 50 nt, 18 nt to 40 nt, 18 nt to 30 nt, 20 nt to 150 nt, 20 nt to 140 nt, 20 nt to 130 nt, 20 nt to 120 nt, 20 nt to 110 nt, 20 nt to 100 nt, 20 nt to 90 nt, 20 nt to 80 nt, 20 nt to 70 nt, 20 nt to 60 nt, 20 nt to 50 nt, 20 nt to 40 nt, 20 nt to 30 nt, 25 nt to 150 nt, 25 nt to 140 nt, 25 nt to 130 nt, 25 nt to 120 nt, 25 nt to 110 nt, 25 nt to 100 nt, 25 nt to 90 nt, 25 nt to 80 nt, 25 nt to 70 nt, 25 nt to 60 nt, 25 nt to 50 nt, 25 nt to 40 nt, 25 nt to 30 nt, 30 nt to 150 nt, 30 nt to 140 nt, 30 nt to 130 nt, 30 nt to 120 nt, 30 nt to 110 nt, 30 nt to 100 nt, 30 nt to 90 nt, 30 nt to 80 nt, 30 nt to 70 nt, 30 nt to 60 nt, 30 nt to 50 nt, 30 nt to 40 nt, 40 nt to 150 nt, 40 nt to 140 nt, 40 nt to 130 nt, 40 nt to 120 nt, 40 nt to 110 nt, 40 nt to 100 nt, 40 nt to 90 nt, 40 nt to 80 nt, 40 nt to 70 nt, 40 nt to 60 nt, 40 nt to 50 nt, 50 nt to 150 nt, 50 nt to 140 nt, 50 nt to 130 nt, 50 nt to 120 nt, 50 nt to 110 nt, 50 nt to 100 nt, 50 nt to 90 nt, 50 nt to 80 nt, 50 nt to 70 nt, 50 nt to 60 nt, and the like. Non-limiting examples of useful oligonucleotides, include but are not limited to e.g., template switching oligonucleotides, RT-PCR primers (i.e., one or more primers used in an RT-PCR reaction, e.g., a first strand synthesis primer (e.g., a random primer, an oligo-dT primer, etc.), a second strand synthesis primer, a PCR amplification primer, etc.), amplification primers (e.g., one or more PCR amplification primers), sequence specific primers, sequencing adapter-containing primers, barcode-containing primers, UMI-containing primers, etc. As such, useful oligonucleotides may include essentially any useful nucleic acid domain, or combination thereof. For example, oligonucleotides may include a hybridization domain (e.g., a target hybridization domain, a non-templated hybridization domain, etc.), a sequencing adapter (i.e., "adapter sequence") domain, an indexing domain, a barcode domain, a UMI domain, and the like. One or more useful domains may be included in a subject oligonucleotide for various purposes within a reaction or workflow including but not limited to e.g., to facilitate elongation, to facilitate amplification (e.g., to facilitate amplifying a nucleic acid added to or produced during one or more reaction steps), to facilitate sequencing, to facilitate multiplexing, etc.

Individual domains of the oligonucleotides and primers of the subject methods may vary in overall length and may range from 15 nt to 150 nt or more, including but not limited to e.g., 15 nt to 150 nt, 15 nt to 140 nt, 15 nt to 130 nt, 15 nt to 120 nt, 15 nt to 110 nt, 15 nt to 100 nt, 15 nt to 90 nt, 15 nt to 80 nt, 15 nt to 70 nt, 15 nt to 60 nt, 15 nt to 50 nt, 15 nt to 40 nt, 15 nt to 30 nt, 18 nt to 150 nt, 18 nt to 140 nt, 18 nt to 130 nt, 18 nt to 120 nt, 18 nt to 110 nt, 18 nt to 100 nt, 18 nt to 90 nt, 18 nt to 80 nt, 18 nt to 70 nt, 18 nt to 60 nt, 18 nt to 50 nt, 18 nt to 40 nt, 18 nt to 30 nt, 20 nt to 150 nt, 20 nt to 140 nt, 20 nt to 130 nt, 20 nt to 120 nt, 20 nt to 110 nt, 20 nt to 100 nt, 20 nt to 90 nt, 20 nt to 80 nt, 20 nt to 70 nt, 20 nt to 60 nt, 20 nt to 50 nt, 20 nt to 40 nt, 20 nt to 30 nt, 25 nt to 150 nt, 25 nt to 140 nt, 25 nt to 130 nt, 25 nt to 120 nt, 25 nt to 110 nt, 25 nt to 100 nt, 25 nt to 90 nt, 25 nt to 80 nt, 25 nt to 70 nt, 25 nt to 60 nt, 25 nt to 50 nt, 25 nt to 40 nt, 25 nt to 30 nt, 30 nt to 150 nt, 30 nt to 140 nt, 30 nt to 130 nt, 30 nt to 120 nt, 30 nt to 110 nt, 30 nt to 100 nt, 30 nt to 90 nt, 30 nt to 80 nt, 30 nt to 70 nt, 30 nt to 60 nt, 30 nt to 50 nt, 30 nt to 40 nt, 40 nt to 150 nt, 40 nt to 140 nt, 40 nt to 130 nt, 40 nt to 120 nt, 40 nt to 110 nt, 40 nt to 100 nt, 40 nt to 90 nt, 40 nt to 80 nt, 40 nt to 70 nt, 40 nt to 60 nt, 40 nt to 50 nt, 50 nt to 150 nt, 50 nt to 140 nt, 50 nt to 130 nt, 50 nt to 120 nt, 50 nt to 110 nt, 50 nt to 100 nt, 50 nt to 90 nt, 50 nt to 80 nt, 50 nt to 70 nt, 50 nt to 60 nt, and the like.

As summarized above, activatable and de-activatable oligonucleotides of the present methods may be activatable and de-activatable through the cleavage of specifically cleavable nucleotide linkages present in the oligonucleotides. For example, a de-activatable oligonucleotide may include one or more cleavable nucleotide linkages that, when cleaved through the application of a stimulus, destroy the pre-cleavage function of the de-activatable oligonucleotide or otherwise significantly reduce the ability of the de-activatable oligonucleotide to perform its pre-cleavage function.

In some embodiments, a de-activatable oligonucleotide may hybridize, in whole or in part, to a target nucleic acid with a particular Tm, including but not limited to e.g., a Tm greater than 50° C., including e.g., greater than 55° C., greater than 60° C., greater than 65° C., greater than 70° C., and the like. Under suitable reaction conditions, the hybridized de-activatable oligonucleotide may, e.g., serve as a primer and be elongated in an elongation reaction templated by the target nucleic acid to which the de-activatable oligonucleotide is hybridized.

At some point following performance of the reaction step for which the de-activatable oligonucleotide is employed, a stimulus may be applied to the reaction mixture, deactivating the de-activatable oligonucleotide through cleavage of one or more cleavable linkages in the de-activatable oligonucleotide. Following cleavage by the stimulus, the generated cleavage fragments of the de-activatable oligonucleotide may then each have Tm's insufficient for any significant hybridization with reaction components in the reaction mixture at reaction conditions under which subsequent reactions are performed. In some instances, the Tm of one or more fragments, including all fragments, of a deactivatable de-activatable oligonucleotide may be 50° C. or less, including but not limited to e.g., 50° C. or less, 49° C. or less, 48° C. or less, 47° C. or less, 46° C. or less, 45° C. or less, 44° C. or less, 43° C. or less, 42° C. or less, 41° C. or less, 40° C. or less, 39° C. or less, 38° C. or less, 37° C. or less, 36° C. or less, 35° C. or less, 34° C. or less, 33° C. or less, 32° C. or less, 31° C. or less, 30° C. or less, 29° C. or less, 28° C. or less, 27° C. or less, 26° C. or less, 25° C. or less, 24° C. or less, 23° C. or less, 22° C. or less, 21° C. or less, 20° C. or less, 19° C. or less, 18° C. or less, 17° C. or less, 16° C. or less, 15° C. or less, 14° C. or less, 13° C. or less, 12° C. or less, 11° C. or less, 10° C. or less, 9° C. or less, 8° C. or less, 7° C. or less, 6° C. or less, etc. Tm's, as used herein, may be calculated according to standard methods and under standard reaction conditions.

As will be readily understood, de-activatable oligonucleotides are not limited to those functioning as primers and may include e.g., oligonucleotides that may function as a template, such as e.g., a template-switching oligonucleotide which functions as a template in a template switching reaction. Such de-activatable oligonucleotides, and the fragments thereof, that do not serve a primer function per se may nonetheless be characterized according to a calculated Tm of the oligonucleotide or fragment. For example, a de-activatable template-switching oligonucleotide may have a calculated Tm including but not limited to e.g., greater than 50° C., including e.g., greater than 55° C., greater than 60° C., greater than 65° C., greater than 70° C., and the like.

Fragments of a cleaved de-activatable template switching oligonucleotide may be characterized as, e.g., having a Tm of 40° C. or less and/or any of the relevant Tm ranges described above for fragments of de-activatable oligonucleotides.

The size of fragments generated from the cleavage of a de-activatable oligonucleotide will also vary and may range, in some instances, from 2 nt to 15 nt or more, including but not limited to e.g., 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 3 nt to 15 nt, 3 nt to 14 nt, 3 nt to 13 nt, 3 nt to 12 nt, 3 nt to 11 nt, 3 nt to 10 nt, 3 nt to 9 nt, 3 nt to 8 nt, 3 nt to 7 nt, 3 nt to 6 nt, 3 nt to 5 nt, 4 nt to 15 nt, 4 nt to 14 nt, 4 nt to 13 nt, 4 nt to 12 nt, 4 nt to 11 nt, 4 nt to 10 nt, 4 nt to 9 nt, 4 nt to 8 nt, 4 nt to 7 nt, 4 nt to 6 nt, 5 nt to 15 nt, 5 nt to 14 nt, 5 nt to 13 nt, 5 nt to 12 nt, 5 nt to 11 nt, 5 nt to 10 nt, 5 nt to 9 nt, 5 nt to 8 nt, 5 nt to 7 nt, 6 nt to 15 nt, 6 nt to 14 nt, 6 nt to 13 nt, 6 nt to 12 nt, 6 nt to 11 nt, 6 nt to 10 nt, 6 nt to 9 nt, 6 nt to 8 nt, 7 nt to 15 nt, 7 nt to 14 nt, 7 nt to 13 nt, 7 nt to 12 nt, 7 nt to 11 nt, 7 nt to 10 nt, 7 nt to 9 nt, 8 nt to 15 nt, 8 nt to 14 nt, 8 nt to 13 nt, 8 nt to 12 nt, 8 nt to 11 nt, 8 nt to 10 nt, etc.

Where a de-activatable oligonucleotide is deactivated by cleavage into multiple fragments, the number of produced fragments will vary and may range from 2 to 50 or more, including but not limited to e.g., 2 to 50, 3 to 50, 4 to 50, 5 to 50, 6 to 50, 7 to 50, 8 to 50, 9 to 50, 10 to 50, 2 to 25, 3 to 25, 4 to 25, 5 to 25, 6 to 25, 7 to 25, 8 to 25, 9 to 25, 10 to 25, 2 to 10, 3 to 10, 4 to 10, 5 to 10, 6 to 10, 7 to 10, etc. The number of fragments generated may depend on various factors including the particular design of the de-activatable oligonucleotide including its overall length and the presence (e.g., position and number) of cleavage linkages therein.

Activatable oligonucleotides may, in some embodiments, include a resolvable moiety that, when resolved by the application of a stimulus to the activatable oligonucleotide, allows the active activatable oligonucleotide to serve its primary function in the reaction. Such resolvable moieties may be essentially any removable nucleic acid modification, removable by a stimulus, or nucleic acid tertiary structure, resolvable by a stimulus, that prevents the activatable oligonucleotide from performing its primary function. In some instances, a removable moiety, e.g., a blocking moiety, may be removable through the cleavage of one or more specifically cleavable nucleotide linkages present in the activatable oligonucleotide. In some instances, a resolvable moiety, e.g., an inhibitory tertiary structure, may be resolvable through the cleavage of one or more specifically cleavable nucleotide linkages present in the activatable oligonucleotide. Useful resolvable/removable moieties are described in more detail below.

An embodiment of a nucleic acid production process using activatable and de-activatable oligonucleotides responsive to different stimuli is schematically depicted in FIG. 1A. As depicted, the reaction components are combined in a reaction mixture 100, containing a de-activatable oligonucleotide 101, an activatable oligonucleotide 102 and a template nucleic acid 103, which in this example is depicted as an mRNA although the methods of the present disclosure are not so limited. After combining the reaction components, the de-activatable oligonucleotide is annealed to its target site, in this case the poly-A tail of the mRNA template 104, and the de-activatable oligonucleotide is elongated, depicted as a dotted line 105, by reverse transcriptase. The activatable oligonucleotide contains a resolvable/removable moiety 106 that prevents the interaction of the activatable oligonucleotide with components of the reverse transcription reaction 107. At some point after the production of the reverse transcribed first strand nucleic acid, a first stimulus is applied 108 to the reaction. Application of the first stimulus cleaves the de-activatable oligonucleotide, generating cleavage fragments 110. Application of a second stimulus 113, applied either simultaneously with the first stimulus 108 or sequentially sometime after the first stimulus 108, resolves/removes the resolvable/removable moiety activating the activatable oligonucleotide. The activated activatable oligonucleotide 109, in this instance serves as a primer and hybridizes to a site in a nucleic acid 111 produced during the reaction. The activated activatable oligonucleotide is elongated, depicted as a dotted line 112, by a polymerase. This reaction may generate a product nucleic acid either from the elongation product of the activated activatable oligonucleotide or through subsequent nucleic acid reaction steps (e.g., amplification).

An embodiment of a nucleic acid production process using activatable and de-activatable oligonucleotides responsive to the same stimulus is schematically depicted in FIG. 1B. As depicted, the reaction components are combined in a reaction mixture 100, containing a de-activatable oligonucleotide 101, an activatable oligonucleotide 102 and a template nucleic acid 103, which in this example is depicted as an mRNA although the methods of the present disclosure are not so limited. After combining the reaction components, the de-activatable oligonucleotide is annealed to its target site, in this case the poly-A tail of the mRNA template 104, and the de-activatable oligonucleotide is elongated, depicted as a dotted line 105, by reverse transcriptase. The activatable oligonucleotide contains a resolvable/removable moiety 106 that prevents the interaction of the activatable oligonucleotide with components of the reverse transcription reaction 107. At some point after the production of the reverse transcribed first strand nucleic acid, the stimulus is applied 114 to the reaction. Application of the stimulus resolves/removes the resolvable/removable moiety activating the activatable oligonucleotide and cleaving the de-activatable oligonucleotide, generating cleavage fragments 110. The activated activatable oligonucleotide 109, in this instance serves as a primer and hybridizes to a site in a nucleic acid 111 produced during the reaction. The activated activatable oligonucleotide is elongated, depicted as a dotted line 112, by a polymerase. This reaction may generate a product nucleic acid either from the elongation product of the activated activatable oligonucleotide or through subsequent nucleic acid reaction steps (e.g., amplification).

Figure 1C:
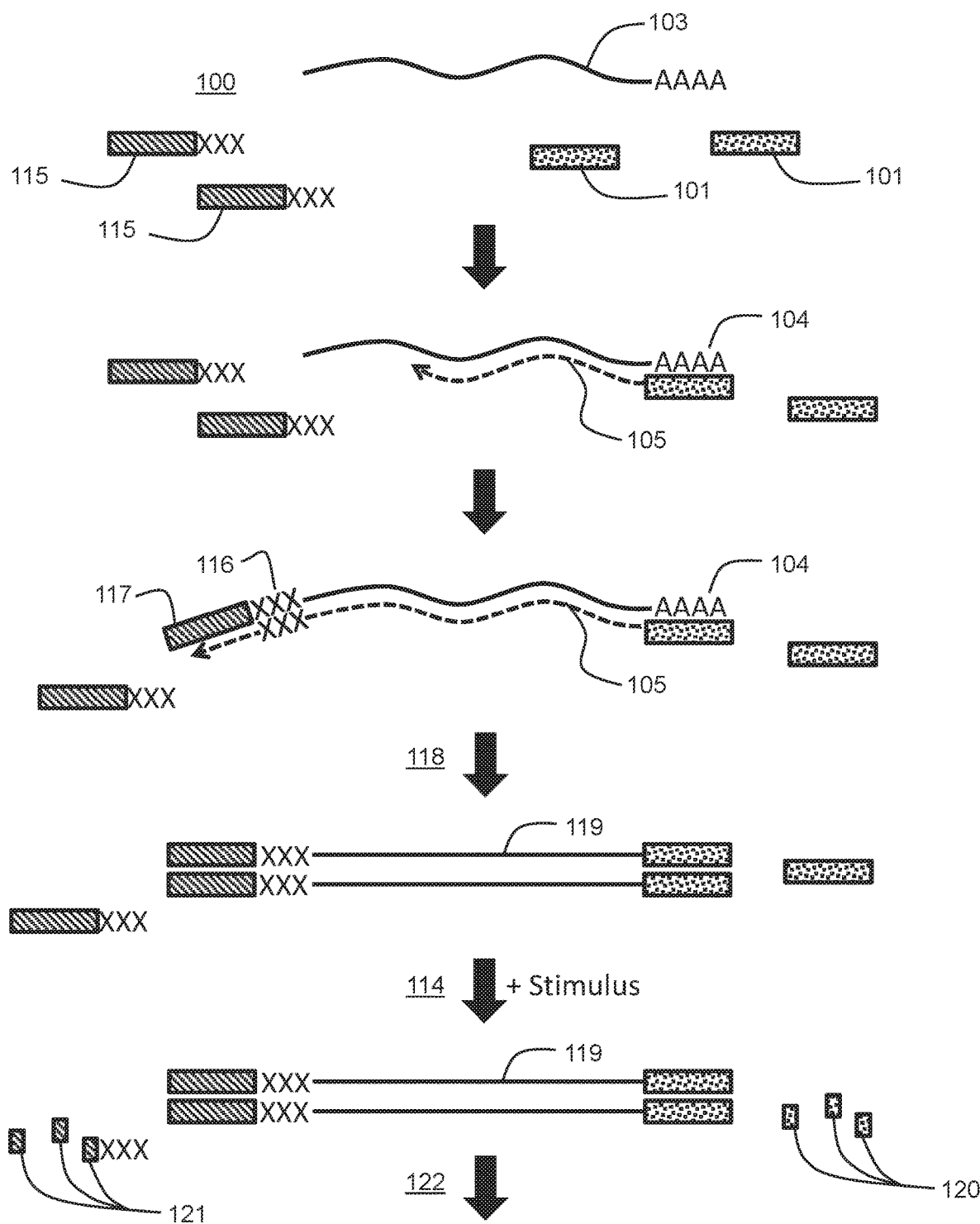

An embodiment of a nucleic acid production process using two different types of de-activatable oligonucleotides responsive to the same stimulus is schematically depicted in FIG. 1C. As depicted, the reaction components are combined in a reaction mixture 100, containing a first type of de-activatable oligonucleotide 101, a second type of de-activatable oligonucleotide 115 and a template nucleic acid 103, which in this example is depicted as an mRNA although the methods of the present disclosure are not so limited. After combining the reaction components, the first de-activatable oligonucleotide 101 is annealed to its target site, in this case the poly-A tail of the mRNA template 104, and the first de-activatable oligonucleotide is elongated, depicted as a dotted line 105, by reverse transcriptase. The second de-activatable oligonucleotide 115 in this example is a template switching oligonucleotide that contains a 3' hybridization domain 116 and a 5' region 117 that serves as a template for the elongating strand 105. Amplification 118 of the elongated strand with a DNA polymerase results in a double-stranded DNA molecule 119. Such amplification may employ the template switching oligonucleotide as an amplification primer and/or may employ one or more amplification primers that is/are not the template switching oligonucleotide (i.e., the template switching oligonucleotide may or may not be employed as an amplification primer). The double stranded DNA molecule may contain at its 5' and/or 3' ends replicated copies, and the complement(s) thereof, of the first and/or second de-activatable oligonucleotide sequences, including any 5' untemplated sequence originally present on the first and/or second de-activatable oligonucleotides. At some point after the production of the double stranded DNA molecule 119, a stimulus is applied 114 to the reaction. The applied stimulus cleaves the first and second de-activatable oligonucleotides, generating first de-activatable oligonucleotide cleavage fragments 120 and second de-activatable oligonucleotide cleavage fragments 121. Depending on the context and the stimulus employed, the first and/or second de-activatable oligonucleotides may be deactivated in their free (i.e., unhybridized) state, in their hybridized state, or both. For example, where a nuclease is employed as the stimulus that specifically hydrolyzes the phosphodiester bonds of RNA when hybridized to DNA and the first and second de-activatable oligonucleotides contain RNA nucleotides, the first and second de-activatable oligonucleotides may be de-activated upon hybridizing with DNA, such as the produced double stranded DNA molecule. The produced double-stranded DNA molecule 119 may be utilized in one or more subsequent reaction steps 122 where the continued presence of active de-activatable oligonucleotides would, if not deactivated, interfere with the production of a desired product nucleic acid.

Figure 1D:
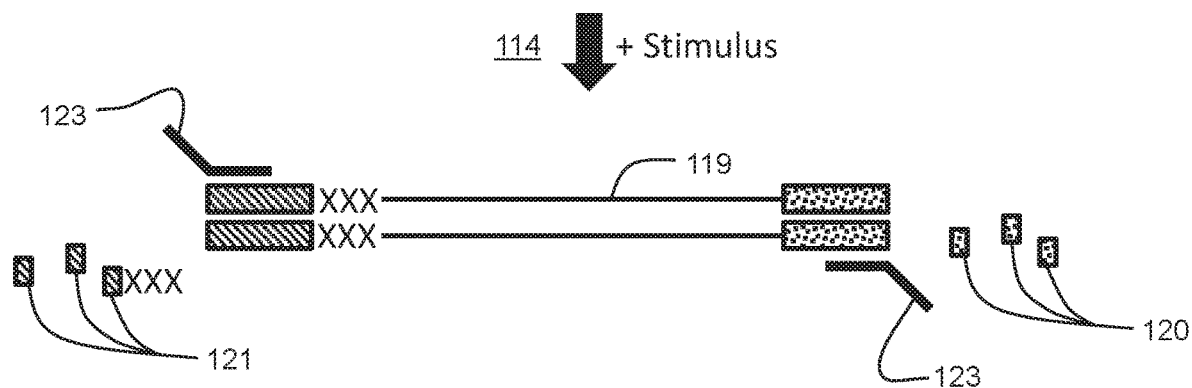
Figure 1E:
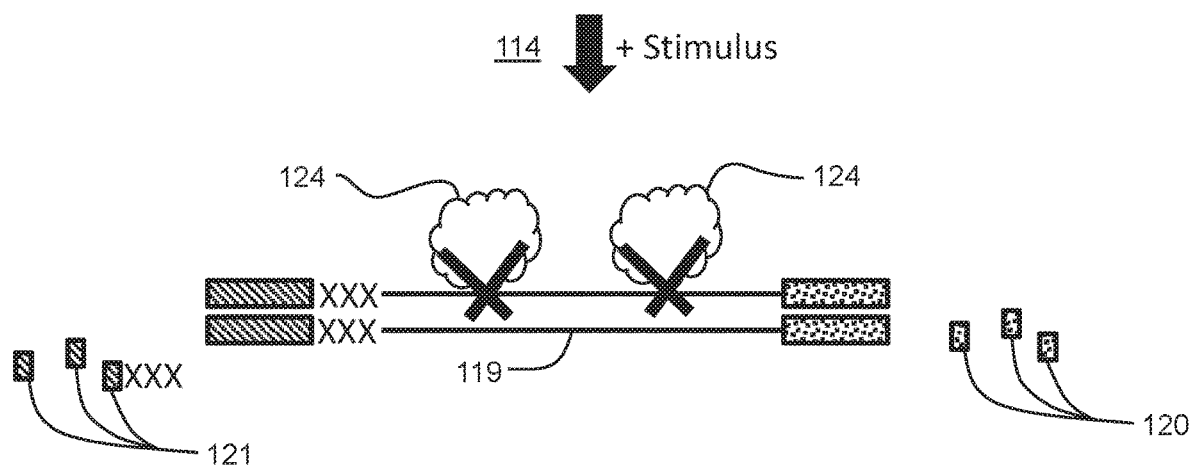

Alternatively, the produced double-stranded DNA molecule may be utilized in a reaction to produce a desired product nucleic acid during (i.e., concurrent with) the application of the stimulus, e.g., by including reaction components (e.g., additional primers, polymerase, etc.) necessary to produce the desired product nucleic acid in the reaction mixture to which the stimulus is applied. For example, as depicted in FIG. 1D, the first and second de-activatable oligonucleotides may be degraded to produce fragments 120 and 121 by the applied stimulus 114 during an amplification reaction with one or more additional primers 123. The one or more additional primers may, in some instances, include a non-hybridizing domain or a non-templated sequence, such as but not limited to e.g., a primer binding site, an index or adapter sequence, a barcode sequence, etc. As another example, as depicted in FIG. 1E, the first and second de-activatable oligonucleotides may be degraded to produce fragments 120 and 121 by the applied stimulus 114 during a tagmentation reaction employing tagmentation reaction components 124. Tagmentation may, in some instances, be employed to add one or more non-templated sequences, such as but not limited to e.g., a primer binding site, an index or adapter sequence, a barcode sequence, etc. In some instances, one or more desired non-templated sequences, such as but not limited to e.g., a primer binding site, an index or adapter sequence, a barcode sequence, etc., may be added following tagmentation, e.g., in an amplification reaction performed following tagmentation.

Figure 2:
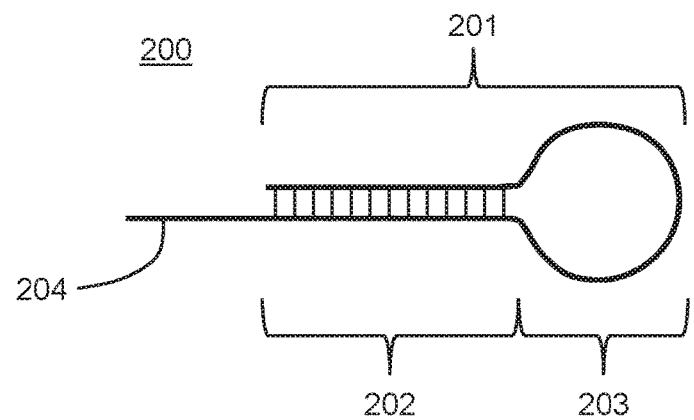
FIG. 2 provides a schematic depiction of one embodiment of an activatable oligonucleotide having a stem-loop structure.

As summarized above, any convenient resolvable/removable moiety may be employed in the activatable primers of the present methods. As an example, in some instances, a resolvable moiety may be generated in an activatable oligonucleotide through the formation of a secondary and/or tertiary structure that prevents one or more functions of the activatable oligonucleotide, e.g., hybridization, extension, etc. In some embodiments, useful nucleic acid secondary and/or tertiary structures in activatable oligonucleotides will include stem-loop structures. Stem-loop structures may be formed by the presence of two sections of hybridizing sequence present in an oligonucleotide (i.e., self-hybridizing sequence). For example, as depicted in FIG. 2, an activatable primer 200 may include a stem-loop region 201 that includes a self-hybridizing stem region 202 and an unpaired loop region 203. Such oligonucleotides may or may not include one or more regions of unpaired nucleotides 204 that is/are separate from the stem-loop region and 5' and/or 3' of the self-hybridizing stem region.

The overall size of the stem-loop region, as defined by the number of nucleotides included in the region, may vary and may range from 14 nt or less to 100 nt or more, including but not limited to e.g., 14 nt to 100 nt, 15 nt to 100 nt, 16 nt to 100 nt, 17 nt to 100 nt, 18 nt to 100 nt, 19 nt to 100 nt, 20 nt to 100 nt, 21 nt to 100 nt, 22 nt to 100 nt, 23 nt to 100 nt, 24 nt to 100 nt, 25 nt to 100 nt, 30 nt to 100 nt, 35 nt to 100 nt, 40 nt to 100 nt, 45 nt to 100 nt, 50 nt to 100 nt, 55 nt to 100 nt, 60 nt to 100 nt, 65 nt to 100 nt, 70 nt to 100 nt, 75 nt to 100 nt, 14 nt to 90 nt, 15 nt to 90 nt, 16 nt to 90 nt, 17 nt to 90 nt, 18 nt to 90 nt, 19 nt to 90 nt, 20 nt to 90 nt, 21 nt to 90 nt, 22 nt to 90 nt, 23 nt to 90 nt, 24 nt to 90 nt, 25 nt to 90 nt, 30 nt to 90 nt, 35 nt to 90 nt, 40 nt to 90 nt, 45 nt to 90 nt, 50 nt to 90 nt, 55 nt to 90 nt, 60 nt to 90 nt, 65 nt to 90 nt, 70 nt to 90 nt, 14 nt to 80 nt, 15 nt to 80 nt, 16 nt to 80 nt, 17 nt to 80 nt, 18 nt to 80 nt, 19 nt to 80 nt, 20 nt to 80 nt, 21 nt to 80 nt, 22 nt to 80 nt, 23 nt to 80 nt, 24 nt to 80 nt, 25 nt to 80 nt, 30 nt to 80 nt, 35 nt to 80 nt, 40 nt to 80 nt, 45 nt to 80 nt, 50 nt to 80 nt, 55 nt to 80 nt, 60 nt to 80 nt, 65 nt to 80 nt, 70 nt to 80 nt, etc.

The size of the various regions of a stem-loop structure may similarly vary. For example, in some instances, the self-hybridizing region may range, e.g., from 10 nt or less to 50 nt or more including but not limited to e.g., 10 nt to 50 nt, 10 nt to 45 nt, 10 nt to 40 nt, 10 nt to 35 nt, 10 nt to 30 nt, 10 nt to 25 nt, 10 nt to 20 nt, 12 nt to 50 nt, 12 nt to 45 nt, 12 nt to 40 nt, 12 nt to 35 nt, 12 nt to 30 nt, 12 nt to 25 nt, 14 nt to 50 nt, 14 nt to 45 nt, 14 nt to 40 nt, 14 nt to 35 nt, 14 nt to 30 nt, 14 nt to 25 nt, 16 nt to 50 nt, 16 nt to 45 nt, 16 nt to 40 nt, 16 nt to 35 nt, 16 nt to 30 nt, 16 nt to 25 nt, 18 nt to 50 nt, 18 nt to 45 nt, 18 nt to 40 nt, 18 nt to 35 nt, 18 nt to 30 nt, 18 nt to 25 nt, 20 nt to 50 nt, 20 nt to 45 nt, 20 nt to 40 nt, 20 nt to 35 nt, 20 nt to 30 nt, 20 nt to 25 nt, etc.

In some instances, the unpaired loop region may range, e.g., from 4 nt to 30 nt or more including but not limited to e.g., 4 nt to 30 nt, 4 nt to 28 nt, 4 nt to 26 nt, 4 nt to 24 nt, 4 nt to 22 nt, 4 nt to 20 nt, 4 nt to 18 nt, 4 nt to 16 nt, 4 nt to 14 nt, 4 nt to 12 nt, 4 nt to 10 nt, 4 nt to 8 nt, 6 nt to 30 nt, 6 nt to 28 nt, 6 nt to 26 nt, 6 nt to 24 nt, 6 nt to 22 nt, 6 nt to 20 nt, 6 nt to 18 nt, 6 nt to 16 nt, 6 nt to 14 nt, 6 nt to 12 nt, 6 nt to 10 nt, 8 nt to 30 nt, 8 nt to 28 nt, 8 nt to 26 nt, 8 nt to 24 nt, 8 nt to 22 nt, 8 nt to 20 nt, 8 nt to 18 nt, 8 nt to 16 nt, 8 nt to 14 nt, 8 nt to 12 nt, 10 nt to 30 nt, 10 nt to 28 nt, 10 nt to 26 nt, 10 nt to 24 nt, 10 nt to 22 nt, 10 nt to 20 nt, 10 nt to 18 nt, 10 nt to 16 nt, 15 nt to 30 nt, 15 nt to 28 nt, 15 nt to 26 nt, 15 nt to 24 nt, 15 nt to 22 nt, 15 nt to 20 nt, 20 nt to 30 nt, 20 nt to 28 nt, 20 nt to 26 nt, 20 nt to 24 nt, etc.

A stem-loop structure present in an activatable oligonucleotide may be resolvable through cleavage of one or more cleavable nucleotide linkages present in the step-loop region. The position of such cleavable nucleotide linkages may vary and may include where such linkages are present in the self-hybridizing stem region, the unpaired loop region or both. For example, in some instances, an activatable oligonucleotide may include one or more cleavable nucleotide linkages in the self-hybridizing stem region such that, upon application of the stimulus, the linkages are cleaved resolving the stem-loop structure. In some instances, where cleavable nucleotide linkages are present in the self-hybridizing stem region, such linkages may be only present in one of the two hybridizing regions. For example, in some instances, only the self-hybridizing stem region that is 3' of the unpaired loop region may contain cleavable linkages. In some instances, only the self-hybridizing stem region that is 5' of the unpaired loop region may contain cleavable linkages.

Cleavage of one or more cleavable linkages present in an activatable oligonucleotide may generate two or more fragments from the activatable oligonucleotide. Where such cleavage events are employed, the generated fragments will contain at least a primary fragment that represents the activated oligonucleotide and at least one other minor fragment that is not involved in and does not substantially interfere with downstream processes. The generated primary fragment will have functional characteristics necessary for its use in the desired step of the nucleic acid production process, including e.g., a Tm sufficient for hybridization to a target hybridization site within a target nucleic acid (e.g., a template nucleic acid).

Following cleavage, generated minor fragments of the activatable oligonucleotide may each have Tm's insufficient for any significant hybridization with reaction components in the reaction mixture under subsequent reaction conditions. In some instances, the Tm of one or more minor fragments, including all minor fragments, of an activated activatable oligonucleotide may be 50° C. or less, including but not limited to e.g., 50° C. or less, 49° C. or less, 48° C. or less, 47° C. or less, 46° C. or less, 45° C. or less, 44° C. or less, 43° C. or less, 42° C. or less, 41° C. or less, 40° C. or less, 39° C. or less, 38° C. or less, 37° C. or less, 36° C. or less, 35° C. or less, 34° C. or less, 33° C. or less, 32° C. or less, 31° C. or less, 30° C. or less, 29° C. or less, 28° C. or less, 27° C. or less, 26° C. or less, 25° C. or less, 24° C. or less, 23° C. or less, 22° C. or less, 21° C. or less, 20° C. or less, 19° C. or less, 18° C. or less, 17° C. or less, 16° C. or less, 15° C. or less, 14° C. or less, 13° C. or less, 12° C. or less, 11° C. or less, 10° C. or less, 9° C. or less, 8° C. or less, 7° C. or less, 6° C. or less, etc. Tm's, as used herein, may be calculated according to standard methods and under standard reaction conditions.

In some instances, the size of the generated minor fragments may also vary and may range, in some instances, from 2 nt to 15 nt or more, including but not limited to e.g., 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 3 nt to 15 nt, 3 nt to 14 nt, 3 nt to 13 nt, 3 nt to 12 nt, 3 nt to 11 nt, 3 nt to 10 nt, 3 nt to 9 nt, 3 nt to 8 nt, 3 nt to 7 nt, 3 nt to 6 nt, 3 nt to 5 nt, 4 nt to 15 nt, 4 nt to 14 nt, 4 nt to 13 nt, 4 nt to 12 nt, 4 nt to 11 nt, 4 nt to 10 nt, 4 nt to 9 nt, 4 nt to 8 nt, 4 nt to 7 nt, 4 nt to 6 nt, 5 nt to 15 nt, 5 nt to 14 nt, 5 nt to 13 nt, 5 nt to 12 nt, 5 nt to 11 nt, 5 nt to 10 nt, 5 nt to 9 nt, 5 nt to 8 nt, 5 nt to 7 nt, 6 nt to 15 nt, 6 nt to 14 nt, 6 nt to 13 nt, 6 nt to 12 nt, 6 nt to 11 nt, 6 nt to 10 nt, 6 nt to 9 nt, 6 nt to 8 nt, 7 nt to 15 nt, 7 nt to 14 nt, 7 nt to 13 nt, 7 nt to 12 nt, 7 nt to 11 nt, 7 nt to 10 nt, 7 nt to 9 nt, 8 nt to 15 nt, 8 nt to 14 nt, 8 nt to 13 nt, 8 nt to 12 nt, 8 nt to 11 nt, 8 nt to 10 nt, etc.

Where an activatable oligonucleotide is activated by cleavage resulting in multiple minor fragments, the number of produced minor fragments will vary and may range from 2 to 50 or more, including but not limited to e.g., 2 to 50, 3 to 50, 4 to 50, 5 to 50, 6 to 50, 7 to 50, 8 to 50, 9 to 50, 10 to 50, 2 to 25, 3 to 25, 4 to 25, 5 to 25, 6 to 25, 7 to 25, 8 to 25, 9 to 25, 10 to 25, 2 to 10, 3 to 10, 4 to 10, 5 to 10, 6 to 10, 7 to 10, etc. The number of fragments generated may depend on various factors including the particular design of the activatable oligonucleotide including its overall length, the presence (e.g., position and number) of cleavable linkages therein, the structure of a stem-loop region if present, and the like.

Cleavable nucleotide linkages, also referred to with reference to a "cleavable-base", useful in the oligonucleotides of the present methods will vary. A cleavable-base refers to a nucleotide that includes at least one attached cleavable-internucleotide (e.g., phosphodiester or alternative) nucleotide linkage. Cleavable-bases, as used herein, will generally not refer to, except where indicated otherwise, nucleotides where the base (e.g., purine base or pyrimidine base) is cleaved away from the backbone, but instead to where a backbone linkage is cleaved severing the nucleic acid strand containing the cleavable-base. However, in some instances, an enzyme or a mixture of enzymes that generate an abasic site from a cleavable-base and subsequently cleave an internucleotide linkage of the abasic site may be employed.

The number of cleavable-bases present in a subject oligonucleotide may vary and may range from 1 to 20 or more including but not limited to e.g., 1 to 20, 1 to 15, 1 to 10, 1 to 5, 2 to 20, 2 to 15, 2 to 10, 2 to 5, 3 to 20, 3 to 15, 3 to 10, 3 to 5, 4 to 20, 4 to 15, 4 to 10, 5 to 20, 5 to 15, 5 to 10, 10 to 15, 10 to 20, etc. The arrangement of cleavable-bases within an oligonucleotide may also vary and may include where two cleavable bases are or are not adjacent. For example, in some instances, two cleavable bases may be separated by one or more intervening nucleotides (i.e., non-cleavable bases, including e.g., natural or synthetic nucleic acids, including deoxyribonucleotides), where the number of intervening nucleotides may vary and may range from 1 to 30 or more, including but not limited to e.g., 1 to 30, 1 to 25, 1 to 20, 1 to 15, 1 to 10, 1 to 5, 2 to 30, 2 to 25, 2 to 20, 2 to 15, 2 to 10, 2 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, 25 to 30, etc.

Useful cleavable nucleotide linkages, e.g., between a cleavable-base and a neighboring nucleotide, include enzymatically cleavable linkages, chemically cleavable linkages and electromagnetically cleavable linkages. Enzymatically cleavable linkages include those linkages that are specifically cleavable by a nuclease. For example, useful cleavable linkages include phosphodiester bonds of RNA, e.g., present in RNA:DNA duplexes that are specifically cleavable by ribonuclease H. Useful enzymatically cleavable linkages may also include internucleotide linkages adjacent to an abasic site (i.e., an apurinic/apyrimidinic (AP) site), e.g., as generated by a glycosylase, such as but not limited to e.g., a uracil DNA glycosylase (UDG), MutY glycosylase, modified versions thereof and the like. Useful glycosylases may include monofunctional DNA glycosylases that cleave the glycosidic bond between the target base and the deoxyribose to generate an AP site as well as bifunctional DNA glycosylases/AP lyases which generate an AP site intermediate and cleave the phosphodiester bond adjacent to the target base. Various nucleases may be employed to cleave internucleotide linkages at abasic sites, e.g., where a monofunctional DNA glycosylase is employed to generate the abasic site, including but not limited to e.g., AP endonucleases such as e.g., endonuclease IV. Useful bifunctional DNA glycosylases/AP lyases may also include those having both glycosylase activity and AP-lyase activity such as, but not limited to e.g., endonuclease III, endonuclease VIII and the like. In some instances, one or more cleavable ribonucleotide bases may be utilized in a DNA oligonucleotide such that, when the ribonucleotide base is hybridized (either inter- or intramolecularly) with a deoxyribonucleotide it is cleavable by the application of a nuclease stimulus, e.g., an RNase H stimulus. In some instances, one or more cleavable deoxyribonucleotide bases (e.g., a deoxyuracil or a derivative thereof, an adenine mismatch, and the like) may be utilized in a DNA oligonucleotide such that it is cleavable by the application of one or more enzymatic stimuli, e.g., a mono- or bifunctional glycosylase such as but not limited to e.g., UDG, MutY glycosylase, endonuclease III, endonuclease VIII, NucS, Polynucleotide Kinase (PNK), etc. (with or without the additional application of a AP endonuclease). For example, NucS can be used to activate or de-activate oligonucleotides with mismatches. In another example, PNK can be used to activate phosphorylated oligonucleotides by dephosphorylating them. Other examples of enzymatically cleavable linkages include those specific nucleotide linkages cleaved by endonucleases, including sequence specific restriction endonucleases, sequence specific nicking endonucleases, and the like. In some instances, activatable and de-activatable oligonucleotides may be designed to include linkages cleavable by the same enzyme, such as glycosylases and/or nucleases, including ribonucleases, such as RNase H, endonucleases, and the like. Useful enzymatically cleavable linkages may vary and are not limited to those specifically described.

In some embodiments, the subject methods may include the use of a DNA-based de-activatable oligonucleotide that includes two or more ribonucleotides separated by at least one deoxyribonucleotide and/or a DNA-based activatable oligonucleotide that includes a stem-loop region that includes a self-hybridizing stem region having two or more ribonucleotides separated by at least one deoxyribonucleotide in one strand of the self-hybridizing stem region. In such embodiments, a ribonuclease, such as RNase H, may be employed to cleave the internucleotide linkages between the ribonucleotides in one or both of the de-activatable oligonucleotide and/or the activatable oligonucleotide thereby deactivating and/or activating, respectively, one or more of the oligonucleotides.

In some instances, chemically cleavable linkages may be employed. Chemically cleavable linkages include those linkages that are specifically cleavable by the addition of a chemical to the reaction mixture. Useful chemically cleavable linkages include those oligonucleotide backbone linkages present in modified nucleotide substituted oligonucleotides. For example, in some instances, specific chemically cleavable linkages may be introduced into a subject oligonucleotide by the introduction of a modified nucleotide having a corresponding chemical that cleaves the incorporated modified nucleotide. Non-limiting examples of such modified nucleotides include 5-hydroxy-dCTP, 5-hydroxy-dUTP, 7-Deaza-7-nitro-dATP, 7-deaza-7-nitro-dGTP and the like. Other chemically cleavable linkages include those phosphodiester linkages that may be targeted using synthetic chemical endonucleases (e.g., EDTA-conjugated oligonucleotides). Useful chemically cleavable linkages may vary and are not limited to those specifically described.

In some instances, electromagnetically cleavable linkages may be employed. Electromagnetically cleavable linkages include those linkages that are specifically cleavable by the application of electromagnetic radiation (e.g., visible light, ultraviolet light, infrared (i.e., heat), etc.) to the reaction mixture. Useful electromagnetically cleavable linkages include e.g., those present in photocleavable linkers based on ortho-nitrobenzyl moieties, those present in bromohydroxyquinoline groups, and the like. In some instances, heat-labile linkages may include one or more phosphodiester bonds of an abasic nucleotide (e.g., abasic sites as generated by a glycosylase, e.g., an N-glycosylases, including, e.g., UDG and the like), as well as those nucleic acid linkages that are relatively heat-labile, such as RNA (e.g., as compared to less heat-labile linkages such as those of DNA). In some instances, heat-stimulated cleavage may be further mediated through the use of basic reaction conditions. In some instances, oligonucleotide moieties activated by heat may also be employed, such as the 4-oxo-1-pentyl (OXP) phosphotriester (PTE) modification groups used on heat activatable primers, including e.g., those described by Lebedev et al. (Nucleic Acids Research, 2008, Vol. 36, No. 20 e131; the disclosure of which is incorporated herein by reference in its entirety).

Useful electromagnetically cleavable linkages include but are not limited to e.g., those photocleavable linkers commercially available and sold by TriLink BioTechnologies, LLC; Integrated DNA Technologies, Inc.; GeneLink™, Glen Research Corporation, and the like. Useful photocleavable linkages also include those described in U.S. Pat. No. 5,430,136 and Liu & Deiters (Acc Chem Res. 2014; 47(1): 45-55); the disclosures of which are incorporated herein by reference in their entirety.

Reaction Mixtures

As summarized above, the herein described methods may include certain nucleic acid reactions, including e.g., elongation/extension reactions, template-switching reactions, reverse transcription reactions, nucleic acid amplification reactions, tagmentation reactions, and the like. The reaction mixture components in such reactions are combined under conditions sufficient to produce the product of the reaction. For example, in some instances, the reaction components of an extension/elongation reaction are combined under conditions sufficient to produce a nucleic acid product, including nucleic acid products that may or may not be used in or subjected to further reaction steps. In some instances, the reaction components of a nucleic acid amplification reaction are combined under conditions sufficient to produce an amplified product nucleic acid. Reaction components of a tagmentation reaction are combined under conditions sufficient to produce a tagmented nucleic acid, which may or may not be used in or subjected to subsequent reaction steps.

Components may be combined into a reaction mixture in any suitable reaction vessel, including but not limited to e.g., tubes, wells of a multi-well plate, droplets, etc. In some instances, a single reaction vessel may be employed, including e.g., where multiple, including all, reaction steps are performed in a single reaction vessel. In some instances, reaction mixtures may be prepared in multiplex arrangements, such as e.g., where individual reaction mixtures, which may be the same or different, are prepared in the wells of a multi-well device (such as e.g., a multi-well plate or a multi-well chip or the like).

In some instances, components necessary for particular reaction steps may be disposed in a reaction vessel prior to the addition of other reagents, e.g., the reaction vessel may be pre-prepared with one or more components of the reaction. For example, a reaction vessel may be pre-prepared with one or more oligonucleotides, including where such oligonucleotides are disposed in the reaction vessel in a hydrated (e.g., in a solution or droplet) or dehydrated (e.g., dried, lyophilized) form. Dehydrated reaction components, e.g., lyophilized oligonucleotides, may be rehydrated in the reaction vessel prior to use or may be rehydrated during the addition of the reaction components.

Reaction vessels into which the reaction mixtures and components thereof may be added and within which the reactions of the subject methods may take place will vary. Useful reaction vessels include but are not limited to e.g., tubes (e.g., single tubes, multi-tube strips, etc.), wells (e.g., of a multi-well plate (e.g., a 96-well plate, 384 well plate, or a plate with any number of wells such as 2000, 4000, 6000, or 10000 or more). Multi-well plates may be independent or may be part of a chip and/or device, e.g., as described in greater detail below.

In some instances, reaction mixtures and components thereof may be added to, and the reactions of the subject methods may take place in, a liquid droplet (e.g., a water-oil emulsion droplet), e.g., as described in more detail below. Whereas the droplets may serve the purpose of individual reaction vessels, the droplets (or emulsion containing droplets) will generally be housed in a suitable container such as, e.g., a tube or well or microfluidic channel. Reactions performed in droplets may be sorted, e.g., based on fluorescence (e.g., from nucleic acid detection reagent or labeled probe), using a fluorescence-based droplet sorter. Useful fluorescence-based droplet sorters will vary and may include e.g., a flow cytometers, microfluidic-based droplet sorters, and the like.

In certain embodiments of the methods described herein, droplets are obtained and a single droplet is sorted into one well of a multi-well plate, or other suitable container, such as a microfluidic chamber or tube. The reaction mixture may be added directly to the droplet, e.g., without additional purification.

In some instances, the methods may include the step of obtaining single droplets. Obtaining single droplets may be done according to any convenient protocol, including e.g., mechanically sorting droplets (e.g., utilizing a fluorescence-based sorter (e.g., a flow cytometer or microfluidic-based sorter). Single droplets can be placed in any suitable reaction vessel in which single droplets can be treated individually. For example, a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm.

The wells (e.g., nanowells) in the multi-well plates may be fabricated in any convenient size, shape or volume. The wells may be 100 μm to 1 mm in length, 100 μm to 1 mm in width, and 100 μm to 5 mm, or more in depth. In some instances, the wells may have a depth of 5 mm or less, including but not limited to e.g., 4 mm or less, 3 mm or less, 2 mm or less, 1 mm or less. In various embodiments, each nanowell has an aspect ratio (ratio of depth to width) of from 1 to 6 or more. In one embodiment, each nanowell has an aspect ratio of 1:6. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 μl. The nanowell may have a volume of 1 μl or less, such as 500 nl or less. The volume may be 200 nl or less, such as 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

Prepared reaction mixtures will provide the components necessary to generate conditions sufficient to produce a subject product nucleic acid, including e.g., final and intermediate product nucleic acids. By "conditions sufficient to produce" the subject nucleic acid and/or elongate a nucleic acid primer is meant reaction conditions that permit the relevant nucleic acids and/or other reaction components in the reaction to interact with one another in the desired manner. For example, in some instances, the conditions may be sufficient for nucleic acids of the reaction mixture to hybridize. In some instances, the conditions may be sufficient for an enzyme of the reaction mixture to catalyze a chemical process such as e.g., polymerization, hydrolysis, etc. Achieving suitable reaction conditions may include selecting reaction mixture components, concentrations thereof, and a reaction temperature to create an environment in which the relevant processes proceed, including e.g., the relevant nucleic acids hybridize with one another in a sequence specific manner, the relevant polymerase polymerizes resulting in elongation of a nucleic acid, etc. In addition to specific nucleic acids (e.g., template nucleic acids, oligonucleotides, primers, etc.) of a reaction the reaction mixture may include buffer components that establish an appropriate pH, salt concentration (e.g., KCl concentration), etc. Conditions sufficient to produce a double stranded nucleic acid complex may include those conditions appropriate for hybridization, also referred to as "hybridization conditions".

Achieving suitable reaction conditions may include selecting reaction mixture components, concentrations thereof, and a reaction temperature to create an environment in which one or more polymerases are active and/or the relevant nucleic acids in the reaction interact (e.g., hybridize) with one another in the desired manner. In suitable reaction conditions, in addition to reaction components, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction(s) and/or template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Takara Bio USA, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and/or template-switching.

One or more reaction mixtures may have a pH suitable for a primer extension reaction and/or template-switching and/or amplification. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for primer extension reactions may vary according to factors such as the particular polymerase employed, the melting temperatures (Tm) of any primers employed, etc. In some instances, a reverse transcriptase (e.g., an MMLV reverse transcriptase) may be employed and the reaction mixture conditions sufficient for reverse transcriptase-mediated extension of a hybridized primer include bringing the reaction mixture to a temperature ranging from 4° C. to 72° C., such as from 16° C. to 70° C., e.g., 37° C. to 50° C., such as 40° C. to 45° C., including 42° C.

Template Nucleic Acids

Components of the subject reaction mixtures may include one or more template nucleic acids. Such template nucleic acids provide the template from which template nucleic acid-mediated primer extension reactions and other nucleic acid production reactions may be performed. Nucleic acid templates may be added to a reaction mixture, e.g., through direct addition of the nucleic acid template, through lysing one or more cells containing the nucleic acid template, and the like, or one or more nucleic acid templates may be generated during the reaction, e.g., as an intermediate product of a prior nucleic acid production reaction. Essentially any nucleic acid template may find use in the subject methods, including e.g., RNA template nucleic acid and DNA template nucleic acids. RNA template nucleic acids may vary and may include e.g., messenger RNA (mRNA) templates, and the like. In addition, various types of DNA templates may be employed, including but not limited to e.g., genomic DNA templates, mtDNA templates, synthetic DNA templates, etc.

According to certain embodiments, useful template nucleic acids include template ribonucleic acids (template RNA). Template RNAs may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

According to certain embodiments, useful template nucleic acids include template deoxyribonucleic acids (template DNA). A template DNA may be any type of DNA of interest to a practitioner of the subject methods, including but not limited to genomic DNA or fragments thereof, complementary DNA (or "cDNA", synthesized from any RNA or DNA of interest), recombinant DNA (e.g., plasmid DNA), or the like.

The number of distinct template nucleic acids of differing sequence in a given template nucleic acid composition may vary. While the number of distinct template nucleic acids in a given template nucleic acid composition may vary, in some instances the number of distinct template nucleic acids in a given template nucleic acid composition ranges from 1 to $10^8$, such as 1 to $10^7$, including 1 to $10^5$.

The template nucleic acid composition employed in such methods may be any suitable nucleic acid sample. The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 fg/µL to 10 µg/µL, such as from 1 pg/µL to 5 µg/µL, such as from 0.001 µg/µL to 2.5 µg/µL, such as from 0.005 µg/µL to 1 µg/µL, such as from 0.01 µg/µL to 0.5 µg/µL, including from 0.1 µg/µL to 0.25 µg/µL.

Template nucleic acid components are nucleic acid samples that contain one or more types of template nucleic acids, as described in more detail below. Template nucleic acid components may be derived from cellular samples including cellular samples that contain a single cell or a population of cells containing, e.g., two or more cells. Cellular samples may be derived from a variety of sources including but not limited to e.g., a cellular tissue, a biopsy, a blood sample, a cell culture, etc. Additionally, cellular samples may be derived from specific organs, tissues, tumors, neoplasms, or the like. Furthermore, cells from any population can be the source of a cellular sample used in the subject methods, such as a population of prokaryotic or eukaryotic single celled organisms including bacteria or yeast.

As such, in some instances, the source of nucleic acid samples utilized in the subject methods may be a mammalian cellular sample, such as a rodent (e.g., mouse or rat) cellular sample, a non-human primate cellular sample, a human cellular sample, or the like. In some instances, a mammalian cellular sample may be mammalian blood sample, including but not limited to e.g., a rodent (e.g., mouse or rat) blood sample, a non-human primate blood sample, a human blood sample, or the like.

In some instances, the source of a nucleic acid sample utilized in the subject methods may be derived from an immune cell, including but not limited to a lymphocyte e.g., a T cell (e.g., a cytotoxic T cell (e.g., a CD8$^+$ T cell), a helper T cell (e.g., a CD4$^+$ T cell), a regulatory T cell ("Treg"), etc.) a natural killer (NK) cell, a B cell, and the like. Subject immune cells may also include e.g., peripheral blood mononuclear cells, a macrophage, a dendritic cell, a monocyte, etc.

In some instances, the source of a nucleic acid sample utilized in the subject methods may be derived from a plant, such as a monocot or a dicot, including but not limited to e.g., research plants (e.g., Arabidopsis) and agricultural plants such as fruits (e.g., apples, apricots, avocados, bananas, blackberries, blueberries, cantaloupe, coconuts, cranberries, dates, figs, melon, grapefruit, grapes, guava, honeydews, kiwifruit, lemons, limes, mangoes, nectarines, olives, oranges, papaya, passion fruit, peaches, pears, pineapples, plantains, plums, pomegranates, prunes, raspberries, strawberries, tangerines, watermelons, etc.), crops (e.g., barley, beans, canola, corn, cotton, flaxseed, hay, oats, peanuts, rice, sorghum, soybeans, sugarbeets, sugarcane, sunflowers, tobacco, wheat, etc.), vegetables (e.g., artichokes, asparagus, beans, beets, bok choy, broccoli, brussels sprouts, cabbage, carrots, cauliflower, celery, collard greens, corn-sweet, cucumbers, eggplant, endive, greens, kale greens, lettuce, parsley, parsnips, peas, peppers, pumpkins, radishes, rhubarb, rutabagas, spinach, squash, sweet potatoes, tomatillos, tomatoes, turnips, water chestnuts, etc.), and the like.

In some instances, the source of a nucleic acid sample utilized in the subject methods may be derived from a virus, such as e.g., dsDNA viruses, ssDNA viruses, dsRNA viruses, (+)ssRNA viruses, (−)ssRNA viruses, ssRNA-RT viruses and dsDNA-RT viruses. Viruses may be plant or animal virus, including e.g., virus that infect mammalian hosts, including but not limited to humans. Virus of interest may also be those that infect microorganisms including but not limited to e.g., bacterial viruses (i.e., bacteriophages), archaeal viruses, etc.

In some instances, the template nucleic acid component is from a single cell. A template nucleic acid component from a single cell is a nucleic acid composition, e.g., a composition of one or more distinct nucleic acids, such as ribonucleic acids or deoxyribonucleic acids that originate or are derived from a single cell. As used herein, a "single cell" refers to one cell. Single cells useful as the source of template nucleic acids, e.g., RNAs or DNAs, can be obtained from an organism or tissue of interest, or from a biopsy, blood sample, or cell culture, etc. Additionally, cells from specific organs, tissues, tumors, neoplasms, or the like can be obtained and used in the methods described herein.

In some instances, the template nucleic acid component is obtained from a portion of a single cell. Single cell portions of interest include, but are not limited to: organelles, exosomes or more broadly nucleic acids contained within, or associated with, a protein and or lipid bearing membrane.

Template nucleic acids of template nucleic acid components employed in embodiments of the invention may contain a plurality of distinct template nucleic acids of differing sequence. Template nucleic acids (e.g., a template RNA, a template DNA, or the like) may be polymers of any length. While the length of the polymers may vary, in some instances the polymers are 10 nts or longer, 20 nts or longer, 50 nts or longer, 100 nts or longer, 500 nts or longer, 1000 nts or longer, 2000 nts or longer, 3000 nts or longer, 4000 nts or longer, 5000 nts or longer or more nts. In certain aspects, template nucleic acids are polymers, where the number of bases on a polymer may vary, and in some instances is 10 nts or less, 20 nts or less, 50 nts or less, 100 nts or less, 500 nts or less, 1000 nts or less, 2000 nts or less, 3000 nts or less, 4000 nts or less, or 5000 nts or less, 10,000 nts or less, 25,000 nts or less, 50,000 nts or less, 75,000 nts or less, 100,000 nts or less.

Single Cells

Single cells, for use in the herein described methods relating thereto, may be obtained by any convenient method. For example, in some instances, single cells may be obtained through limiting dilution of cellular sample. In some instances, the present methods may include a step of obtaining single cells. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example, a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm. Such methods are further described in greater detail below.

In some instances, single cells may be obtained by sorting a cellular sample using a cell sorter instrument. By "cell sorter" as used herein is meant any instrument that allows for the sorting of individual cells into an appropriate vessel for downstream processes, such as those processes of library preparation as described herein. Useful cell sorters include flow cytometers, such as those instruments utilized in fluorescence activated cell sorting (FACS). Flow cytometry is a well-known methodology using multi-parameter data for identifying and distinguishing between different particle (e.g., cell) types i.e., particles that vary from one another terms of label (wavelength, intensity), size, etc., in a fluid medium. In flow cytometrically analyzing a sample, an aliquot of the sample is first introduced into the flow path of the flow cytometer. When in the flow path, the cells in the sample are passed substantially one at a time through one or more sensing regions, where each of the cells is exposed separately individually to a source of light at a single wavelength (or in some instances two or more distinct sources of light) and measurements of scatter and/or fluorescent parameters, as desired, are separately recorded for each cell. The data recorded for each cell is analyzed in real time or stored in a data storage and analysis means, such as a computer, for later analysis, as desired.

Cells sorted using a flow cytometer may be sorted into a common vessel (i.e., a single tube), or may be separately sorted into individual vessels. For example, in some instances, cells may be sorted into individual wells of a multi-well plate, as described below.

Useful cell sorters also include multi-well-based systems that do not employ flow cytometry. Such multi-well based systems include essentially any system where cells may be deposited into individual wells of a multi-well container by any convenient means, including e.g., through the use of Poisson distribution (i.e., limiting dilution) statistics, individual placement of cells (e.g., through manual cell picking or dispensing using a robotic arm or pipettor). In some instances, useful multi-well systems include a multi-well wafer or chip, where cells are deposited into the wells or the wafer/chip and individually identified by a microscopic analysis system. In some instances, an automated microscopic analysis system may be employed in conjunction with a multi-well wafer/chip to automatically identify individual cells to be subjected to downstream analyses, including library preparation, as described herein.

In some instances, one or more cells may be sorted into or otherwise transferred to an appropriate reaction vessel. Reaction components may be added to reaction vessels, including e.g., components for preparing a template nucleic acid component, components for generating a product double stranded cDNA, components for one or more library preparation reactions, etc.

The wells of a multi-well device can be designed such that a single well includes a single cell or a single droplet. An individual cell or droplet may also be isolated in any other suitable container, e.g., microfluidic chamber, droplet, nanowell, tube, etc. Any convenient method for manipulating single cells or droplets may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells or droplets can be deposited in wells of a plate according to Poisson statistics (e.g., such that approximately 10%, 20%, 30% or 40% or more of the wells contain a single cell or droplet—which number can be defined by adjusting the number of cells or droplets in a given unit volume of fluid that is to be dispensed into the containers). In some instances, a suitable reaction vessel comprises a droplet (e.g., a microdroplet). Individual cells or droplets can, for example, be individually selected based on features detectable by microscopic observation, such as location, morphology, the presence of a reporter gene (e.g., expression), the presence of a bound antibody (e.g., antibody labelling), FISH, the presence of an RNA (e.g., intracellular RNA labelling), or qPCR.

Following obtainment of a desired cell population or single cells, e.g., as described above, nucleic acids can be released from the cells by lysing the cells. Lysis can be achieved by, for example, heating or freeze-thaw of the cells, or by the use of detergents or other chemical methods, or by a combination of these. However, any suitable lysis method can be used. In some instances, a mild lysis procedure can advantageously be used to prevent the release of nuclear chromatin, thereby avoiding genomic contamination of a cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kurimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313).

Template Switching

In some instances, the present methods may make use of a template-switching reaction, and may, e.g., include the use of a template-switching oligonucleotide. A template switch oligonucleotide is an oligonucleotide utilized in a template switching reaction, including the production of a product nucleic acid from a template nucleic acid, e.g., reverse transcription of a RNA template or reverse transcription of a DNA template. As such, production of a product nucleic acid may utilize template switching and the ability of certain nucleic acid polymerases to "template switch" i.e., use a first nucleic acid strand as a template for polymerization, and then switch to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid. The methods of the present disclosure may make use of a template switch oligonucleotide in production of a product nucleic acid by template switching. In some instances, the template switch oligonucleotide may be further utilized as a primer in an amplification reaction, such as in the amplification of a product nucleic acid or an intermediate component of a series of reaction steps. In some instances, the template switch oligonucleotide may not be employed as a primer in an amplification reaction (i.e., the template switch oligonucleotide may not be elongated in an amplification reaction). For example, one or more primers that are not template switch oligonucleotides may be employed, such as but not limited to e.g., first strand primers, second strand synthesis primers, PCR amplification primers, etc. Accordingly, depending on the context, a template switch oligonucleotide may be employed to serve multiple functions (e.g., a template switching function and a primer function) or solely to provide a template switching function.

Figure 3:
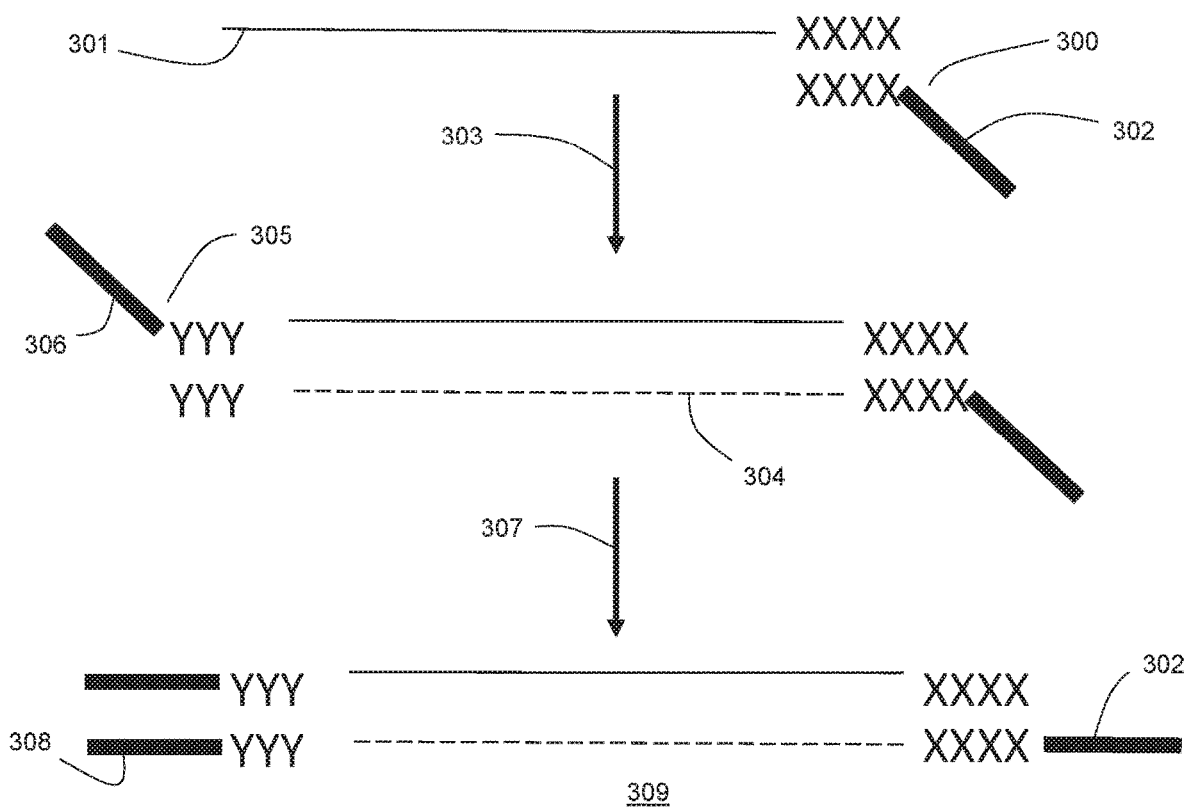
FIG. 3 provides a schematic depiction of a template-switching reaction.

Turning to FIG. 3, a schematized example of a template switching reaction is depicted. In the embodiment shown, a single product nucleic acid primer (300) hybridizes to a template nucleic acid (301) through complementary sequence (represented by "XXXX") shared by the single product nucleic acid primer and the template. The single product nucleic acid primer may, but need not necessarily, include a region of additional sequence (302) that is not complementary to the template (e.g., non-templated). Following annealing of the single product nucleic acid primer to the template, reverse transcription (303) proceeds, through the use of a reverse transcriptase, to generate a single product nucleic acid strand (304) that is complementary to the template. The reverse transcriptase, having terminal transferase activity, transfers non-templated nucleotides to the generated single product nucleic acid (represented by "YYY") and a template switching oligonucleotide (305) hybridizes to the non-templated nucleotides of the single product nucleic acid by a sequence of complementary nucleotides (also represented by "YYY" and also referred to herein as a 3' hybridization domain) present on the template switch oligonucleotide. The template switch oligonucleotide includes additional sequence (306) that does not hybridize to the non-templated nucleotides. Template switching occurs (307), wherein the reverse transcriptase switches from the template to utilize the template switching oligonucleotide as a second template, transcribing the additional sequence (306) to generate its complement (308). The now fully generated single product nucleic acid strand (309) includes the complete sequence of the single product nucleic acid primer, including any additional sequence (302), if present, that did not hybridize to the template, the complementary sequence of the template and the complementary sequence of the template switch oligonucleotide. Methods and reagents related to template switching are also described in U.S. Pat. No. 9,410,173; the disclosure of which is incorporated herein by reference in its entirety.

In some embodiments, the above methods are employed in a workflow that includes producing first strand cDNA (or RNA, e.g., via T7 or SP6 RNA polymerase) from a template nucleic acid component via a template switch oligonucleotide protocol, followed by amplification of the resultant cDNA to produce an amplified nucleic acid production composition, which product composition may optionally be further amplified as desired, e.g., to introduce one or more functionalities into the final product composition.

In such instances, a first strand nucleic acid primer, i.e., a first strand cDNA synthesis primer, hybridizes to a template nucleic acid through complementary sequence shared by the first strand nucleic acid primer and the template nucleic acid. The first strand nucleic acid primer may, but need not necessarily, include a region of additional sequence that is not complementary to the template (e.g., non-templated). In addition, the first strand primer may include one or more ribonucleotides, such as one or more 3' ribonucleotides.

Following annealing of the first strand nucleic acid primer to the template, reverse transcription proceeds, e.g., through the use of a reverse transcriptase, to generate a single product nucleic acid strand that is complementary to the template, e.g., a first strand cDNA product nucleic acid. The reverse transcriptase, having terminal transferase activity, transfers non-templated nucleotides to the generated single product nucleic acid and a template switching oligonucleotide hybridizes to the non-templated nucleotides of the single product nucleic acid by a sequence of complementary nucleotides present on the template switch oligonucleotide. The template switch oligonucleotide includes additional sequence that does not hybridize to the non-templated nucleotides. Template switching occurs, wherein the reverse transcriptase switches from the template to utilize the template switching oligonucleotide as a second template, transcribing additional sequence to generate its complement. The now fully generated single product nucleic acid strand includes the complete sequence of the first strand nucleic acid primer, including any additional sequence, if present, that did not hybridize to the template, the complementary sequence of the template and the complementary sequence of the template switch oligonucleotide. Methods and reagents related to template switching are also described in U.S. Pat. No. 9,410,173; the disclosure of which is incorporated herein by reference in its entirety.

A template-switching reverse transcription reaction may make use of a suitable reaction mixture. Suitable reaction mixtures for a template-switching reverse transcription reaction may include the template switch oligonucleotide at a concentration sufficient to readily permit template switching of the polymerase from the template to the template switch oligonucleotide and further elongation by a polymerase as templated by any additional sequence, if present, of the template switch oligonucleotide. For example, the template switch oligonucleotide may be added to the reaction mixture at a final concentration of from 0.01 to 100 µM, such as from 0.1 to 10 µM, such as from 0.5 to 5 µM, including 1 to 2 µM (e.g., 1.2 µM).

In a template-switching reverse transcription reaction, a template switch oligonucleotide may or may not include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

In certain aspects, the template switch oligonucleotide includes a 3' hybridization domain. The 3' hybridization domain may vary in length, and in some instances ranges from 2 to 10 nts in length, such as 3 to 7 nts in length. The 3' hybridization domain of a template switch oligonucleotide may include a sequence complementary to a non-templated sequence added to a single product nucleic acid of the template-switching reaction (e.g., a cDNA). Non-templated sequences, described in more detail below, generally refer to those sequences that do not correspond to and are not templated by a template, e.g., a RNA template or a DNA template. Where present in the 3' hybridization domain of a template switch oligonucleotide, non-templated sequences may encompass the entire 3' hybridization domain or a portion thereof. In some instances, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence may include or consist of a homo-polynucleotide, where such a homo-polynucleotide may vary in length from 2 to 10 nts in length, such as 3 to 7 nts in length, including 3 nts.

In some instances, a template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

In some instances, a template switch oligonucleotide may include a 5' adapter sequence (e.g., a defined nucleotide sequence 5' of the 3' hybridization domain of the template switch oligonucleotide), the 5' adapter sequence may serve various purposes in downstream applications. In some instances, the 5' adapter sequence may serve as a primer binding site for further amplification or, e.g., nested amplification or suppression amplification, of the amplified dsDNA.

In some instances, a polymerase combined into a template-switching reverse transcription reaction mixture is capable of template switching, where the polymerase uses a first nucleic acid strand as a template for polymerization, and then switches to the 3' end of a second template nucleic acid strand to continue the same polymerization reaction. In some instances, the polymerase capable of template switching is a reverse transcriptase. Reverse transcriptases capable of template-switching that find use in practicing the subject methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof, e.g., RNase H minus or RNase H reduced enzymes. For example, the reverse transcriptase may be a Moloney Murine Leukemia Virus reverse transcriptase (MMLV RT) or a *Bombyx mori* reverse transcriptase (e.g., *Bombyx mori* R2 non-LTR element reverse transcriptase). Polymerases capable of template switching that find use in practicing the subject methods are commercially available and include SMARTScribe™ reverse transcriptase and PrimeScript™ reverse transcriptase available from Takara Bio USA, Inc. (Mountain View, Calif.).

A template-switching reverse transcription reaction of the present methods may include the use of a polymerase having terminal transferase activity. For example, the polymerase (e.g., a reverse transcriptase such as MMLV RT) combined into the reaction mixture has terminal transferase activity such that a nucleotide stretch, such as a homonucleotide stretch or heteronucleotide stretch (e.g., made up of Gs and/or Cs) may be added to the 3' end of a nascent strand, and the 3' hybridization domain of the template switch oligonucleotide includes a complementary stretch that is complementary to that of the 3' end of the nascent strand. In other aspects, when the polymerase having terminal transferase activity adds a nucleotide stretch to the 3' end of the nascent strand (e.g., a trinucleotide stretch), the 3' hybridization domain of the template switch oligonucleotide includes a hetero-trinucleotide comprises a nucleotide comprising cytosine and a nucleotide comprising guanine (e.g., an $r(C/G)_3$ oligonucleotide), which hetero-trinucleotide stretch of the template switch oligonucleotide is complementary to the 3' end of the nascent strand. Examples of 3' hybridization domains and template switch oligonucleotides are further described in U.S. Pat. No. 5,962,272, the disclosure of which is herein incorporated by reference.

A polymerase with terminal transferase activity is capable of catalyzing the addition of deoxyribonucleotides to the 3' hydroxyl terminus of a RNA or DNA molecule. In certain aspects, when the polymerase reaches the 5' end of the template, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent strand. All of the nucleotides may be the same (e.g., creating a homonucleotide stretch at the 3' end of the nascent strand) or one or more of the nucleotides may be different from the other(s) (e.g., creating a heteronucleotide stretch at the 3' end of the nascent strand). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). For example, according to one embodiment, the polymerase is an MMLV reverse transcriptase (MMLV RT). MMLV RT incorporates additional nucleotides (predominantly dCTP, e.g., three dCTPs) at the 3' end of the nascent strand. These additional nucleotides may be useful for enabling hybridization between a 3' hybridization domain of a template switch oligonucleotide and the 3' end of the nascent strand, e.g., to facilitate template switching by the polymerase from the template to the template switch oligonucleotide.

Reverse transcriptase utilized in the subject methods may, in some instances, be a thermo-sensitive polymerase, i.e., a polymerase that is not thermostable. Such thermo-sensitive polymerases may become inactive at a temperature above their active temperature range. For example, in some instances, a thermos-sensitive polymerase may become inactive or demonstrate significantly reduced activity after being exposed to temperatures of 75° or higher, 80° or higher, 85° or higher, 90° or higher or 95° or higher.

Where a reverse transcriptase is employed, it may be combined into the reaction mixture such that the final concentration of the reverse transcriptase is sufficient to produce a desired amount of the RT reaction product, e.g., a desired amount of a single product nucleic acid. In certain aspects, the reverse transcriptase (e.g., an MMLV RT, a *Bombyx mori* RT, etc.) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

Tagmentation

As summarized above, in some instances, the present methods may make use of a tagmentation reaction, and may, e.g., include the use of tagmentation reaction components. The reaction components and the process of tagmentation employed will vary. Transposomes, employed in tagmentation where present in methods provided, may include a transposase and a transposon nucleic acid that includes a transposon end domain and a post-tagmentation PCR primer binding domain. These domains are defined functionally and so may be one in the same sequence or may be different sequences, as required by the researcher. The domains may also overlap, such that part of the post-tagmentation PCR primer binding domain may be present in the transposon end domain.

Tagmentation processes, transposition-based sequence manipulation, and components that may be employed in a tagmentation or transposition-based reactions are described in, e.g., U.S. Pat. Nos. 10,017,759; 9,790,476; 9,683,230; 9,388,465; 9,238,671; 9,193,999; 8,383,345; 6,294,385; 6,159,736; 5,869,296 and 5,677,170; the disclosures of which are incorporated herein by reference in their entirety. Various tagmentation processes, and/or one or more components thereof, may be adapted for use in the herein described methods.

A "transposase" means an enzyme that is capable of forming a functional complex with a transposon end domain-containing composition (e.g., transposons, transposon ends, transposon end compositions) and catalyzing insertion or transposition of the transposon end-containing composition into the double-stranded target DNA with which it is incubated in an in vitro transposition reaction. Transposases that find use in practicing the provided methods include, but are not limited to, Tn5 transposases, Tn7 transposases, and Mu transposases. The transposase may be a wild-type transposase. In other aspects, the transposase includes one or more modifications (e.g., amino acid substitutions) to improve a property of the transposase, e.g., enhance the activity of the transposase. For example, hyperactive mutants of the Tn5 transposase having substitution mutations in the Tn5 protein (e.g., E54K, M56A and L372P) have been developed and are described in, e.g., Picelli et al. (2013) *Genome Research* 24:2033-2040.

The term "transposon end domain" means a double-stranded DNA that consists only of the nucleotide sequences (the "transposon end sequences") that are necessary to form the complex with the transposase or integrase enzyme that is functional in an in vitro transposition reaction. A transposon end domain forms a "complex" or a "synaptic complex" or a "transposome complex" or a "transposome composition" with a transposase or integrase that recognizes and binds to the transposon end domain, and which complex is capable of inserting or transposing the transposon end domain into target DNA with which it is incubated in an in vitro transposition reaction. A transposon end domain exhibits two complementary sequences consisting of a "transferred transposon end sequence" or "transferred strand" and a "non-transferred transposon end sequence," or "non-transferred strand." For example, one transposon end domain that forms a complex with a hyperactive Tn5 transposase (e.g., EZ-Tn5 Transposase, EPICENTRE Biotechnologies, Madison, Wis., USA) that is active in an in vitro transposition reaction includes a transferred strand that exhibits a "transferred transposon end sequence" as follows: 5' AGATGTGTATAAGAGACAG 3', (SEQ ID NO:XX) and a non-transferred strand that exhibits a "non-transferred transposon end sequence" as follows: 5' CTGTCTCTTATACACATCT 3' (SEQ ID NO:XX). The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction. The sequence of the particular transposon end domain to be employed when practicing the provided methods will vary depending upon the particular transposase employed. For example, a Tn5 transposon end domain may be included in the transposon nucleic acid when used in conjunction with a Tn5 transposase. Further details regarding transposases and transposon end domains that may be employed in transposomes of the invention include, but are not limited to: those described in U.S. Pat. Nos. 9,040,256, 9,080,211, and 9,115,396; the disclosures of which are herein incorporated by reference.

In addition to the transposon end domain, the transposon nucleic acid also includes a post-tagmentation primer binding domain. In some instances, the post-tagmentation primer binding domain may be subsequently utilized in an amplification reaction that adds a non-templated sequence, such as e.g., a sequencing platform adapter construct domain, (e.g., through the use of a primer that hybridizes with the post-tagmentation primer binding domain and has an attached non-templated sequence). In some instances, the post-tagmentation primer binding domain may include a non-templated sequence, such as a sequencing platform adapter construct domain.

Non-templated sequences, such as sequencing platform adapter construct domains, added during tagmentation or amplification that follows and depends upon tagmentation will vary. For example, useful sequencing platform adapter constructs may be a nucleic acid domain selected from a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system), a sequencing primer binding domain (e.g., a domain to which the Read 1 or Read 2 primers of the Illumina® platform may bind), a barcode domain (e.g., a domain that uniquely identifies the sample source of the nucleic acid being sequenced to enable sample multiplexing by marking every molecule from a given sample with a specific barcode or "tag"), a barcode sequencing primer binding domain (a domain to which a primer used for sequencing a barcode binds), a molecular identification domain, or any combination of such domains.

Other variations include, e.g., replacing Illumina®-specific sequencing domains in the various primers/oligonucleotides with sequencing domains required by sequencing systems from, e.g., Ion Torrent™ (e.g., the Ion PGM™ and Ion Proton™ sequencing systems); Pacific Biosciences (e.g., the PACBIO RS II sequencing system); Life Technologies™ (e.g., a SOLiD sequencing system); Roche (e.g., the 454 GS FLX+ and GS Junior sequencing systems); or any other sequencing platform of interest.

In a further variation, rather than using one or two types of transposomes, such as the TnRP1 or TnRP2 transposomes, 3 or more different types of transposomes may be employed for tagmentation. For example, 3 or more, 4 or more, 5 or more, 6 or more, 7 or more, 8 or more, 9 or more, 10 or more, 20 or more, 50 or more, or 100 or more different types of transposomes having different post-tagmentation PCR primer binding domains could be employed. Tagmentation products of interest in such a tagmented sample may be amplified using a primer that binds to a post-tagmentation PCR primer binding domain of a particular type of transposome, in conjunction with a primer that binds to a post-tagmentation PCR primer binding domain added during an earlier step (e.g., first strand synthesis or amplification of the double stranded product nucleic acid, etc.).

When it is desirable to prepare transposomes for the tagmentation step, any suitable transposome preparation approach may be used, and such approaches may vary depending upon, e.g., the specific transposase and transposon nucleic acids to be employed. For example, the transposon nucleic acids and transposase may be incubated together at a suitable molar ratio (e.g., a 2:1 molar ratio, a 1:1 molar ratio, a 1:2 molar ratio, or the like) in a suitable buffer. According to one embodiment, when the transposase is a Tn5 transposase, preparing transposomes may include incubating the transposase and transposon nucleic acid at a 1:1 molar ratio in 2× Tn5 dialysis buffer for a sufficient period of time, such as 1 hour.

Tagmenting a double stranded DNA includes contacting the double stranded DNA with a transposome under tagmentation conditions. Such conditions may vary depending upon the particular transposase employed. Typically, the conditions will include incubating the transposomes and tagged extension products in a buffered reaction mixture (e.g., a reaction mixture buffered with Tris-acetate, or the like) at a pH of from 7 to 8, such as pH 7.5. The transposome may be provided such that about a molar equivalent, or a molar excess, of the transposon is present relative to the tagged extension products. Suitable temperatures include from 32° to 42° C., such as 37° C. The reaction is allowed to proceed for a sufficient amount of time, such as from 5 minutes to 3 hours. The reaction may be terminated by adding a solution (e.g., a "stop" solution), which may include an amount of SDS and/or other transposase reaction termination reagent suitable to terminate the reaction. Protocols and materials for achieving fragmentation of nucleic acids using transposomes are available and include, e.g., those provided in the EZ-Tn5™ transpose kits available from EPICENTRE Biotechnologies (Madison, Wis., USA).

In some instances, a resultant tagmented sample may be subjected to PCR amplification conditions, e.g., using one or more post-tagmentation PCR primers that hybridize to one or more post-tagmentation primer binding sites added during the tagmentation reaction. Post-tagmentation primers may include non-templated sequence(s), such as e.g., sequencing platform adapter domains. The non-templated sequence(s) may include any of the nucleic acid domains described elsewhere herein (e.g., a domain that specifically binds to a surface-attached sequencing platform oligonucleotide, a sequencing primer binding domain, a barcode domain, a barcode sequencing primer binding domain, a molecular identification domain, or any combination thereof). Such embodiments find use, e.g., where nucleic acids of the tagmented sample do not include all of the adapter domains useful or necessary for sequencing in a sequencing platform of interest, and the remaining adapter domains are provided by the primers used for the amplification of the nucleic acids of the tagmented sample.

First Strand Synthesis Primers

As summarized above, in some instances, a first strand synthesis primer (e.g., a first strand cDNA primer) may be employed in the described methods, including e.g., where the first strand synthesis primer is a de-activatable oligonucleotide. A first strand synthesis primer includes a template binding domain. For example, the first strand synthesis primer may include a first (e.g., 3') domain that is configured to hybridize to a template nucleic acid, e.g., mRNA, etc., and may or may not include one or more additional domains which may be viewed as a second (e.g., 5') domain that does not hybridize to the template nucleic acid, e.g., a non-template sequence domain as described in more detail below. In addition, the first strand primer may include one or more ribonucleotides, such as one or more 3' ribonucleotides, e.g., as described in greater detail below. The sequence of the template binding domain may be independently defined or arbitrary. In certain aspects, the template binding domain has a defined sequence, e.g., poly dT or gene specific sequence. In other aspects, the template binding domain has an arbitrary sequence (e.g., a random sequence, such as a random hexamer sequence). While the length of the template binding domain may vary, in some instances the length of this domain ranges from 5 to 50 nts, such as 6 to 25 nts, e.g., 6 to 20 nts.

In some instances, a first strand primer of the subject methods may include a poly dT template binding domain that includes one or more cleavable bases. Where multiple cleavable bases are employed, the cleavable bases may be separated by one or more intervening deoxythymidylic acid residues. In some instances, a poly dT template binding domain may include 2 or more, including e.g., 3 or more, 4 or more, 5 or more, 6 or more, 7 or more, etc., including 2, 3, 4, 5, 6, 7, etc., cleavable bases. Various different cleavable bases may be employed, including but not limited to e.g., uracil-containing nucleotides.

A first strand synthesis primer may or may not include one or more nucleotides (or analogs thereof) that are modified or otherwise non-naturally occurring. For example, the single product nucleic acid primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the first strand synthesis primer.

In some instances, a first strand synthesis primer may include one or more non-templated sequences, such as but not limited to e.g., a 5' adapter sequence (e.g., a defined nucleotide sequence 5' of the 3' hybridization domain of the single product nucleic acid primer). A 5' adapter sequence may serve various purposes in downstream applications. In some instances, the 5' adapter sequence may serve as a primer binding site for further amplification or, e.g., nested amplification or suppression amplification.

Non-Templated Sequences

Aspects of the described methods may, in some instances, include the use of non-templated sequences. The terms "non-templated sequence" and "non-template sequence" generally refer to those sequences involved in the subject method that do not correspond to the template (e.g., are not present in the templates, do not have a complementary sequence in the template or are unlikely to be present in or have a complementary sequence in the template). Non-templated sequences are those that are not templated by a template, e.g., a RNA or DNA template, thus they may be, e.g., added during an elongation reaction in the absence of corresponding template, e.g., nucleotides added by a polymerase having non-template directed terminal transferase activity. The addition of non-templated sequence to a nucleic acid need not be necessarily limited to elongation reaction. For example, in some instances, a non-templated sequence may be added through ligation of the non-templated sequence to the nucleic acid. Accordingly, non-templated sequences may vary and may be added to templated sequence through a variety of means.

Non-template and non-templated sequence may, but not exclusively, refer to those sequences present on a primer or template switch oligonucleotide that do not hybridize to the nucleic acid template (such sequences may, in some instances, be referred to as non-hybridizing sequence). Non-templated sequence will vary, in both size and composition. In some instances, non-templated sequence, e.g., non-templated sequence present on a template switch oligonucleotide or a primer, may range from 10 nt to 1000 nt or more including but not limited to e.g., 10 nt to 900 nt, 10 nt to 800 nt, 10 nt to 700 nt, 10 nt to 600 nt, 10 nt to 500 nt, 10 nt to 400 nt, 10 nt to 300 nt, 10 nt to 200 nt, 10 nt to 100 nt, 10 nt to 90 nt, 10 nt to 80 nt, 10 nt to 70 nt, 10 nt to 60 nt, 10 nt to 50 nt, 10 nt to 40 nt, 10 nt to 30 nt, 10 nt to 20 nt, etc.

In some instances, a non-templated sequence, as noted above, may be included in the 3' hybridization domain of a template switch oligonucleotide. When present in the 3' hybridization domain of a template switch oligonucleotide, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence present in the 3' hybridization domain of a template switch oligonucleotide may include or consist of a homo-polynucleotide, where such a homo-polynucleotide may vary in length from 2 to 10 nts in length, such as 3 to 7 nts in length, including 3 nts.

Non-templated sequences present on an oligonucleotide or a primer may be present at the 5' end of the oligonucleotide or primer and may, in such instances, be referred to as a 5' non-templated sequence. In some instances, only one oligonucleotide or primer may include a non-templated sequence (e.g., a 5' non-templated sequence) in a subject reaction. In some instances, two or more oligonucleotides and/or primers utilized in a subject reaction may include a non-templated sequence (e.g., a 5' non-templated sequence). Where two or more oligonucleotides and/or primers include a non-templated sequence, different non-templated sequences may be employed. In some instances, where two or more oligonucleotides and/or primers have a 5' non-templated sequence, such sequences may have the same 5' non-templated sequence.

In some instances, non-templated sequence, including e.g., 5' non-templated sequence, may include one or more primer binding sites. In some instances, one or more primer binding sites may be incorporated into a subject nucleic acid allowing further amplification of the produced nucleic acid, including e.g., amplifying all or a portion of the nucleic acid using one or more of the primer binding sites.

Useful primer binding sites will vary widely depending on the desired complexity of the primer binding site and the corresponding primer. In some instances, useful primer binding sites include those having complementarity to a II A primer (e.g., as available from Takara Bio USA, Inc., Mountain View, Calif.). According to one embodiment, an oligonucleotide or a primer utilized in generating a product double stranded cDNA includes a non-template sequence that includes a II A primer binding site. According to one embodiment, a nucleic acid utilized in an end capturing reaction includes a non-template sequence that includes a II A primer binding site.

In some instances, non-templated sequence, including e.g., 5' non-templated sequence, may include one or more barcode sequences. In some instances, such barcode sequences may be or may include a unique molecular identifier (UMI) domain and/or a barcoded unique molecular identifier (BUMI) domain. UMI and BUMI nucleic acids, and their use in various applications, are further described in PCT International Publication No. WO 2018/089550 A1; the disclosure of which is incorporated herein by reference in its entirety.

In some instances, one or more barcode sequences of a non-templated sequence may provide for retrospective identification of the source of a generated nucleic acid, e.g., following a sequencing reaction where the barcode is sequenced. For example, in some instances, a non-templated sequence that includes a barcode specific for the source (e.g., sample, well, cell, etc.) of the template is incorporated during a reaction. Such source identifying barcodes may be referred to herein as a "source barcode sequence" and such sequences may vary and may be assigned a term based on the source that is identified by the barcode. Source barcodes may include e.g., a sample barcode sequence that retrospectively identifies the sample from which the sequenced nucleic acid was generated, a well barcode sequence that retrospectively identifies the well (e.g., of a multi-well plate) from which the sequenced nucleic acid was generated, a droplet barcode sequence that retrospectively identifies the droplet from which the sequenced nucleic acid was generated, a cell barcode sequence that retrospectively identifies the cell (e.g., of a multi-cellular sample) from which the sequenced nucleic acid was generated, etc. Barcodes may find use in various procedures including e.g., where nucleic acids are pooled following barcoding, e.g., prior to sequencing.

In some instances, a non-templated sequence, e.g., present on an oligonucleotide and/or a nucleic acid primer, includes a sequencing platform adapter construct. By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, a non-templated sequence includes a sequencing platform adapter construct that includes a nucleic acid domain that is a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind). The sequencing platform adapter constructs may include nucleic acid domains (e.g., "sequencing adapters") of any length and sequence suitable for the sequencing platform of interest. In certain aspects, the nucleic acid domains are from 4 to 200 nts in length. For example, the nucleic acid domains may be from 4 to 100 nts in length, such as from 6 to 75, from 8 to 50, or from 10 to 40 nts in length. According to certain embodiments, the sequencing platform adapter construct includes a nucleic acid domain that is from 2 to 8 nts in length, such as from 9 to 15, from 16-22, from 23-29, or from 30-36 nts in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3'; SEQ ID NO:XX), P7 (5'-CAAGCAGAA-GACGGCATACGAGAT-3'; SEQ ID NO:XX), Read 1 primer (5'-ACACTCTTTCCCTACACGACGCTCTTCC-GATCT-3'; SEQ ID NO:XX) and Read 2 primer (5'-GTGACTGGAGTTCAGACGTGTGCTCTTCCGATCT-3'; SEQ ID NO:XX) domains employed on the Illumina®-based sequencing platforms. Other example nucleic acid domains include the A adapter (5'-CCATCT-CATCCCTGCGTGTCTCCGACTCAG-3'; SEQ ID NO:XX) and P1 adapter (5'-CCTCTC-TATGGGCAGTCGGTGAT-3'; SEQ ID NO:XX) domains employed on the Ion Torrent™-based sequencing platforms.

The nucleotide sequences of non-templated sequence domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the non-templated sequence (e.g., a template switch oligonucleotide and/or a single product nucleic acid primer, and/or the like) may be designed to include all or a portion of one or more nucleic acid domains in a configuration that enables sequencing the nucleic acid insert (corresponding to the template nucleic acid) on the platform of interest. Sequencing platform adaptor constructs that may be included in a non-templated sequence as well as other nucleic acid reagents described herein, are further described in U.S. patent application Ser. No. 14/478,978 published as US 2015-0111789 A1, the disclosure of which is herein incorporated by reference.

Non-templated sequence may be added to a nucleic acid of interest, e.g., to an oligonucleotide, a nucleic acid primer, a generated dsDNA, etc., by a variety of means. For example, as noted above, non-templated sequence may be added through the action of a polymerase with terminal transferase activity. Non-templated sequence, e.g., present on a primer or oligonucleotide, may be incorporated into a product nucleic acid during an amplification reaction. In some instances, non-templated nucleic acid sequence may be directly attached to a nucleic acid, e.g., to a primer or oligonucleotide prior to amplification, to a product of nucleic acid amplification, etc. Methods of directly attaching a non-templated sequence to a nucleic acid will vary and may include but are not limited to e.g., ligation, chemical synthesis/linking, enzymatic nucleotide addition (e.g., by a polymerase with terminal transferase activity), and the like.

In some instances, the methods may include attaching sequencing platform adapter constructs to ends of a nucleic acid. For example, in some instances, oligonucleotides and/or primers utilized in the subject methods may not include sequencing platform adapter constructs and thus desired sequencing platform adapter constructs may be attached following the production of a nucleic acid of interest. Adapter constructs attached to the ends of a nucleic acid of interest or a derivative thereof may include any sequence elements useful in a downstream sequencing application, including any of the elements described above with respect to the optional sequencing platform adapter constructs of the oligonucleotides and/or primers of the herein described methods. For example, the adapter constructs attached to the ends of nucleic acid of interest or a derivative thereof may include a nucleic acid domain or complement thereof selected from the group consisting of: a domain that specifically binds to a surface-attached sequencing platform oligonucleotide, a sequencing primer binding domain, a barcode domain, a barcode sequencing primer binding domain, a molecular identification domain, and combinations thereof.

Attachment of the sequencing platform adapter constructs may be achieved using any suitable approach. In certain aspects the adapter constructs are attached to the ends of the product nucleic acid or a derivative thereof using an approach that is the same or similar to "seamless" cloning strategies. Seamless strategies eliminate one or more rounds of restriction enzyme analysis and digestion, DNA end-repair, de-phosphorylation, ligation, enzyme inactivation and clean-up, and the corresponding loss of nucleic acid material. Seamless attachment strategies of interest include: the In-Fusion® cloning systems available from Takara Bio USA, Inc. (Mountain View, Calif.), SLIC (sequence and ligase independent cloning) as described in Li & Elledge (2007) *Nature Methods* 4:251-256; Gibson assembly as described in Gibson et al. (2009) *Nature Methods* 6:343-345; CPEC (circular polymerase extension cloning) as described in Quan & Tian (2009) *PLoS ONE* 4(7): e6441; SLiCE (seamless ligation cloning extract) as described in Zhang et al. (2012) *Nucleic Acids Research* 40(8): e55, and the GeneArt® seamless cloning technology by Life Technologies (Carlsbad, Calif.).

Any suitable approach may be employed for providing additional nucleic acid sequencing domains to a nucleic acid of interest or derivative thereof having less than all of the useful or necessary sequencing domains for a sequencing platform of interest. For example, a nucleic acid of interest or derivative thereof could be amplified using PCR primers having adapter sequences at their 5' ends (e.g., 5' of the region of the primers complementary to the nucleic acid of interest or derivative thereof), such that the amplicons include the adapter sequences in the original nucleic acid as well as the adapter sequences in the primers, in any desired configuration. Other approaches, including those based on seamless cloning strategies, restriction digestion/ligation, or the like may be employed.

Additional Processes

As summarized above, the described methods may include various additional processes, including e.g., where the product nucleic acids generated according to the herein described methods may be employed in various downstream processes, including but not limited to e.g., amplification, library preparation, sequencing and the like.

In some instances, methods provided may include an amplification step. Such amplification may make use of an amplification polymerase, e.g., for use in amplifying a nucleic acid produced during or following one or more reaction steps, a produced nucleic acid library, etc. Any convenient amplification polymerase may be employed including but not limited to DNA polymerases including thermostable polymerases. Useful amplification polymerases include e.g., Taq DNA polymerases, Pfu DNA polymerases, Terra DNA polymerase, those described in U.S. Pat. No. 6,127,155 (the disclosure of which is incorporated herein by reference in its entirety), derivatives thereof and the like. In some instances, the amplification polymerase may be a hot start polymerase including but not limited to e.g., a hot start Taq DNA polymerase, a hot start Pfu DNA polymerase, and the like.

An amplification polymerase may be combined into a reaction mixture such that the final concentration of the amplification polymerase is sufficient to produce a desired amount of product nucleic acid. In certain aspects, the amplification polymerase (e.g., a thermostable DNA polymerase, a hot start DNA polymerase, etc.) is present in the reaction mixture at a final concentration of from 0.1 to 200 units/μL (U/μL), such as from 0.5 to 100 U/μL, such as from 1 to 50 U/μL, including from 5 to 25 U/μL, e.g., 20 U/μL.

Nucleic acid reactions, e.g., amplification reactions, of the subject methods may include combining dNTPs into a reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). In some instances, one or more types of nucleotide added to the reaction mixture may be a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

Reaction mixtures may be subjected to various temperatures to drive various aspects of the reaction including but not limited to e.g., denaturing/melting of nucleic acids, hybridization/annealing of nucleic acids, polymerase-mediated elongation/extension, etc. Temperatures at which the various processes are performed may be referred to according to the process occurring including e.g., melting temperature, annealing temperature, elongation temperature, etc. The optimal temperatures for such processes will vary, e.g., depending on the polymerase used, depending on characteristics of the nucleic acids, etc. Optimal temperatures for particular polymerases, including reverse transcriptases and amplification polymerases, may be readily obtained from reference texts. Optimal temperatures related to nucleic acids, e.g., annealing and melting temperatures may be readily calculated based on known characteristics of the subject nucleic acid including e.g., overall length, hybridization length, percent G/C content, secondary structure prediction, etc.

In some instances, methods provided may include isolating and/or purifying a nucleic acid (e.g., a template nucleic acid), a nucleic acid product (e.g., an elongated (i.e., extended) nucleic acid, a nucleic acid library, etc.) and/or any intermediate nucleic acid product (e.g., an elongated (i.e., extended) nucleic acid, a double stranded product cDNA, etc.). Any convenient method of purification may be employed including but not limited to e.g., nucleic acid precipitation (i.e., alcohol precipitation), gel purification, etc. In some instances, a method of the present disclosure may exclude one or more nucleic acid isolation steps. For example, a subject method, or one or more steps thereof, may exclude purification of a template nucleic acid, purification of any intermediate nucleic acid product, purification of any final nucleic acid product, and/or the like.

Where desired, a given embodiment of the invention may include a pooling step e.g., where a composition is combined or pooled with one or more additional compositions. In protocols that include a pooling step, the pooling step can be performed at any convenient and appropriate stage of the procedure. For example, in some instances, pooling may be employed before production of any initial or intermediate nucleic acid added and/or produced in a reaction (e.g., a template nucleic acid, a cDNA (including a first strand cDNA), etc.). In some instances, pooling may be employed after production of a particular nucleic acid (e.g., a cDNA (including a first strand cDNA), a product nucleic acid, etc.). In some instances, pooling may be employed before and/or after an amplification step (e.g., a PCR amplification step) of the procedure. For example, in some instances, pooling may be employed after production of an amplified product nucleic acid composition, as desired. Where desired, a given single cell or droplet workflow may include a pooling step where a nucleic acid product composition, e.g., made up of an amplified product composition, is combined or pooled with the nucleic acid product compositions obtained from one or more additional cells or droplets. The number of different nucleic acid product compositions produced from different cells or droplets that are combined or pooled in such embodiments may vary, where the number ranges in some instances from 2 to 50, such as 3 to 25, including 4 to 20 or 10,000, or more. In some instances, pooling may be employed before sequencing a product nucleic acid of the subject procedure, including e.g., after amplification of the nucleic acid but before sequencing. In some instances, pooling may be employed prior to amplification of a nucleic acid for sequencing.

In instances where pooling is employed, in certain embodiments, the subject nucleic acids may be tagged or otherwise labeled (e.g., with a barcode or other identifying sequence, e.g., a cell or sample barcode) allowing for the retrospective identification of individual sources (e.g., of a plurality of organisms, tissues, cells, or subjects) following the pooling. Various methods may be employed for such identification of subpopulations of pooled nucleic acids, including e.g., one or more sequencing methods, including e.g., those described herein.

Following prescribed library preparation and/or amplification steps, prepared libraries may be considered ready for sequencing. In certain embodiments, the methods provided may further include subjecting a prepared library to an NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Roche (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

Kits, Compositions and Devices

Aspects of the present disclosure also include compositions and kits as well as devices for use therewith or therein. The compositions and kits may include, e.g., one or more of any of the reaction mixture components described above with respect to the subject methods.

The kits, compositions and devices of the present disclosure may include modifiable oligonucleotides, at least e.g., an activatable oligonucleotide, a de-activatable oligonucleotide, a plurality of different types of activatable oligonucleotides, a plurality of different types of de-activatable oligonucleotides, and/or combinations thereof. In some instances, a subject kit may include one or more stimuli and/or one or more stimulus or stimuli generating devices sufficient to modulate the activity (i.e., activate and/or deactivate) one or more oligonucleotides provided in the subject kit, composition or device.

In some instances, a kit, composition or device may include, e.g., at least two different types of de-activatable oligonucleotides, e.g., a de-activatable template switching oligonucleotide and a de-activatable first strand primer. Such kits, compositions and devices may include or exclude other components, including but not limited to e.g., enzymes (e.g., DNA polymerase, reverse transcriptase, RNase (e.g., RNase H), RNase inhibitor, transposase, proteases (e.g., proteinase K, etc.), additional nucleic acids (e.g., primers including e.g., primers containing non-templated sequences, transposons, control nucleic acids, etc.), buffers, dNTPs, and the like. In some instances, a subject kit, composition or device may include one or more stimuli, e.g., for activating one or more, including both, of the different types of de-activatable oligonucleotides.

In some instances, the kits, compositions and devices may include, e.g., at least an activatable oligonucleotide and a de-activatable oligonucleotide that are activatable and de-activatable by different stimuli or the same stimulus. For example, in some instances, a subject kit may include a single container or separate containers containing the activatable oligonucleotide and the de-activatable oligonucleotide that are activatable and de-activatable by different stimuli or the same stimulus. In some instances, a subject composition may include the activatable oligonucleotide and the de-activatable oligonucleotide that are activatable and de-activatable by different stimuli or the same stimulus. In some instances, a subject device, e.g., a multi-well device, may include the activatable oligonucleotide and the de-activatable oligonucleotide that are activatable and de-activatable by different stimuli or the same stimulus or a plurality of activatable oligonucleotide and de-activatable oligonucleotide pairs that are activatable and de-activatable by different stimuli or the same stimulus.

In some instances, the subject kits, compositions and devices may include activatable oligonucleotides and/or de-activatable oligonucleotides that include a specific enzymatically cleavable linkage, specific chemically cleavable linkage or a specific electromagnetically-labile linkage (e.g., light-labile linkages, heat-labile linkages, etc.). The provided oligonucleotides may have one or more or any combination of the above described characteristics.

Where the subject kits, compositions and devices include activatable oligonucleotides and de-activatable oligonucleotides that both include the same specific enzymatically cleavable linkage or different specific enzymatically cleavable linkages, the kits, compositions and devices may further be provided with the enzymatic stimuli or stimulus for activating and deactivating the oligonucleotides. For example, in some instances, one or more enzymes, such as a glycosylase, a nuclease (such as e.g., RNase H, an endonuclease, etc.), the like or a combination thereof, may be provided with the subject kits, compositions and devices.

Where the subject kits, compositions and devices include activatable oligonucleotides and de-activatable oligonucleotides that both include the same specific chemically cleavable linkage or different specific chemically cleavable linkages, the kits, compositions and devices may further be provided with one or more chemical stimuli for activating and deactivating the oligonucleotides. For example, a chemical agent that specifically cleaves an introduced cleavable internucleotide linkage may be provided with the subject kits, compositions and devices.

Where the subject kits, compositions and devices include activatable oligonucleotides and de-activatable oligonucleotides that both include the same specific electromagnetically-labile linkage or different specific electromagnetically-labile linkages, the kits, compositions and devices may further be provided with a device for applying one or more electromagnetic stimuli for activating and deactivating the oligonucleotides. For example, a light emitting device and/or a heat generating device may be provided with the subject kits, compositions and devices.

The kits, compositions and devices may, in some instances, include one or more additional components or be provided with one or more additional components including e.g., one or more reaction components added to a reaction mixture as described above, including but not limited to e.g., a polymerase (e.g., a template switching polymerase, a reverse transcriptase, an amplification polymerase, etc.), a buffer, dNTPs (including e.g., dATP, dCTP, dGTP, dTTP, dUTP, etc. or any one or any combination thereof), and the like. The subject kits may include or the compositions and devices may be provided with one or more test reagents, including e.g., control nucleic acids (e.g., control nucleic acid templates), and the like.

For example, the compositions and kits may include a nucleic acid sample (e.g., a DNA sample, an RNA sample, a combined RNA and DNA sample, etc.), an amplification polymerase (e.g., a thermostable polymerase, etc.), a reverse transcriptase (e.g., a reverse transcriptase capable of template-switching, etc.), a template switch oligonucleotide, a first strand cDNA primer, one or more pairs of amplification primers, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s). In certain instances, the provided kits may include one or more components for performing a template-switching reverse transcription reaction. Such components include but are not limited to those described herein including e.g., a template switching oligonucleotide, a primer, a reverse transcriptase, etc. In certain instances, the provided kits may include one or more components for performing a tagmentation reaction. Such components include but are not limited to those described herein including e.g., a transposase, a transposon, etc. In certain embodiments, the kits include reagents for isolating nucleic acids from a nucleic acid source of interest.

In some instances, components of the subject compositions and/or kits may be presented as a "cocktail" where, as used herein, a cocktail refers to a collection or combination of two or more different but similar components in a single vessel. Components of the kits may be present in separate containers, or multiple components may be present in a single container, as desired. The subject compositions may be present in any suitable environment. According to one embodiment, the composition is present in a reaction tube (e.g., a 0.2 mL tube, a 0.6 mL tube, a 1.5 mL tube, or the like) or a well or microfluidic chamber or droplet or other suitable container. In certain aspects, the composition is present in two or more (e.g., a plurality of) reaction tubes or wells (e.g., a plate, such as a 96-well plate, a multi-well plate, e.g., containing about 1000, 5000, or 10,000 or more wells). The tubes and/or plates may be made of any suitable material, e.g., polypropylene, or the like, PDMS, or aluminum. The containers may also be treated to reduce adsorption of nucleic acids to the walls of the container. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells or materials such as aluminum having high heat conductance.

In some instances, a collection of individual vessels (e.g., separate tubes) or containing multiple vessels, e.g., a multi-well device may include activatable and/or de-activatable oligonucleotides pre-disposed therein, including where the oligonucleotides are provide in liquid or dried form. For example, in some instances, the oligonucleotides may be dried in or pre-printed onto the vessels. In some instances, the oligonucleotides may be dried in or pre-printed onto or in the individual wells of a multi-well device.

In some instances, the subject kits may include one or more components for generating nucleic acid libraries. For example, a subject kit may include a plurality of individual vessels (where such individual vessels may be separate containers or wells of a multi-well device) each containing de-activatable oligonucleotides and/or activatable oligonucleotides. Components for generating libraries may include arrayed indexing and/or barcoding components. For example, a kit may include a plurality of individual vessels (as separate containers or wells of a multi-well device) each containing de-activatable oligonucleotides and/or activatable oligonucleotides, where at least one primer includes a unique sequence, such as a unique barcode sequence. In some instances, where multi-well devices are employed, the corresponding rows and/or columns and/or individual wells of the multi-well device may include an index sequence for retrospectively identifying the row/column/well from which a sample was derived. Such index sequences may, in some instances, be included on one or more of the activatable and/or de-activatable oligonucleotides of the kit, composition or device. In some instances, the index and/or barcode sequences may be arrayed according to an X/Y barcode scheme.

In some embodiments, an X/Y barcode scheme may be employed in which each column (X) and row (Y) of a multi-well array is identified by a unique barcode. In such embodiments, the first and/or second oligonucleotides or pairs thereof are provided with the suitable column and row barcodes such that individual wells may be identified based on the combination of X and Y barcodes. Using such a scheme, each individual well is identified by a unique barcode identifier signifying its column and row in the array. In some embodiments, this system allows unique identifiers applied to nucleic acids within the wells, while minimizing the number of barcoded primers required. For example, 144 barcodes (72 X barcodes and 72 Y barcodes) allow for unique identification of 5184 wells on a 72×72 array.

In some embodiments, in addition to the X/Y barcodes, nucleic acids may be labeled (e.g., via reverse transcription, amplification, template switching, etc.) with one or more of: a unique molecular identifier sequence (e.g., a molecule specific tag), one or more sequencing sequences, etc.

Any suitable reaction vessel(s) may be employed in the subject kits or devices and/or to contain a subject composition. Useful reaction vessels include but are not limited to e.g., tubes (e.g., single tubes, multi-tube strips, etc.), wells (e.g., of a multi-well plate (e.g., a 96-well plate, 384 well plate, or a plate with any number of wells such as 2000, 4000, 6000, or 10000 or more). Multi-well plates may be independent or may be part of a chip and/or device, e.g., as described in greater detail below.

As such, in certain embodiments, the reaction vessel employed is a well or wells of a multi-well device. The present disclosure is not limited by the type of multi-well devices (e.g., plates or chips) employed. In general, such devices have a plurality of wells that contain, or are dimensioned to contain, liquid (e.g., liquid that is trapped in the wells such that gravity alone cannot make the liquid flow out of the wells). One exemplary chip is the 5184-well SMART-CHIP™ sold by WAFERGEN™ (WaferGen Bio-systems, Inc.). Other exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY™ plates used in the QUANTSTUDIO™ real-time PCR system (sold by Applied Biosystems). Another exemplary multi-well device is a 96-well or 384-well plate.

The overall size of the multi-well devices may vary and it can range, for example, from a few microns to a few centimeters in thickness, and from a few millimeters to 50 centimeters in width or length. Typically, the size of the entire device ranges from about 10 mm to about 200 mm in width and/or length, and about 1 mm to about 10 mm in thickness. In some embodiments, the chip is about 40 mm in width by 40 mm in length by 3 mm in thickness.

The total number of wells (e.g., nanowells) on the multi-well device may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this disclosure are to be employed.

The present disclosure is not limited by the number of wells in the multi-well device or the number of wells in the multi-well source device. A large number of wells may be incorporated into a device. In various embodiments, the total number of wells on the device is from about 100 to about 200,000, or from about 5000 to about 10,000. In other embodiments the device comprises smaller chips, each of which comprises about 5,000 to about 20,000 wells. For example, a square chip may comprise 125 by 125 nanowells, with a diameter of 0.1 mm.

The wells (e.g., nanowells) in the multi-well devices may be fabricated in any convenient size, shape or volume. The wells may be about 100 μm to about 1 mm in length, about 100 μm to about 1 mm in width, and about 100 μm to about 5 mm or more in depth. In some instances, the wells may have a depth of 5 mm or less, including but not limited to e.g., 4 mm or less, 3 mm or less, 2 mm or less, 1 mm or less. In various embodiments, each nanowell has an aspect ratio (ratio of depth to width) of from about 1 to about 6 or more. In one embodiment, each nanowell has an aspect ratio of about 1:6. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 μl. The nanowell may have a volume of 1 μl or less, such as 500 nl or less. The volume may be 200 nl or less, including 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL™ siliconizing reagents, and SURFASIL™ siliconizing reagents. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a multi-well device, or will be able to ascertain such, without undue experimentation.

An exemplary multi-well device (e.g., chip) may have a thickness of about 0.625 mm, with a well have having dimensions of about 0.25 mm (250 um) in length and width. The nanowell depth can be about 0.525 mm (525 um), leaving about 0.1 mm of the chip beneath a given well. A nanowell opening can include any shape, such as round, square, rectangle or any other desired geometric shape. By way of example, a nanowell can include a diameter or width of between about 100 μm and about 1 mm, a pitch or length of between about 150 μm and about 1 mm and a depth of between about 10 μm to about 1 mm. The cavity of each well may take a variety of configurations. For instance, the cavity within a nanowell may be divided by linear or curved walls to form separate but adjacent compartments.

The wells (e.g., nanowells) of the multi-well device may be formed using, for example, commonly known photolithography techniques. The nanowells may be formed using a wet KOH etching technique, an anisotropic dry etching technique, mechanical drilling, injection molding and or thermo forming (e.g., hot embossing).

In addition to the above-mentioned components, a subject kit may further include instructions for using the components of the kit, e.g., to practice the subject methods as described above. The instructions are generally recorded on a suitable recording medium. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following example(s) is/are offered by way of illustration and not by way of limitation.

EXAMPLES

Example 1: Effect of De-Activatable and Activatable Primers in Reaction Mixtures The effect of the presence of the de-activatable and activatable primers in reaction mixtures was investigated. Examples of de-activatable RT-PCR primers, including a de-activatable first strand synthesis ("CDS") primer and a de-activatable template switching oligonucleotide (TSO) are provided in FIG. 4 and FIG. 5. Examples of index sequence-containing activatable primers are provided in FIG. 6 and FIG. 7.

The de-activatable primers tested contained ribonucleotides (see e.g., the underlined ribonucleotides in FIG. 4 and FIG. 5) that, when cleaved by RNase H generate primer fragments with low predicted Tm's. Thus, following deactivation of the de-activatable primers by RNase H, the primer fragments are predicted to not appreciably interfere with further templated elongation and/or nucleic acid amplification reactions. Specifically, the poly-dT first strand synthesis primer of FIG. 4 had a full-length Tm of 72.1° C. and the corresponding primer fragments after cleavage all have Tm's of 31° C. or less. Correspondingly, the Tm of the intact poly-dT primer is sufficient to prime first strand elongation but the Tm's of the primer fragments following cleavage are sufficiently low to prevent significant interference with downstream reactions. The de-activatable TSO of FIG. 5 similarly has a full length Tm of 70.1° C. and the post-cleavage fragments of the TSO following cleavage by RNase H have Tm's of 10.6° C. or less.

The activatable primers tested contained a stem-loop structure, which included a self-hybridizing stem region and an unpaired loop region, and an index sequencing adapter ("S502" in the activatable primer of FIG. 6 and "N701" in the activatable primer of FIG. 7). As depicted in FIG. 6 and FIG. 7, compared to the non-activatable versions, the activatable S502 and N701 primers contained additional nucleotide sequence that creates internal complementarity, thus the activatable primers formed stem-loop structures. Ribonucleotides present in the self-hybridizing stem region (identified by double-underline in FIG. 6 and FIG. 7) are cleaved by RNase H, destroying the stem-loop structures and generating primary activated primers (with Tm's of 62.6° C. and 59.4° C., respectively) and primer fragments having Tm's of 41.6° C. and below.

Figure 8:
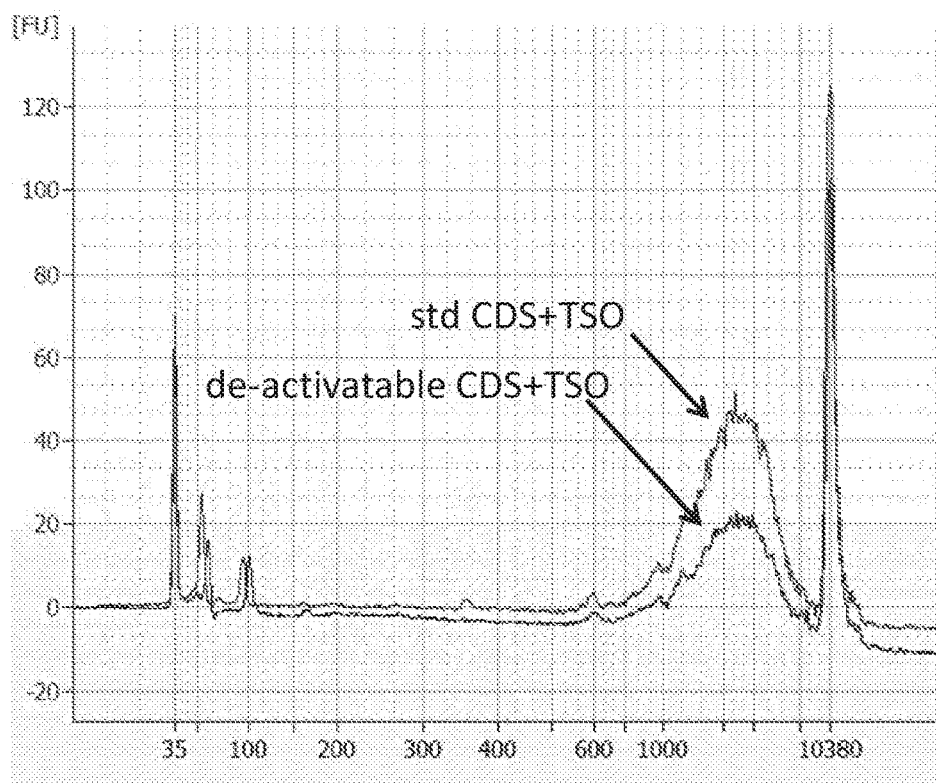
FIG. 8 demonstrates the ability to effectively synthesize cDNA using de-activatable primers/oligonucleotides.

The use of the de-activatable RT-PCR primers was tested in a one-step full-length library preparation reaction. No purification steps were employed. cDNA was synthesized from 10 pg of mouse brain total RNA using either the standard CDS primer and TSO or de-activatable CDS primer and de-activatable TSO. The synthesized cDNA in each condition was analyzed using a bioanalyzer and the resulting electropherograms are provided in FIG. 8. This analysis shows that the de-activatable primers/oligonucleotides efficiently produced cDNA in an RT-PCR reaction.

Figure 9:
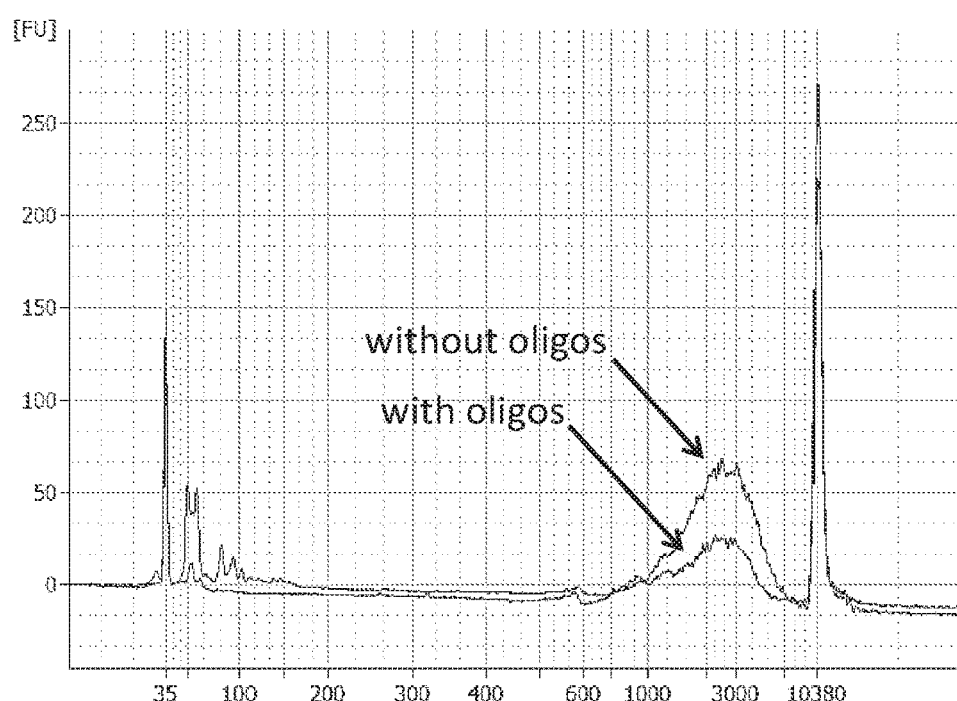
FIG. 9 demonstrates the ability to effectively synthesize cDNA in the presence of inactive activatable primers.

Whether the presence of activatable primers would impact cDNA synthesis was also tested. One-step RT-PCR was performed in the absence of (i.e., "without") and in the presence of (i.e., "with") activatable index oligonucleotides. 10 μg of mouse brain total RNA was used for cDNA synthesis and the resulting cDNA was analyzed on a bioanalyzer. The produced electropherograms are provided in FIG. 9. This analysis revealed that cDNA synthesis may be performed in the presence of activatable primers and a sufficient yield of cDNA is generated.

Collectively, the above results demonstrate that RT-PCR reaction mixtures containing de-activatable RT-PCR primers and activatable downstream primers (e.g., activatable index oligonucleotides not involved in the initial RT-PCR reaction) effectively generate cDNA from RNA template.

Example 2: Deactivation and Activation of De-Activatable and Activatable Primers The deactivation and activation of the de-activatable and activatable primers described above, and any effects therefrom, were tested using RNase H as a common stimulus for activation/deactivation. The presence of CDS primer and TSO during library amplification from produced cDNA often generates high background amplification containing many amplification products that are not useful components of the library (i.e., junk libraries).

Figure 10:
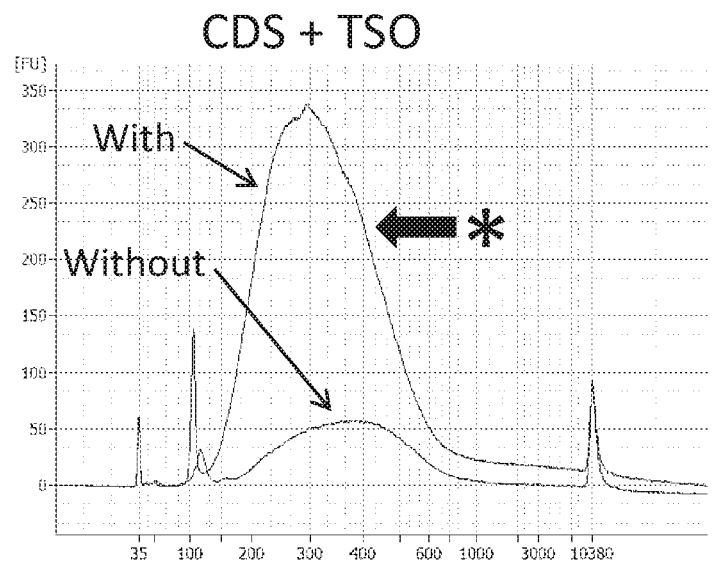
FIG. 10 demonstrates that library amplification, in the presence of CDS primers and TSO oligonucleotides, may generate undesirable background amplification.

To demonstrate this, one-step library preparation was performed using purified cDNA in the absence of (i.e., "without") and in the presence of (i.e., "with") CDS primer and TSO. The resulting electropherograms for each condition are provided in FIG. 10, showing the presence of high background ("*") when the reaction was performed with CDS primer and TSO present and the relative absence of such background when performed without.

Figure 11:
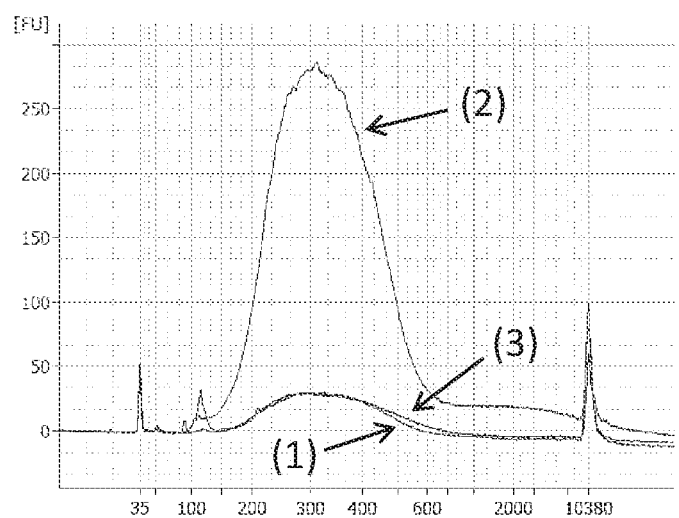
FIG. 11 demonstrates that the occurrence of background amplification can be reduced by deactivating both de-activatable CDS primers and TSO oligonucleotides.

This experiment was repeated using de-activatable CDS primer and de-activatable TSO. The conditions tested included: (1) in the absence of de-activatable CDS primer and TSO, (2) in the presence of de-activatable CDS primer and TSO, and (3) in the presence of de-activatable CDS primer and TSO with the addition of thermostable RNase H. The resulting electropherograms for each condition are provided in FIG. 11. These data show that de-activation of de-activatable CDS primer and TSO by RNase H reduces background amplification of junk libraries that may occur during one-step library preparation in the presence of un-cleaved CDS primer and TSO.

Figure 12:
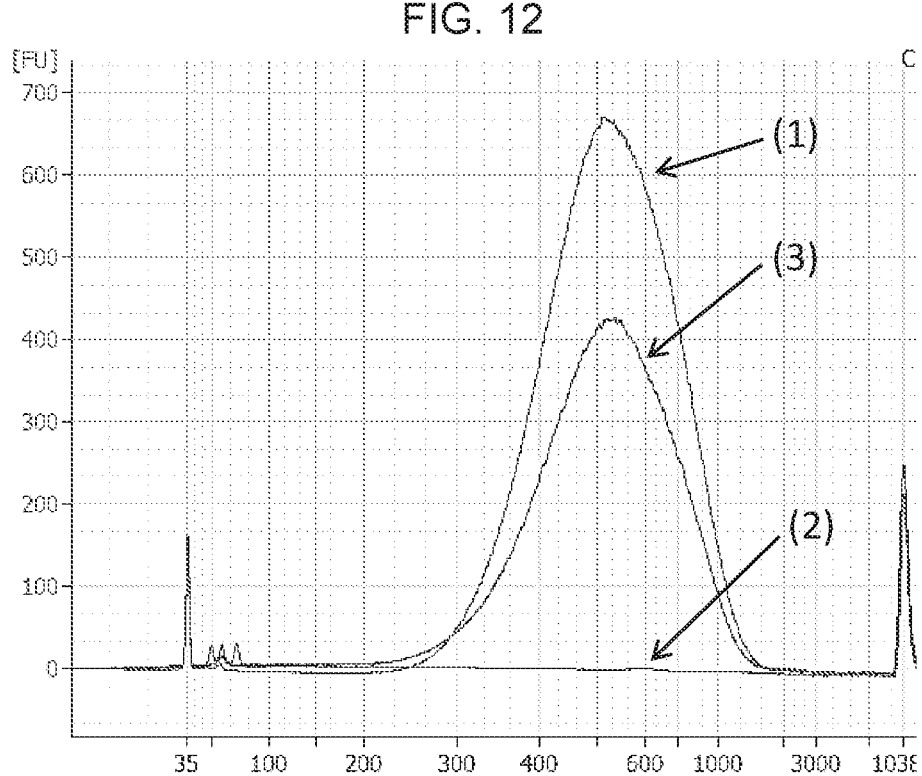
FIG. 12 demonstrates the effective activation of an activatable primer containing ribonucleotides through treatment with RNase H.

The ability to activate the activatable index oligonucleotide primers was also tested in the context of library amplification. A simple PCR test reaction was prepared containing SeqAmp™ polymerase (as sold by Takara Bio USA, Inc.), SeqAmp™ buffer (as sold by Takara Bio USA, Inc.) and an Illumina library. The PCR test reaction was subjected to amplification reaction conditions in the presence of: (1) standard oligonucleotides, (2) activatable oligonucleotides, or (3) activatable oligonucleotides with Tli RNase H2. The results of this assay are provided in FIG. 12.

This analysis demonstrated that, following activation with RNase H, the activatable index oligonucleotides provided for effective library amplification, whereas in the absence of RNase activation of the activatable index oligonucleotides no amplification occurred.

Collectively, these results demonstrate the effective activation of activatable primers/oligonucleotides and deactivation of de-activatable primers/oligonucleotides in relevant RT-PCR and library amplification reactions. The results also demonstrate that deactivation of de-activatable primers effectively represses unwanted background amplification. In addition, the above described examples, demonstrate the inactive nature of stem-loop containing activatable primers and the effective activation of such primers containing ribonucleotides through treatment with RNase H.

Example 3: Library Preparation Using De-Activatable First Strand Primer and Template Switching Oligonucleotide The workflow associated with this example is provided in FIG. 13. Cells in 1× phosphate buffered saline (PBS) were dispensed 1300 into, and lysed within, reaction vessels containing a de-activatable first strand primer (referred to as a de-activatable CDS primer). The de-activatable CDS primer included a poly d(T) with multiple uracil ribonucleotides interspaced throughout the poly d(T) as well as multiple additional ribonucleotides interspaced throughout the non-poly d(T) (i.e., the 5') portion of the de-activatable CDS primer.

The reverse-transcription polymerase chain reaction (RT-PCR) mixture was assembled by adding enzymes (i.e., Smartscribe, RNase inhibitor, and Terra DNA polymerase) and a de-activatable template switching oligonucleotide (TSO). The DNA-based de-activatable TSO included multiple ribonucleotides interspaced throughout. The RT-PCR reaction 1301 was maintained under suitable reaction conditions to generate cDNA with the de-activatable CDS and TSO serving as primers in the absence of Tli RNaseH2.

In the next step 1302 a P5 index sequence-containing primer was added. Tagmentation and deactivation of the de-activatable oligonucleotides were performed together 1303 by addition of Nextera Tn5 (AMT) (and associated reaction components), Terra DNA polymerase and Tli RNaseH2 to the reaction mixture while maintaining the reaction mixture under conditions sufficient for tagmentation to proceed. The de-activatable oligonucleotides were cleaved by Tli RNaseH2 and thus can no longer function as primers in the downstream reaction. Further amplification and addition of the P7 index was performed in the following step 1304 to generate a ready-for-sequencing product nucleic acid library where each amplicon contains both P5 and P7 adapter sequences.

Notwithstanding the appended claims, the disclosure is also defined by the following clauses:

1. A method comprising:
combining a template nucleic acid, a de-activatable oligonucleotide, and an activatable oligonucleotide into an initial reaction mixture;
maintaining the initial reaction mixture under conditions sufficient to elongate the de-activatable oligonucleotide via a template nucleic acid-mediated primer extension reaction to produce an intermediate reaction mixture comprising an intermediate nucleic acid;
exposing the intermediate reaction mixture to a deactivating stimulus that deactivates the de-activatable oligonucleotide and an activating stimulus that activates the activatable oligonucleotide to produce a final reaction mixture; and
subjecting the final reaction mixture to conditions sufficient to elongate the activated activatable oligonucleotide via an intermediate nucleic acid template-mediated primer extension reaction to produce a product nucleic acid.

2. The method according to Clause 1, wherein the deactivating stimulus, the activating stimulus or both stimuli are enzymes.

3. The method according to Clause 2, wherein at least one enzyme is a nuclease.

4. The method according to Clause 3, wherein the nuclease is ribonuclease H (RNase H).

5. The method according to Clause 1, wherein the deactivating stimulus, the activating stimulus or both stimuli are chemical agents.

6. The method according to Clause 5, wherein at least one chemical agent cleaves a selectively cleavable linkage present in the activatable oligonucleotide and a selectively cleavable linkage present in the de-activatable oligonucleotide or selectively cleavable linkages present in both the activatable oligonucleotide and the de-activatable oligonucleotide.

7. The method according to Clause 1, wherein the deactivating stimulus, the activating stimulus or both stimuli are electromagnetic stimuli.

8. The method according to Clause 7, wherein at least one electromagnetic stimulus is light.

9. The method according to Clause 7, wherein at least one electromagnetic stimulus is heat.

10. The method according to any of the preceding Clauses, wherein the deactivating stimulus and the activating stimulus are the same stimulus.

11. The method according to any of the previous Clauses, wherein the de-activatable oligonucleotide comprises a cleavable-base.

12. The method according to Clause 11, wherein the de-activatable oligonucleotide comprises two or more cleavable-bases separated by at least one deoxyribonucleotide.

13. The method according to Clause 12, wherein the two or more cleavable-bases are each separated by a continuous stretch of deoxyribonucleotides ranging from 2 nt to 20 nt in length.

14. The method according to any of Clauses 11 to 13, wherein the cleavable-base is a ribonucleotide.

15. The method according to any of the previous Clauses, wherein the activatable oligonucleotide comprises a stem-loop comprising a self-hybridizing stem region and an unpaired loop region.

16. The method according to Clause 15, wherein the self-hybridizing stem region is 10 nt to 50 nt in length.

17. The method according to Clauses 15 or 16, wherein the unpaired loop region is 4 nt to 30 nt in length.

18. The method according to any of Clauses 15 to 17, wherein the stem-loop comprises a cleavable-base.

19. The method according to Clause 18, wherein the cleavable-base is present in the self-hybridizing stem region.

20. The method according to Clause 19, wherein the self-hybridizing stem region comprises two or more cleavable-bases separated by at least one deoxyribonucleotide.

21. The method according to Clause 20, wherein the two or more cleavable-bases are each separated by a continuous stretch of deoxyribonucleotides ranging from 2 nt to 20 nt in length.

22. The method according to any of Clauses 15 to 21, wherein the cleavable-base is a ribonucleotide.

23. The method according to any of Clauses 10 to 22, wherein the de-activatable oligonucleotide comprises two or more ribonucleotides separated by at least one deoxyribonucleotide, the activatable oligonucleotide comprises a stem-loop comprising a self-hybridizing stem region comprising two or more ribonucleotides separated by at least one deoxyribonucleotide and the stimulus is RNase H.

24. The method according to any of the previous Clauses, wherein the activatable oligonucleotide, the de-activatable oligonucleotide or both comprise an adapter sequence.

25. The method according to any of the previous Clauses, wherein the activatable primer, the de-activatable oligonucleotide or both comprise a barcode sequence.

26. The method according to any of the previous Clauses, wherein the activatable primer, the de-activatable oligonucleotide or both comprise a unique molecular identifier (UMI).

27. The method according to any of the previous Clauses, wherein the de-activatable oligonucleotide is a template switching oligonucleotide.

28. The method according to any of the previous Clauses, wherein the de-activatable oligonucleotide is a de-activatable primer and the template nucleic acid-mediated primer extension reaction comprises maintaining the initial reaction mixture under conditions sufficient to elongate the de-activatable primer.

29. The method according to any of the previous Clauses, wherein the de-activatable oligonucleotide is a reverse transcription polymerase chain reaction (RT-PCR) primer.

30. The method according to Clause 29, wherein the de-activatable oligonucleotide is a first strand synthesis primer.

31. The method according to any of the previous Clauses, wherein the template nucleic acid is a RNA template nucleic acid.

32. The method according to Clause 31, wherein the RNA template nucleic acid is a messenger RNA (mRNA).

33. The method according to Clause 32, wherein the intermediate nucleic acid comprises a reverse transcribed first strand complementary DNA (cDNA) and the method comprises subjecting the final reaction mixture to conditions sufficient to amplify the first strand cDNA via a polymerase chain reaction using the activated activatable oligonucleotide.

34. The method according to any of Clauses 1 to 28, wherein the template nucleic acid is a DNA template nucleic acid.

35. The method according to any of the previous Clauses, wherein the activatable oligonucleotide comprises a sequence identical to a sequence present in the de-activatable oligonucleotide.

36. The method according to Clause 35, wherein the identical sequence is 10 nt to 100 nt in length.

37. The method according to any of the previous Clauses, wherein the activatable oligonucleotide comprises a sequence complementary to a sequence present in the de-activatable oligonucleotide.

38. The method according to Clause 37, wherein the complementary sequence is 10 nt to 100 nt in length.

39. The method according to any of the previous Clauses, wherein the method further comprises amplifying the intermediate nucleic acid using the de-activatable oligonucleotide.

40. The method according to any of the previous Clauses, wherein the method further comprises amplifying the product nucleic acid using the activated activatable oligonucleotide.

41. The method according to any of the previous Clauses, wherein the method further comprises sequencing the product nucleic acid or an amplification product thereof.

42. The method according to any of the previous Clauses, wherein the initial reaction mixture comprises template nucleic acid from only one cell.

43. The method according to any of the previous Clauses, wherein the method is performed in a single reaction vessel.

44. The method according to Clause 43, wherein the single reaction vessel comprises the de-activatable oligonucleotide and the activatable oligonucleotide prior to the combining.

45. The method according to Clause 44, wherein the de-activatable oligonucleotide and the activatable oligonucleotide are lyophilized.

46. The method according to Clause 44, wherein the de-activatable oligonucleotide and the activatable oligonucleotide are present in one or more droplets.

47. The method according to any of Clauses 43 to 46, wherein the method further comprises obtaining the template nucleic acid by lysing a single cell in the single reaction vessel.

48. A kit comprising a de-activatable oligonucleotide that is deactivated by a deactivating stimulus and an activatable oligonucleotide that is activated by an activating stimulus.

49. The kit according to Clause 48, wherein the de-activatable oligonucleotide, the activatable oligonucleotide or both comprise a specific enzymatically cleavable linkage.

50. The kit according to Clause 49, wherein the specific enzymatically cleavable linkage is an internucleotide linkage or a 3'-linkage.

51. The kit according to Clause 50, wherein the specific enzymatically cleavable linkage is an internucleotide linkage between a deoxyribonucleotide and a ribonucleotide.

52. The kit according to any of Clauses 48 to 51, wherein the de-activatable oligonucleotide, the activatable oligonucleotide or both comprise a specific chemically cleavable linkage.

53. The kit according to Clause 52, wherein the specific chemically cleavable linkage is an internucleotide linkage or a 3'-linkage.

54. The kit according to any of Clauses 48 to 53, wherein the de-activatable oligonucleotide, the activatable oligonucleotide or both comprise a specific electromagnetically-labile linkage.

55. The kit according to Clause 54, wherein the specific electromagnetically-labile linkage is an internucleotide linkage or a 3'-linkage.

56. The kit according to Clauses 54 or 55, wherein the specific electromagnetically-labile linkage is light-labile.

57. The kit according to Clauses 54 or 55, wherein the specific electromagnetically-labile linkage is heat-labile.

58. The kit according to any of Clauses 48 to 57, wherein the deactivating stimulus and the activating stimulus are the same stimulus.

59. The kit according to any of Clauses 48 to 58, wherein the de-activatable oligonucleotide comprises two or more cleavable-bases separated by at least one deoxyribonucleotide.

60. The kit according to Clause 59, wherein the two or more cleavable-bases are each separated by a continuous stretch of deoxyribonucleotides ranging from 2 nt to 20 nt in length.

61. The kit according to Clauses 59 or 60, wherein the cleavable-base is a ribonucleotide.

62. The kit according to any of Clauses 48 to 61, wherein the activatable oligonucleotide comprises a stem-loop comprising a self-hybridizing stem region and an unpaired loop region.

63. The kit according to Clause 62, wherein the self-hybridizing stem region is 10 nt to 50 nt in length.
64. The kit according to Clauses 62 or 63, wherein the unpaired loop region is 4 nt to 30 nt in length.
65. The kit according to any of Clauses 62 to 64, wherein the stem-loop comprises a cleavable-base.
66. The kit according to Clause 65, wherein the cleavable-base is present in the self-hybridizing stem region.
67. The kit according to Clause 66, wherein the self-hybridizing stem region comprises two or more cleavable-bases separated by at least one deoxyribonucleotide.
68. The kit according to Clause 67, wherein the two or more cleavable-bases are each separated by a continuous stretch of deoxyribonucleotides ranging from 2 nt to 20 nt in length.
69. The kit according to any of Clauses 65 to 68, wherein the cleavable-base is a ribonucleotide.
70. The kit according to any of Clauses 48 to 69, wherein the activatable oligonucleotide, the de-activatable oligonucleotide or both comprise an adapter sequence.
71. The kit according to any of Clauses 48 to 70, wherein the activatable oligonucleotide, the de-activatable oligonucleotide or both comprise a barcode sequence.
72. The kit according to any of Clauses 48 to 71, wherein the activatable oligonucleotide, the de-activatable oligonucleotide or both comprise unique molecular identifier (UMI).
73. The kit according to any of Clauses 48 to 72, wherein the de-activatable oligonucleotide is a template switching oligonucleotide.
74. The kit according to any of Clauses 48 to 72, wherein the de-activatable oligonucleotide is a de-activatable primer.
75. The kit according to Clause 74, wherein the de-activatable oligonucleotide is a reverse transcription polymerase chain reaction (RT-PCR) primer.
76. The kit according to Clause 75, wherein the de-activatable oligonucleotide is a first strand synthesis primer.
77. The kit according to any of Clauses 48 to 76, wherein the activatable oligonucleotide comprises a sequence identical to a sequence present in the de-activatable oligonucleotide.
78. The kit according to Clause 77, wherein the identical sequence is 10 nt to 100 nt in length.
79. The kit according to any of Clauses 48 to 78, wherein the activatable oligonucleotide comprises a sequence complementary to a sequence present in the de-activatable oligonucleotide.
80. The kit according to Clause 79, wherein the complementary sequence is 10 nt to 100 nt in length.
81. The kit according to any of Clauses 48 to 80, wherein the kit further comprises the deactivating stimulus, the activating stimulus or both.
82. The kit according to Clause 81, wherein the deactivating stimulus, the activating stimulus or both are enzymes.
83. The kit according to Clause 82, wherein at least one enzyme is a nuclease.
84. The kit according to Clause 83, wherein the nuclease is ribonuclease H (RNase H) and the de-activatable oligonucleotide comprises two or more ribonucleotides separated by at least one deoxyribonucleotide or the activatable oligonucleotide comprises a stem-loop comprising a self-hybridizing stem region comprising two or more ribonucleotides separated by at least one deoxyribonucleotide.
85. The kit according to any of Clauses 48 to 84, wherein the de-activatable oligonucleotide comprises two or more ribonucleotides separated by at least one deoxyribonucleotide and the activatable oligonucleotide comprises a stem-loop comprising a self-hybridizing stem region comprising two or more ribonucleotides separated by at least one deoxyribonucleotide.
86. The kit according to any of Clauses 48 to 85, wherein the deactivating stimulus, the activating stimulus or both are chemical agents.
87. The kit according to any of Clauses 48 to 86, wherein the kit further comprises a stimulus-generating device.
88. The kit according to Clause 87, wherein the stimulus-generating device is a light generating device.
89. The kit according to Clauses 87 or 88, wherein the stimulus-generating device is a heat generating device.
90. The kit according to any of Clauses 48 to 89, wherein the kit further comprises a polymerase.
91. The kit according to Clause 90, wherein the polymerase is a reverse transcriptase.
92. The kit according to Clauses 90 or 91, wherein the polymerase has template-switching activity.
93. The kit according to any of Clauses 48 to 92, wherein the de-activatable oligonucleotide and the activatable oligonucleotide are both present in a single vessel.
94. The kit according to Clause 93, wherein the kit further comprises a plurality of single vessels each containing a de-activatable oligonucleotide and an activatable oligonucleotide.
95. The kit according to Clause 94, wherein the de-activatable oligonucleotide present in each vessel of the plurality comprises a unique sequence.
96. The kit according to Clauses 94 or 95, wherein the activatable oligonucleotide present in each vessel of the plurality comprises a unique sequence.
97. The kit according to any of Clauses 93 to 96, wherein the single vessel is a well of a multi-well plate.
98. A method comprising:
    combining a template nucleic acid and a de-activatable oligonucleotide into a reaction mixture;
    maintaining the reaction mixture under conditions sufficient to elongate the de-activatable oligonucleotide via a template nucleic acid-mediated primer extension reaction to produce a reaction mixture comprising an extended nucleic acid;
    exposing the reaction mixture comprising the extended nucleic acid to a deactivating stimulus that deactivates the de-activatable oligonucleotide to produce a stimulus-exposed reaction mixture; and
    subjecting the stimulus-exposed reaction mixture to conditions sufficient to produce a product nucleic acid.
99. The method according to Clause 98, wherein a template switching oligonucleotide (TSO) is combined into the reaction mixture and the extended nucleic acid produced comprises a sequence complementary to the TSO.
100. The method according to Clause 99, wherein the TSO is de-activatable.
101. The method according to any of Clauses 98 to 100, wherein the deactivating stimulus is an enzyme.
102. The method according to Clause 101, wherein the enzyme is a nuclease.
103. The method according to Clause 102, wherein the nuclease is ribonuclease H (RNase H).
104. The method according to any of Clauses 101 to 103, wherein the enzyme is thermostable.
105. The method according to any of Clauses 98 to 100, wherein the deactivating stimulus is a chemical agent.
106. The method according to Clause 105, wherein the chemical agent cleaves a selectively cleavable linkage present in the de-activatable oligonucleotide.
107. The method according to any of Clauses 98 to 100, wherein the deactivating stimulus is an electromagnetic stimulus.

108. The method according to Clause 107, wherein the electromagnetic stimulus is light.

109. The method according to Clause 107, wherein the electromagnetic stimulus is heat.

110. The method according to any of Clauses 98 to 109, wherein the de-activatable oligonucleotide comprises a cleavable-base.

111. The method according to Clause 110, wherein the de-activatable oligonucleotide comprises two or more cleavable-bases separated by at least one deoxyribonucleotide.

112. The method according to Clause 111, wherein the two or more cleavable-bases are each separated by a continuous stretch of deoxyribonucleotides ranging from 2 nt to 20 nt in length.

113. The method according to any of Clauses 110 to 112, wherein the cleavable-base is a ribonucleotide.

114. The method according to any of Clause 98 to 113, wherein the de-activatable oligonucleotide comprises an adapter sequence.

115. The method according to any of Clause 98 to 114, wherein the de-activatable oligonucleotide comprises a barcode sequence.

116. The method according to any of Clauses 98 to 115, wherein the de-activatable oligonucleotide comprises a unique molecular identifier (UMI).

117. The method according to any of Clauses 98 to 116, wherein the method comprises a de-activatable oligonucleotide that is a de-activatable primer and the template nucleic acid-mediated primer extension reaction comprises maintaining the initial reaction mixture under conditions sufficient to elongate the de-activatable primer.

118. The method according to Clause 117, wherein the de-activatable primer is a reverse transcription polymerase chain reaction (RT-PCR) primer.

119. The method according to Clause 118, wherein the de-activatable primer is a first strand synthesis primer.

120. The method according to any of Clauses 98 to 119, wherein the template nucleic acid is a RNA template nucleic acid.

121. The method according to Clause 120, wherein the RNA template nucleic acid is a messenger RNA (mRNA).

122. The method according to Clause 121, wherein the extended nucleic acid comprises a reverse transcribed first strand complementary DNA (cDNA) and the method comprises subjecting the stimulus-exposed reaction mixture to conditions sufficient to amplify the first strand cDNA via a polymerase chain reaction using at least one primer.

123. The method according to any of Clauses 98 to 117, wherein the template nucleic acid is a DNA template nucleic acid.

124. The method according to any of Clauses 98 to 123, wherein the method further comprises amplifying the extended nucleic acid using the de-activatable oligonucleotide.

125. The method according to any of Clauses 98 to 124, comprising combining the template nucleic acid and at least two different de-activatable oligonucleotides into the initial reaction mixture.

126. The method according to Clause 125, wherein the at least two different de-activatable oligonucleotides are deactivated by the same stimulus.

127. The method according to Clause 125, wherein the at least two different de-activatable oligonucleotides are deactivated by at least two different stimuli.

128. The method according to any of Clauses 125 to 127, wherein the at least two different de-activatable oligonucleotides comprise a de-activatable template switching oligonucleotide and de-activatable primer.

129. The method according to Clause 128, wherein the de-activatable primer is a RT-PCR primer.

130. The method according to Clause 129, wherein the RT-PCR primer is a first strand synthesis primer.

131. The method according to any of Clauses 98 to 130, wherein the reaction mixture into which the template nucleic acid and the de-activatable oligonucleotide are combined comprises an RNase inhibitor.

132. The method according to any of Clauses 98 to 131, wherein the reaction mixture into which the template nucleic acid and the de-activatable oligonucleotide are combined comprises a reverse transcriptase and a DNA polymerase.

133. The method according to Clause 132, wherein the DNA polymerase is a thermostable DNA polymerase.

134. The method according to any of Clauses 98 to 133, wherein a primer is added to the reaction mixture comprising the extended nucleic acid and the reaction mixture comprising the extended nucleic acid is maintained under conditions sufficient to amplify the extended nucleic acid using the primer prior to deactivating the de-activatable oligonucleotide.

135. The method according to Clause 134, wherein the primer comprises a sequencing platform adapter construct domain.

136. The method according to Clause 135, wherein the sequencing platform adapter construct domain comprises a P5 adapter sequence.

137. The method according to any of Clauses 98 to 136, wherein the method comprises subjecting the stimulus-exposed reaction mixture to a tagmentation reaction to produce the product nucleic acid.

138. The method according to any of Clauses 98 to 137, wherein a primer is added to the stimulus-exposed reaction mixture and the stimulus-exposed reaction mixture is maintained under conditions sufficient to amplify the product nucleic acid using the primer.

139. The method according to Clause 138, wherein the primer comprises a sequencing platform adapter construct domain.

140. The method according to Clause 139, wherein the sequencing platform adapter construct domain comprises a P7 adapter sequence.

141. The method according to any of Clauses 98 to 140, wherein the method further comprises:
  combining an activatable oligonucleotide into the reaction mixture; and
  exposing the reaction mixture comprising the extended nucleic acid to an activating stimulus that activates the activatable oligonucleotide.

142. The method according to Clause 141, wherein the stimulus that activates the activatable oligonucleotide is the same stimulus that deactivates the de-activatable oligonucleotide.

143. The method according to any of Clauses 98 to 142, wherein the method further comprises sequencing the product nucleic acid or an amplification product thereof.

144. The method according to any of Clauses 98 to 143, wherein the template nucleic acid combined into the reaction mixture comprises template nucleic acid from only one cell.

145. The method according to any of Clauses 98 to 144, wherein the method is performed in a single reaction vessel.

146. The method according to Clause 145, wherein the single reaction vessel comprises the de-activatable oligonucleotide prior to the combining.

147. The method according to Clause 146, wherein the de-activatable oligonucleotide is lyophilized.
148. The method according to Clause 146, wherein the de-activatable oligonucleotide is present in one or more droplets.
149. The method according to any of Clauses 144 to 148, wherein the method further comprises obtaining the template nucleic acid by lysing a single cell in the single reaction vessel.
150. A kit comprising a de-activatable template switching oligonucleotide that is deactivated by a first stimulus and a de-activatable primer that is deactivated by a second stimulus.
151. The kit according to Clause 150, wherein the first and second stimuli are the same.
152. The kit according to Clause 150, wherein the first and second stimuli are different.
153. The kit according to any of Clauses 150 to 152, wherein the kit further comprises the first, the second or both stimuli or a device that generates the first, the second or both stimuli.
154. The kit according to any of Clauses 150 to 153, wherein the first and second stimuli are selected from the group consisting of: an enzymatic stimulus, a chemical stimulus and an electromagnetic stimulus.
155. The kit according to Clause 154, wherein the first stimulus, the second stimulus or both are a nuclease.
156. The kit according to Clause 155, wherein the nuclease is an RNase H.
157. The kit according to any of Clauses 150 to 156, wherein the de-activatable primer is a de-activatable first strand primer.
158. The kit according to any of Clauses 150 to 157, wherein the kit further comprises a primer that specifically hybridizes to a primer binding site present on the de-activatable template switching oligonucleotide or the de-activatable primer.
159. The kit according to Clause 158, wherein the primer comprises a non-templated sequence.
160. The kit according to Clause 159, wherein the non-templated sequence comprises an adapter sequence,
161. The kit according to any of Clauses 150 to 160, wherein the kit further comprises at least one polymerase.
162. The kit according to Clause 161, wherein the at least one polymerase comprises a reverse transcriptase.
163. The kit according to Clauses 161 or 162, wherein the at least one polymerase comprises a DNA polymerase.
164. The kit according to any of Clauses 150 to 163, wherein the kit further comprises an RNase inhibitor.
165. The kit according to any of Clauses 150 to 164, wherein the kit further comprises one or more components for performing a tagmentation reaction.
166. The kit according to Clause 165, wherein the kit further comprises a primer that specifically hybridizes to a primer binding site present on a component of the tagmentation reaction.
167. The kit according to Clause 166, wherein the primer comprises a non-templated sequence.
168. The kit according to Clause 167, wherein the non-templated sequence comprises an adapter sequence.
169. A method comprising:
combining a template nucleic acid, a de-activatable oligonucleotide, and an activatable oligonucleotide into a reaction mixture;
maintaining the reaction mixture under conditions sufficient to elongate the de-activatable oligonucleotide via a template nucleic acid-mediated primer extension reaction to produce a reaction mixture comprising an extended nucleic acid;
exposing the reaction mixture comprising the extended nucleic acid to a deactivating stimulus that deactivates the de-activatable oligonucleotide and an activating stimulus that activates the activatable oligonucleotide to produce a stimulus-exposed reaction mixture; and
subjecting the stimulus-exposed reaction mixture to conditions sufficient to elongate the activated activatable oligonucleotide via a primer extension reaction templated by the extended nucleic acid to produce a product nucleic acid.
170. The method according to Clause 169, wherein the deactivating stimulus, the activating stimulus or both stimuli are enzymes.
171. The method according to Clause 170, wherein at least one enzyme is a nuclease.
172. The method according to Clause 171, wherein the nuclease is ribonuclease H (RNase H).
173. The method according to Clause 169, wherein the deactivating stimulus, the activating stimulus or both stimuli are chemical agents.
174. The method according to Clause 173, wherein at least one chemical agent cleaves a selectively cleavable linkage present in the activatable oligonucleotide and a selectively cleavable linkage present in the de-activatable oligonucleotide or selectively cleavable linkages present in both the activatable oligonucleotide and the de-activatable oligonucleotide.
175. The method according to Clause 169, wherein the deactivating stimulus, the activating stimulus or both stimuli are electromagnetic stimuli.
176. The method according to Clause 175, wherein at least one electromagnetic stimulus is light.
177. The method according to Clause 175, wherein at least one electromagnetic stimulus is heat.
178. The method according to any of Clauses 169 to 177, wherein the deactivating stimulus and the activating stimulus are the same stimulus.
179. The method according to any of Clauses 169 to 178, wherein the de-activatable oligonucleotide comprises a cleavable-base.
180. The method according to Clause 179, wherein the de-activatable oligonucleotide comprises two or more cleavable-bases separated by at least one deoxyribonucleotide.
181. The method according to Clause 180, wherein the two or more cleavable-bases are each separated by a continuous stretch of deoxyribonucleotides ranging from 2 nt to 20 nt in length.
182. The method according to any of Clauses 179 to 181, wherein the cleavable-base is a ribonucleotide.
183. The method according to any of Clauses 169 to 182, wherein the activatable oligonucleotide comprises a stem-loop comprising a self-hybridizing stem region and an unpaired loop region.
184. The method according to Clause 183, wherein the self-hybridizing stem region is 10 nt to 50 nt in length.
185. The method according to Clauses 183 or 184, wherein the unpaired loop region is 4 nt to 30 nt in length.
186. The method according to any of Clauses 183 to 185, wherein the stem-loop comprises a cleavable-base.
187. The method according to Clause 186, wherein the cleavable-base is present in the self-hybridizing stem region.
188. The method according to Clause 187, wherein the self-hybridizing stem region comprises two or more cleavable-bases separated by at least one deoxyribonucleotide.

189. The method according to Clause 188, wherein the two or more cleavable-bases are each separated by a continuous stretch of deoxyribonucleotides ranging from 2 nt to 20 nt in length.
190. The method according to any of Clauses 186 to 189, wherein the cleavable-base is a ribonucleotide.
191. The method according to any of Clauses 178 to 190, wherein the de-activatable oligonucleotide comprises two or more ribonucleotides separated by at least one deoxyribonucleotide, the activatable oligonucleotide comprises a stem-loop comprising a self-hybridizing stem region comprising two or more ribonucleotides separated by at least one deoxyribonucleotide and the stimulus is RNase H.
192. The method according to any of Clauses 169 to 191, wherein the activatable oligonucleotide, the de-activatable oligonucleotide or both comprise an adapter sequence.
193. The method according to any of Clauses 169 to 192, wherein the activatable primer, the de-activatable oligonucleotide or both comprise a barcode sequence.
194. The method according to any of Clauses 169 to 193, wherein the activatable primer, the de-activatable oligonucleotide or both comprise a unique molecular identifier (UMI).
195. The method according to any of Clauses 169 to 195, wherein the de-activatable oligonucleotide is a template switching oligonucleotide.
196. The method according to any of Clauses 169 to 195, wherein the de-activatable oligonucleotide is a de-activatable primer and the template nucleic acid-mediated primer extension reaction comprises maintaining the reaction mixture under conditions sufficient to elongate the de-activatable primer.
197. The method according to any of Clauses 169 to 196, wherein the de-activatable oligonucleotide is a reverse transcription polymerase chain reaction (RT-PCR) primer.
198. The method according to Clause 197, wherein the de-activatable oligonucleotide is a first strand synthesis primer.
199. The method according to any of Clauses 169 to 198, wherein the template nucleic acid is a RNA template nucleic acid.
200. The method according to Clause 199, wherein the RNA template nucleic acid is a messenger RNA (mRNA).
201. The method according to Clause 200, wherein the extended nucleic acid comprises a reverse transcribed first strand complementary DNA (cDNA) and the method comprises subjecting the stimulus-exposed reaction mixture to conditions sufficient to amplify the first strand cDNA via a polymerase chain reaction using the activated activatable oligonucleotide.
202. The method according to any of Clauses 169 to 28, wherein the template nucleic acid is a DNA template nucleic acid.
203. The method according to any of Clauses 169 to 196, wherein the activatable oligonucleotide comprises a sequence identical to a sequence present in the de-activatable oligonucleotide.
204. The method according to Clause 203, wherein the identical sequence is 10 nt to 100 nt in length.
205. The method according to any of Clauses 169 to 204, wherein the activatable oligonucleotide comprises a sequence complementary to a sequence present in the de-activatable oligonucleotide.
206. The method according to Clause 205, wherein the complementary sequence is 10 nt to 100 nt in length.
207. The method according to any of Clauses 169 to 206, wherein the method further comprises amplifying the extended nucleic acid using the de-activatable oligonucleotide.
208. The method according to any of Clauses 169 to 207, wherein the method further comprises amplifying the product nucleic acid using the activated activatable oligonucleotide.
209. The method according to any of Clauses 169 to 208, wherein the method further comprises sequencing the product nucleic acid or an amplification product thereof.
210. The method according to any of Clauses 169 to 209, wherein the template nucleic acid is from only one cell.
211. The method according to any of Clauses 169 to 210, wherein the method is performed in a single reaction vessel.
212. The method according to Clause 211, wherein the single reaction vessel comprises the de-activatable oligonucleotide and the activatable oligonucleotide prior to the combining.
213. The method according to Clause 212, wherein the de-activatable oligonucleotide and the activatable oligonucleotide are lyophilized.
214. The method according to Clause 212, wherein the de-activatable oligonucleotide and the activatable oligonucleotide are present in one or more droplets.
215. The method according to any of Clauses 211 to 214, wherein the method further comprises obtaining the template nucleic acid by lysing a single cell in the single reaction vessel.
216. A method comprising:
  elongating a de-activatable oligonucleotide via a template nucleic acid-mediated primer extension reaction to produce an extended nucleic acid; and
  deactivating the de-activatable oligonucleotide.
217. The method according to Clause 216, wherein deactivating the de-activatable oligonucleotide comprises applying a deactivating stimulus selected from the group consisting of: an enzyme, a chemical agent and an electromagnetic stimulus.
218. The method according to Clauses 216 or 217, comprising a template switching reaction comprising a template switching oligonucleotide (TSO) to produce an extended nucleic acid that comprises a sequence complementary to the TSO.
219. The method according to Clause 218, wherein the TSO is de-activatable.
220. The method according to Clause 219, wherein the de-activatable oligonucleotide and the de-activatable TSO are deactivated by the same stimulus.
221. The method according to any of Clauses 217 to 220, wherein the deactivating stimulus is an enzyme
222. The method according to Clause 221, wherein the enzyme is a nuclease.
223. The method according to Clause 222, wherein the nuclease is ribonuclease H (RNase H).
224. The method according to any of Clauses 217 to 223, wherein the enzyme is thermostable.
225. The method according to any of Clauses 217 to 220, wherein the deactivating stimulus is a chemical agent.
226. The method according to Claus 225, wherein the chemical agent cleaves a selectively cleavable linkage present in the de-activatable oligonucleotide.
227. The method according to any of Clauses 217 to 220, wherein the deactivating stimulus is an electromagnetic stimulus.
228. The method according to Clause 227, wherein the electromagnetic stimulus is light.

229. The method according to Clause 227, wherein the electromagnetic stimulus is heat.
230. The method according to any of Clauses 216 to 229, wherein the de-activatable oligonucleotide comprises a cleavable-base.
231. The method according to Clause 230, wherein the de-activatable oligonucleotide comprises two or more cleavable-bases separated by at least one deoxyribonucleotide.
232. The method according to Clause 231, wherein the two or more cleavable-bases are each separated by a continuous stretch of deoxyribonucleotides ranging from 2 nt to 20 nt in length.
233. The method according to any of Clauses 230 to 232, wherein the cleavable-base is a ribonucleotide.
234. The method according to any of Clause 216 to 233, wherein the de-activatable oligonucleotide comprises an adapter sequence.
235. The method according to any of Clauses 216 to 234, wherein the de-activatable oligonucleotide comprises a barcode sequence.
236. The method according to any of Clauses 216 to 235, wherein the de-activatable oligonucleotide comprises a unique molecular identifier (UMI).
237. The method according to any of Clauses 216 to 236, wherein the de-activatable oligonucleotide is a reverse transcription polymerase chain reaction (RT-PCR) primer.
238. The method according to Clause 237, wherein the de-activatable primer is a first strand synthesis primer.
239. The method according to any of Clauses 216 to 238, wherein the template nucleic acid-mediated primer extension reaction is a RT-PCR reaction.
240. The method according to Clause 239, wherein the extended nucleic acid comprises a reverse transcribed first strand complementary DNA (cDNA).
241. The method according to any of Clauses 216 to 240, wherein the method further comprises an amplification reaction.
242. The method according to Clause 241, wherein the amplification reaction comprises amplifying the extended nucleic acid.
243. The method according to any of Clauses 216 to 242, wherein the method further comprises a tagmentation reaction.
244. The method according to any of Clauses 241 to 243, wherein the method further comprises sequencing an amplification product of the amplification reaction.
245. The method according to any of Clauses 216 to 244, wherein the template nucleic acid-mediated primer extension reaction is a single cell reaction.
246. The method according to any of Clauses 216 to 245, wherein the method is performed in a single reaction vessel.
247. The method according to Clause 246, wherein the single reaction vessel comprises the de-activatable oligonucleotide prior to the elongating.
248. The method according to Clause 247, wherein the de-activatable oligonucleotide is lyophilized.
249. The method according to Clause 247, wherein the de-activatable oligonucleotide is present in one or more droplets.
250. The method according to any of Clauses 246 to 250, wherein the method further comprises lysing a single cell in the single reaction vessel.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
elongating a de-activatable oligonucleotide via a template nucleic acid-mediated primer extension reaction to produce an extended nucleic acid; and
irreversibly deactivating the de-activatable oligonucleotide.

2. The method according to claim 1, wherein deactivating the de-activatable oligonucleotide comprises applying a deactivating stimulus selected from the group consisting of: an enzyme, a chemical agent and an electromagnetic stimulus.

3. The method according to claim 2, wherein the deactivating stimulus is an enzyme and the enzyme is ribonuclease H (RNase H).

4. The method according to claim 1, comprising a template switching reaction comprising a template switching oligonucleotide (TSO) to produce an extended nucleic acid that comprises a sequence complementary to the TSO.

5. The method according to claim 4, wherein the TSO is de-activatable.

6. The method according to claim 5, wherein the de-activatable oligonucleotide and the de-activatable TSO are deactivated by the same stimulus.

7. The method according to claim 4, wherein the de-activatable oligonucleotide, the TSO, or both comprise an adapter sequence, a barcode sequence, or a combination thereof.

8. The method according to claim 1, wherein the method further comprises amplifying the extended nucleic acid.

9. The method according to claim 1, wherein the method further comprises a tagmentation reaction.

10. The method according to claim 2, wherein the deactivating stimulus is an enzyme.

11. The method according to claim 2, wherein the deactivating stimulus is a chemical agent.

12. The method according to claim 2, wherein the deactivating stimulus is an electromagnetic stimulus.

13. The method according to claim 12, wherein the electromagnetic stimulus is light.

14. The method according to claim 1, wherein deactivating the de-activatable oligonucleotide comprises selectively cleaving one or more selectively cleavable linkages present in the de-activatable oligonucleotide.

15. The method according to claim 14, wherein the de-activatable oligonucleotide is cleaved into multiple fragments.

16. The method according to claim 2, wherein the deactivating stimulus is capable of cleaving one or more selectively cleavable linkages present in the de-activatable oligonucleotide.

17. The method according to claim 1, wherein deactivating the de-activatable oligonucleotide destroys a pre-deactivation function of the de-activatable oligonucleotide.

18. The method according to claim 1, wherein the deactivated de-activatable oligonucleotide is present in a later reaction without interfering with a downstream reaction step.

19. The method according to claim 1, wherein the de-activatable oligonucleotide is deactivated in its unhybridized state, its hybridized state, or both.

* * * * *

UNITED STATES PATENT AND TRADEMARK OFFICE
CERTIFICATE OF CORRECTION

| | |
|---|---|
| PATENT NO. | : 11,667,952 B2 |
| APPLICATION NO. | : 16/603788 |
| DATED | : June 6, 2023 |
| INVENTOR(S) | : Kazuo Tori |

It is certified that error appears in the above-identified patent and that said Letters Patent is hereby corrected as shown below:

In the Specification

Please replace "±10" with -- ±10° -- (Column 9, Line 33).

Please replace "±5" with -- ±5° -- (Column 9, Line 34).

Please replace "(IncRNA)," with -- (lncRNA), -- (Column 26, Line 14).

Please replace "and or" with -- and/or -- (Column 27, Line 62).

Please replace "dimethychlorosilane, dimethydichlorosilane," with -- dimethylchlorosilane, dimethyldichlorosilane, -- (Column 48, Lines 33-34).

Please replace "and or" with -- and/or -- (Column 48, Line 64).

Please replace "sequence," with -- sequence. -- (Column 59, Line 42).

Please replace "enzyme" with -- enzyme. -- (Column 62, Line 51).

Please replace "Claus" with -- Clause -- (Column 62, Line 60).

Signed and Sealed this
Fifteenth Day of August, 2023

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 322
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: misc_feature
<222> LOCATION: (14)..(14)
<223> OTHER INFORMATION: n is a, c, g, t or u
```

-continued

```
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (70)..(70)
<223> OTHER INFORMATION: n is a, c, g, t or u
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (105)..(105)
<223> OTHER INFORMATION: n is a, c, g, t or u
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (144)..(144)
<223> OTHER INFORMATION: n is a, c, g, t or u
<220> FEATURE:
<221> NAME/KEY: misc_feature
<222> LOCATION: (147)..(147)
<223> OTHER INFORMATION: n is a, c, g, t or u
<220> FEATURE:
<221> NAME/KEY: misc_feature
<222> LOCATION: (156)..(156)
<223> OTHER INFORMATION: n is a, c, g, t or u
<220> FEATURE:
<221> NAME/KEY: misc_feature
<222> LOCATION: (192)..(192)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (204)..(204)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u
<220> FEATURE:
<221> NAME/KEY: misc_feature
<222> LOCATION: (244)..(244)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u
<220> FEATURE:
<221> NAME/KEY: misc_feature
<222> LOCATION: (286)..(286)
<223> OTHER INFORMATION: n is a, c, g, t or u
```

```
<220> FEATURE:
<221> NAME/KEY: misc_feature
<222> LOCATION: (289)..(289)
<223> OTHER INFORMATION: n is a, c, g, t or u
<220> FEATURE:
<221> NAME/KEY: misc_feature
<222> LOCATION: (298)..(298)
<223> OTHER INFORMATION: n is a, c, g, t or u

<400> SEQUENCE: 1
dnarnaartc asuncagatg tgtataagag acagdnarna artcasuncc tgtctcttat      60
acacatctdn arnaartcas uncaatgata cggcgaccac cgadnarnaa rtcasuncca     120
agcagaagac ggcatacgag atdnarnaar tcasuncaca ctctttccct acacgacgct     180
cttccgatct dnarnaartc asuncgtgac tggagttcag acgtgtgctc ttccgatctd     240
narnaartca suncccatct catccctgcg tgtctccgac tcagdnarna artcasuncc     300
ctctctatgg gcagtcggtg at                                              322
```